US 11,666,470 B2

(12) United States Patent
Stangenes et al.

(10) Patent No.: US 11,666,470 B2
(45) Date of Patent: Jun. 6, 2023

(54) PYLORIC ANCHOR RETRIEVAL TOOLS AND METHODS

(71) Applicant: MetaModix, Inc., Plymouth, MN (US)

(72) Inventors: Todd Stangenes, Minneapolis, MN (US); Werner Schwarz, Ruhpolding (DE); Kedar R. Belhe, Minnetonka, MN (US); Mathew Ziebol, Blaine, MN (US); Edward Anderson, Maple Grove, MN (US)

(73) Assignee: MetaModix, Inc, Plymouth, MN (US)

( * ) Notice: Subject to any disclaimer, the term of this patent is extended or adjusted under 35 U.S.C. 154(b) by 347 days.

(21) Appl. No.: 16/843,691

(22) Filed: Apr. 8, 2020

(65) Prior Publication Data
US 2020/0229958 A1    Jul. 23, 2020

Related U.S. Application Data

(63) Continuation of application No. 15/600,214, filed on May 19, 2017, now Pat. No. 10,751,209.
(Continued)

(51) Int. Cl.
*A61F 5/00* (2006.01)
*A61B 17/00* (2006.01)
*A61F 2/95* (2013.01)

(52) U.S. Cl.
CPC ...... *A61F 5/0089* (2013.01); *A61B 17/00234* (2013.01); *A61F 5/0079* (2013.01);
(Continued)

(58) Field of Classification Search
CPC ................. A61F 5/0089; A61F 5/0079; A61F 2002/9528; A61B 17/00234; A61B 50/30;
(Continued)

(56) References Cited

U.S. PATENT DOCUMENTS

| 4,134,405 A | 1/1979 | Smit |
| 4,204,530 A | 5/1980 | Finney |

(Continued)

FOREIGN PATENT DOCUMENTS

| AU | 2006227471 B2 | 6/2010 |
| AU | 2014200766 B2 | 6/2015 |

(Continued)

OTHER PUBLICATIONS

Better Nutrition: Your guide to Natural Living, Bouncing Back (http://www.betternutrition.com/natural-surgery-recovery-antiobiotics-pro-biotics/), Sep. 2009, accessed Jun. 14, 2016.
(Continued)

*Primary Examiner* — Richard G Louis
(74) *Attorney, Agent, or Firm* — Faegre Drinker Biddle & Reath LLP

(57) ABSTRACT

A retrieval device comprising a hook assembly and a capsule assembly. The hook assembly has an attachment feature at a first end. The capsule assembly includes a capsule, a capsule shaft, and a handle connected in series and defining an inner bore. The capsule has a first end defining an opening. The inner bore of the capsule assembly is configured to slidably receive the hook assembly. The handle has a central portion, a first extension portion attached to the capsule shaft, and a second extension portion with a hook assembly lock at a second end. The hook assembly lock is configured to lock the hook assembly to the second extension portion. The second extension portion is configured to pull the hook assembly relative to the capsule shaft, and the first extension portion is configured to push the capsule shaft relative to the hook assembly along the central longitudinal axis.

18 Claims, 39 Drawing Sheets

Related U.S. Application Data

(60) Provisional application No. 62/338,896, filed on May 19, 2016.

(52) U.S. Cl.
CPC .............. *A61B 2017/00292* (2013.01); *A61B 2017/00336* (2013.01); *A61B 2017/00349* (2013.01); *A61B 2017/00362* (2013.01); *A61B 2017/00818* (2013.01); *A61F 2002/9528* (2013.01)

(58) Field of Classification Search
CPC ........... A61B 2017/00292; A61B 2017/00349; A61B 2017/00362; A61B 2017/00818; A61B 2017/00296
See application file for complete search history.

(56) References Cited

U.S. PATENT DOCUMENTS

| | | |
|---|---|---|
| 4,246,893 A | 1/1981 | Berson |
| 4,314,405 A | 2/1982 | Park |
| 4,315,509 A | 2/1982 | Smit |
| 4,416,267 A | 11/1983 | Garren et al. |
| 4,501,264 A | 2/1985 | Rockey |
| 4,641,653 A | 2/1987 | Rockey |
| 4,716,900 A | 1/1988 | Ravo et al. |
| 4,719,916 A | 1/1988 | Ravo |
| 4,763,653 A | 8/1988 | Rockey |
| 4,899,747 A | 2/1990 | Garren et al. |
| 4,905,693 A | 3/1990 | Ravo |
| 5,234,454 A | 8/1993 | Bangs |
| 5,246,456 A | 9/1993 | Wilkinson |
| 5,306,300 A | 4/1994 | Berry |
| 5,322,697 A | 6/1994 | Meyer |
| 5,423,872 A | 6/1995 | Cigaina |
| 5,474,563 A | 12/1995 | Myler et al. |
| 5,480,423 A | 1/1996 | Ravenscroft et al. |
| 5,643,175 A | 7/1997 | Adair |
| 5,749,921 A | 5/1998 | Lenker et al. |
| 5,753,253 A | 5/1998 | Meyer |
| 5,755,769 A | 5/1998 | Richard et al. |
| 5,820,584 A | 10/1998 | Crabb |
| 5,824,040 A | 10/1998 | Cox et al. |
| 5,860,913 A | 1/1999 | Yamaya et al. |
| 6,017,563 A | 1/2000 | Knight et al. |
| 6,224,627 B1 | 5/2001 | Armstrong et al. |
| 6,241,738 B1 | 6/2001 | Dereume |
| 6,267,988 B1 | 7/2001 | Meyer |
| 6,454,699 B1 | 9/2002 | Forsell |
| 6,540,789 B1 | 4/2003 | Silverman et al. |
| 6,558,400 B2 | 5/2003 | Deem et al. |
| 6,675,809 B2 | 1/2004 | Stack et al. |
| 6,676,674 B1 | 1/2004 | Moshe |
| 6,740,121 B2 | 5/2004 | Geitz |
| 6,755,869 B2 | 6/2004 | Geitz |
| 6,802,868 B2 | 10/2004 | Silverman et al. |
| 6,845,776 B2 | 1/2005 | Stack et al. |
| 6,946,002 B2 | 9/2005 | Geitz |
| 6,994,095 B2 | 2/2006 | Burnett |
| 7,025,791 B2 | 4/2006 | Levine et al. |
| 7,037,343 B2 | 5/2006 | Imran |
| 7,037,344 B2 | 5/2006 | Kagan et al. |
| 7,044,979 B2 | 5/2006 | Silverman et al. |
| 7,090,699 B2 | 8/2006 | Geitz |
| 7,111,627 B2 | 9/2006 | Stack et al. |
| 7,121,283 B2 | 10/2006 | Stack et al. |
| 7,122,058 B2 | 10/2006 | Levine et al. |
| 7,146,984 B2 | 12/2006 | Stack et al. |
| 7,152,607 B2 | 12/2006 | Stack et al. |
| 7,160,312 B2 | 1/2007 | Saadat |
| 7,163,554 B2 | 1/2007 | Williams et al. |
| 7,175,638 B2 | 2/2007 | Gannoe et al. |
| 7,175,669 B2 | 2/2007 | Geitz |
| 7,211,094 B2 | 5/2007 | Gannoe et al. |
| 7,211,114 B2 | 5/2007 | Bessler et al. |
| 7,214,233 B2 | 5/2007 | Gannoe et al. |
| 7,220,237 B2 | 5/2007 | Gannoe et al. |
| 7,220,284 B2 | 5/2007 | Kagan et al. |
| 7,223,277 B2 | 5/2007 | Delegge |
| 7,229,428 B2 | 6/2007 | Gannoe et al. |
| 7,261,725 B2 | 8/2007 | Binmoeller |
| 7,267,694 B2 | 9/2007 | Levine et al. |
| 7,288,099 B2 | 10/2007 | Deem et al. |
| 7,288,101 B2 | 10/2007 | Deem et al. |
| 7,291,160 B2 | 11/2007 | DeLegge |
| 7,306,614 B2 | 12/2007 | Weller et al. |
| 7,314,489 B2 | 1/2008 | McKenna et al. |
| 7,316,716 B2 | 1/2008 | Egan |
| 7,329,285 B2 | 2/2008 | Levine et al. |
| 7,335,210 B2 | 2/2008 | Smit |
| 7,347,875 B2 | 3/2008 | Levine et al. |
| 7,354,454 B2 | 4/2008 | Stack et al. |
| 7,364,542 B2 | 4/2008 | Jambor et al. |
| 7,364,591 B2 | 4/2008 | Silverman et al. |
| 7,367,937 B2 | 5/2008 | Jambor et al. |
| 7,431,725 B2 | 10/2008 | Stack et al. |
| 7,476,256 B2 | 1/2009 | Meade et al. |
| 7,503,922 B2 | 3/2009 | Deem et al. |
| 7,507,218 B2 | 3/2009 | Aliski et al. |
| 7,510,559 B2 | 3/2009 | Deem et al. |
| 7,513,914 B2 | 4/2009 | Schurr |
| 7,569,056 B2 | 8/2009 | Cragg et al. |
| 7,601,178 B2 | 10/2009 | Imran |
| 7,608,114 B2 | 10/2009 | Levine et al. |
| 7,608,578 B2 | 10/2009 | Miller |
| 7,618,435 B2 | 11/2009 | Opolski |
| 7,628,821 B2 | 12/2009 | Stack et al. |
| 7,678,068 B2 | 3/2010 | Levine et al. |
| 7,682,330 B2 | 3/2010 | Meade et al. |
| 7,695,446 B2 | 4/2010 | Levine et al. |
| 7,758,535 B2 | 7/2010 | Levine et al. |
| 7,766,861 B2 | 8/2010 | Levine et al. |
| 7,766,973 B2 | 8/2010 | Levine et al. |
| 7,815,589 B2 | 10/2010 | Meade et al. |
| 7,831,412 B1 | 11/2010 | Sobel et al. |
| 7,837,643 B2 | 11/2010 | Levine et al. |
| 7,837,669 B2 | 11/2010 | Dann et al. |
| 7,935,073 B2 | 5/2011 | Levine et al. |
| 7,976,488 B2 | 7/2011 | Levine et al. |
| 7,981,163 B2 | 7/2011 | Meade et al. |
| 8,105,392 B2 | 1/2012 | Durgin |
| 8,114,045 B2 | 2/2012 | Surti |
| 8,182,441 B2 | 5/2012 | Swain et al. |
| 8,183,441 B2 | 5/2012 | Cukadar |
| 8,211,186 B2 | 7/2012 | Belhe et al. |
| 8,282,598 B2 | 10/2012 | Belhe et al. |
| 8,579,849 B2 | 11/2013 | Grau et al. |
| 8,621,638 B2 | 12/2013 | Judge et al. |
| 8,702,641 B2 | 4/2014 | Belhe et al. |
| 8,702,642 B2 | 4/2014 | Belhe et al. |
| 8,814,931 B2 | 8/2014 | Wang et al. |
| 8,882,698 B2 | 11/2014 | Levine et al. |
| 9,044,300 B2 | 6/2015 | Belhe et al. |
| 9,173,760 B2 | 11/2015 | Belhe et al. |
| 9,278,019 B2 | 3/2016 | Thompson et al. |
| 9,622,897 B1 | 4/2017 | Stangenes et al. |
| 9,962,278 B2 | 5/2018 | Belhe et al. |
| 10,322,021 B2 | 6/2019 | Belhe et al. |
| 10,751,209 B2 * | 8/2020 | Stangenes ............. A61F 5/0089 |
| 2002/0183768 A1 | 12/2002 | Deem et al. |
| 2002/0188354 A1 | 12/2002 | Peghini |
| 2003/0004537 A1 | 1/2003 | Boyle et al. |
| 2003/0040804 A1 | 2/2003 | Stack et al. |
| 2003/0040808 A1 | 2/2003 | Stack et al. |
| 2003/0060894 A1 | 3/2003 | Du et al. |
| 2003/0109892 A1 | 6/2003 | Deem et al. |
| 2003/0109931 A1 | 6/2003 | Geitz |
| 2003/0109935 A1 | 6/2003 | Geitz |
| 2003/0120265 A1 | 6/2003 | Deem et al. |
| 2003/0158601 A1 | 8/2003 | Silverman et al. |
| 2003/0191476 A1 | 10/2003 | Smit |
| 2003/0199989 A1 | 10/2003 | Stack et al. |
| 2003/0199990 A1 | 10/2003 | Stack et al. |

(56) References Cited

U.S. PATENT DOCUMENTS

| | | |
|---|---|---|
| 2003/0199991 A1 | 10/2003 | Stack et al. |
| 2004/0019388 A1 | 1/2004 | Starkebaum |
| 2004/0024386 A1 | 2/2004 | Deem et al. |
| 2004/0039452 A1 | 2/2004 | Bessler |
| 2004/0088022 A1 | 5/2004 | Chen |
| 2004/0092892 A1 | 5/2004 | Kagan et al. |
| 2004/0093091 A1 | 5/2004 | Gannoe et al. |
| 2004/0107004 A1 | 6/2004 | Levine et al. |
| 2004/0117031 A1 | 6/2004 | Stack et al. |
| 2004/0122452 A1 | 6/2004 | Deem et al. |
| 2004/0122453 A1 | 6/2004 | Deem et al. |
| 2004/0122526 A1 | 6/2004 | Imran |
| 2004/0133147 A1 | 7/2004 | Woo |
| 2004/0138760 A1 | 7/2004 | Schurr |
| 2004/0138761 A1 | 7/2004 | Stack et al. |
| 2004/0143342 A1 | 7/2004 | Stack et al. |
| 2004/0148034 A1 | 7/2004 | Kagan et al. |
| 2004/0158331 A1 | 8/2004 | Stack et al. |
| 2004/0172141 A1 | 9/2004 | Stack et al. |
| 2004/0172142 A1 | 9/2004 | Stack et al. |
| 2004/0172143 A1 | 9/2004 | Geitz |
| 2004/0199262 A1 | 10/2004 | Du et al. |
| 2004/0204768 A1 | 10/2004 | Geitz |
| 2004/0220682 A1 | 11/2004 | Levine et al. |
| 2004/0249362 A1 | 12/2004 | Levine et al. |
| 2004/0267291 A1 | 12/2004 | Byrum et al. |
| 2005/0004681 A1 | 1/2005 | Stack et al. |
| 2005/0022827 A1 | 2/2005 | Woo et al. |
| 2005/0033226 A1 | 2/2005 | Kim |
| 2005/0033331 A1 | 2/2005 | Burnett et al. |
| 2005/0043817 A1 | 2/2005 | Mckenna et al. |
| 2005/0049718 A1 | 3/2005 | Dann et al. |
| 2005/0055039 A1 | 3/2005 | Burnett et al. |
| 2005/0070934 A1 | 3/2005 | Tanaka et al. |
| 2005/0075622 A1 | 4/2005 | Levine et al. |
| 2005/0080395 A1 | 4/2005 | Levine et al. |
| 2005/0080431 A1 | 4/2005 | Levine et al. |
| 2005/0080444 A1 | 4/2005 | Kraemer et al. |
| 2005/0080480 A1 | 4/2005 | Bolea et al. |
| 2005/0080491 A1 | 4/2005 | Levine et al. |
| 2005/0085923 A1 | 4/2005 | Levine et al. |
| 2005/0096673 A1 | 5/2005 | Stack et al. |
| 2005/0096750 A1 | 5/2005 | Kagan et al. |
| 2005/0125020 A1 | 6/2005 | Meade et al. |
| 2005/0125075 A1 | 6/2005 | Meade et al. |
| 2005/0149200 A1 | 7/2005 | Silverman et al. |
| 2005/0177181 A1 | 8/2005 | Kagan et al. |
| 2005/0183730 A1 | 8/2005 | Byrum |
| 2005/0192614 A1 | 9/2005 | Binmoeller |
| 2005/0197714 A1 | 9/2005 | Sayet |
| 2005/0228413 A1 | 10/2005 | Binmoeller et al. |
| 2005/0228504 A1 | 10/2005 | Demarais |
| 2005/0240279 A1 | 10/2005 | Kagan et al. |
| 2005/0246037 A1 | 11/2005 | Starkebaum |
| 2005/0247320 A1 | 11/2005 | Stack et al. |
| 2005/0250980 A1 | 11/2005 | Swanstrom et al. |
| 2005/0251157 A1 | 11/2005 | Saadat et al. |
| 2005/0251206 A1 | 11/2005 | Maahs et al. |
| 2005/0256587 A1 | 11/2005 | Egan |
| 2005/0267499 A1 | 12/2005 | Stack et al. |
| 2005/0273060 A1 | 12/2005 | Levy et al. |
| 2005/0277963 A1 | 12/2005 | Fields |
| 2005/0283107 A1 | 12/2005 | Kalanovic et al. |
| 2005/0288555 A1 | 12/2005 | Binmoeller |
| 2006/0009858 A1 | 1/2006 | Levine et al. |
| 2006/0020247 A1 | 1/2006 | Kagan et al. |
| 2006/0020277 A1 | 1/2006 | Gostout et al. |
| 2006/0030949 A1 | 2/2006 | Geitz |
| 2006/0036267 A1 | 2/2006 | Saadat et al. |
| 2006/0064120 A1 | 3/2006 | Levine et al. |
| 2006/0155310 A1 | 7/2006 | Binmoeller |
| 2006/0155312 A1 | 7/2006 | Levine et al. |
| 2006/0155375 A1 | 7/2006 | Kagan et al. |
| 2006/0161139 A1 | 7/2006 | Levine et al. |
| 2006/0161172 A1 | 7/2006 | Levine et al. |
| 2006/0161187 A1 | 7/2006 | Levine et al. |
| 2006/0161265 A1 | 7/2006 | Levine et al. |
| 2006/0178691 A1 | 8/2006 | Binmoeller |
| 2006/0206063 A1 | 9/2006 | Kagan et al. |
| 2006/0206064 A1 | 9/2006 | Kagan et al. |
| 2006/0212042 A1 | 9/2006 | Lamport et al. |
| 2006/0249165 A1 | 11/2006 | Silverman et al. |
| 2006/0258906 A1 | 11/2006 | Binmoeller |
| 2006/0265082 A1 | 11/2006 | Meade et al. |
| 2006/0282087 A1 | 12/2006 | Binmoeller |
| 2006/0293742 A1 | 12/2006 | Dann et al. |
| 2007/0004963 A1 | 1/2007 | Benchetrit |
| 2007/0005147 A1 | 1/2007 | Levine et al. |
| 2007/0010794 A1 | 1/2007 | Dann et al. |
| 2007/0010864 A1 | 1/2007 | Dann et al. |
| 2007/0010865 A1 | 1/2007 | Dann et al. |
| 2007/0010866 A1 | 1/2007 | Dann et al. |
| 2007/0021761 A1 | 1/2007 | Phillips |
| 2007/0027548 A1 | 2/2007 | Levine et al. |
| 2007/0032702 A1 | 2/2007 | Ortiz |
| 2007/0032879 A1 | 2/2007 | Levine et al. |
| 2007/0038308 A1 | 2/2007 | Geitz |
| 2007/0060932 A1 | 3/2007 | Stack et al. |
| 2007/0078302 A1 | 4/2007 | Ortiz et al. |
| 2007/0083271 A1 | 4/2007 | Levine et al. |
| 2007/0100367 A1 | 5/2007 | Quijano et al. |
| 2007/0118158 A1 | 5/2007 | Deem et al. |
| 2007/0118159 A1 | 5/2007 | Deem et al. |
| 2007/0135825 A1 | 6/2007 | Binmoeller |
| 2007/0167963 A1 | 7/2007 | Deem et al. |
| 2007/0198074 A1 | 8/2007 | Dann et al. |
| 2007/0203517 A1 | 8/2007 | Williams et al. |
| 2007/0213740 A1 | 9/2007 | Deem et al. |
| 2007/0213748 A1 | 9/2007 | Deem et al. |
| 2007/0213751 A1 | 9/2007 | Scirica et al. |
| 2007/0213837 A1 | 9/2007 | Ferreri et al. |
| 2007/0219570 A1 | 9/2007 | Deem et al. |
| 2007/0239284 A1 | 10/2007 | Skerven et al. |
| 2007/0250083 A1 | 10/2007 | Deem et al. |
| 2007/0250132 A1 | 10/2007 | Burnett |
| 2007/0265709 A1 | 11/2007 | Rajan et al. |
| 2007/0276432 A1 | 11/2007 | Stack et al. |
| 2007/0282349 A1 | 12/2007 | Deem et al. |
| 2007/0282418 A1 | 12/2007 | Weitzner |
| 2007/0282452 A1 | 12/2007 | Weitzner et al. |
| 2007/0282453 A1 | 12/2007 | Weitzner et al. |
| 2007/0282454 A1 | 12/2007 | Krueger et al. |
| 2007/0293885 A1 | 12/2007 | Binmoeller |
| 2008/0033574 A1 | 2/2008 | Bessler et al. |
| 2008/0045803 A1 | 2/2008 | Williams et al. |
| 2008/0065122 A1 | 3/2008 | Stack et al. |
| 2008/0065136 A1 | 3/2008 | Young |
| 2008/0071383 A1 | 3/2008 | Levine et al. |
| 2008/0086214 A1 | 4/2008 | Hardin et al. |
| 2008/0092910 A1 | 4/2008 | Brooks |
| 2008/0097466 A1 | 4/2008 | Levine et al. |
| 2008/0103604 A1 | 5/2008 | Levine et al. |
| 2008/0109086 A1 | 5/2008 | Voegele et al. |
| 2008/0109087 A1 | 5/2008 | Durgin |
| 2008/0140172 A1 | 6/2008 | Carpenter et al. |
| 2008/0161935 A1 | 7/2008 | Albrecht et al. |
| 2008/0167606 A1 | 7/2008 | Dann et al. |
| 2008/0167610 A1 | 7/2008 | Dann et al. |
| 2008/0167629 A1 | 7/2008 | Dann et al. |
| 2008/0167724 A1 | 7/2008 | Ruane et al. |
| 2008/0183238 A1 | 7/2008 | Chen |
| 2008/0195225 A1 | 8/2008 | Silverman et al. |
| 2008/0195226 A1 | 8/2008 | Williams et al. |
| 2008/0208135 A1 | 8/2008 | Annunziata |
| 2008/0208161 A1 | 8/2008 | Kaji et al. |
| 2008/0208224 A1 | 8/2008 | Surti et al. |
| 2008/0208239 A1 | 8/2008 | Annunziata |
| 2008/0208355 A1 | 8/2008 | Stack et al. |
| 2008/0208356 A1 | 8/2008 | Stack et al. |
| 2008/0208357 A1 | 8/2008 | Melanson et al. |
| 2008/0221595 A1 | 9/2008 | Surti |
| 2008/0221597 A1 | 9/2008 | Wallace et al. |
| 2008/0221702 A1 | 9/2008 | Wallace et al. |
| 2008/0234834 A1 | 9/2008 | Meade et al. |

(56) References Cited

U.S. PATENT DOCUMENTS

| | | |
|---|---|---|
| 2008/0243151 A1 | 10/2008 | Binmoeller et al. |
| 2008/0249533 A1 | 10/2008 | Godin |
| 2008/0249566 A1 | 10/2008 | Harris et al. |
| 2008/0249635 A1 | 10/2008 | Weitzner et al. |
| 2008/0255476 A1 | 10/2008 | Boyajian et al. |
| 2008/0255587 A1 | 10/2008 | Cully et al. |
| 2008/0255594 A1 | 10/2008 | Cully et al. |
| 2008/0255678 A1 | 10/2008 | Cully et al. |
| 2008/0262529 A1 | 10/2008 | Jacques |
| 2008/0262592 A1 | 10/2008 | Jordan et al. |
| 2008/0269715 A1 | 10/2008 | Faller et al. |
| 2008/0269797 A1 | 10/2008 | Stack et al. |
| 2008/0287969 A1 | 11/2008 | Tsonton et al. |
| 2008/0312559 A1 | 12/2008 | Santilli et al. |
| 2008/0319455 A1 | 12/2008 | Harris et al. |
| 2009/0005637 A1 | 1/2009 | Chin et al. |
| 2009/0012541 A1 | 1/2009 | Dahl et al. |
| 2009/0012542 A1 | 1/2009 | N'diaye et al. |
| 2009/0012544 A1 | 1/2009 | Thompson et al. |
| 2009/0012553 A1 | 1/2009 | Swain et al. |
| 2009/0076588 A1 | 3/2009 | Weber |
| 2009/0093767 A1 | 4/2009 | Kelleher |
| 2009/0093839 A1 | 4/2009 | Kelleher |
| 2009/0118749 A1 | 5/2009 | Shalon et al. |
| 2009/0125119 A1 | 5/2009 | Obermiller et al. |
| 2009/0138094 A1 | 5/2009 | Schurr |
| 2009/0149871 A9 | 6/2009 | Kagan et al. |
| 2009/0164028 A1 | 6/2009 | Chen |
| 2009/0177215 A1 | 7/2009 | Stack et al. |
| 2009/0182355 A1 | 7/2009 | Levine et al. |
| 2009/0187206 A1 | 7/2009 | Binmoeller et al. |
| 2009/0198210 A1 | 8/2009 | Burnett et al. |
| 2009/0216262 A1 | 8/2009 | Burnett et al. |
| 2009/0240105 A1 | 9/2009 | Smit et al. |
| 2009/0240340 A1 | 9/2009 | Levine et al. |
| 2009/0248171 A1 | 10/2009 | Levine et al. |
| 2009/0276055 A1 | 11/2009 | Harris et al. |
| 2009/0281379 A1 | 11/2009 | Binmoeller et al. |
| 2009/0299486 A1 | 12/2009 | Shohat et al. |
| 2009/0299487 A1 | 12/2009 | Stack et al. |
| 2009/0326433 A1 | 12/2009 | Albrecht et al. |
| 2009/0326675 A1 | 12/2009 | Albrecht et al. |
| 2010/0004755 A1 | 1/2010 | Imran |
| 2010/0016988 A1 | 1/2010 | Stack et al. |
| 2010/0030017 A1 | 2/2010 | Baker et al. |
| 2010/0114130 A1 | 5/2010 | Meade et al. |
| 2010/0135971 A1 | 6/2010 | Schiffrin |
| 2010/0191170 A1 | 7/2010 | Chang |
| 2010/0256775 A1 | 10/2010 | Belhe et al. |
| 2010/0305590 A1 | 12/2010 | Holmes et al. |
| 2011/0009690 A1 | 1/2011 | Belhe et al. |
| 2011/0054493 A1 | 3/2011 | Mclean et al. |
| 2011/0104327 A1 | 5/2011 | Kirejevas |
| 2011/0106273 A1 | 5/2011 | Belhe et al. |
| 2011/0295307 A1 | 12/2011 | Salahieh et al. |
| 2012/0004676 A1 | 1/2012 | Vargas |
| 2012/0065571 A1 | 3/2012 | Thompson et al. |
| 2012/0109188 A1 | 5/2012 | Frank |
| 2012/0136457 A1 | 5/2012 | Grau et al. |
| 2012/0184893 A1 | 7/2012 | Thompson et al. |
| 2012/0184967 A1 | 7/2012 | Levine et al. |
| 2012/0232460 A1 | 9/2012 | Raven et al. |
| 2012/0253259 A1 | 10/2012 | Belhe et al. |
| 2012/0253260 A1 | 10/2012 | Belhe et al. |
| 2012/0302936 A1 | 11/2012 | Belhe et al. |
| 2013/0030351 A1 | 1/2013 | Belhe et al. |
| 2013/0324907 A1 | 12/2013 | Huntley et al. |
| 2014/0018719 A1 | 1/2014 | Chamorro et al. |
| 2014/0194806 A1 | 7/2014 | Belhe et al. |
| 2014/0200502 A1 | 7/2014 | Belhe et al. |
| 2014/0213960 A1 | 7/2014 | Belhe et al. |
| 2014/0309576 A1 | 10/2014 | Belhe et al. |
| 2014/0350694 A1 | 11/2014 | Behan |
| 2014/0371652 A1 | 12/2014 | Aramaki et al. |
| 2014/0379093 A1 | 12/2014 | Durgin |
| 2016/0089256 A1 | 3/2016 | Belhe et al. |
| 2016/0228276 A1 | 8/2016 | Thompson et al. |
| 2017/0333240 A1 | 11/2017 | Stangenes et al. |
| 2019/0298560 A1 | 10/2019 | Belhe et al. |
| 2020/0000616 A1 | 1/2020 | Belhe et al. |

FOREIGN PATENT DOCUMENTS

| | | |
|---|---|---|
| CN | 1575155 A | 2/2005 |
| CN | 1618411 A | 5/2005 |
| DE | 3641935 A1 | 6/1987 |
| DE | 19630324 A1 | 1/1998 |
| EP | 0137878 A1 | 4/1985 |
| EP | 1420730 A2 | 5/2004 |
| EP | 1492477 A1 | 1/2005 |
| EP | 1492478 A1 | 1/2005 |
| EP | 1555970 A1 | 7/2005 |
| EP | 1569582 A2 | 9/2005 |
| EP | 1585458 A1 | 10/2005 |
| EP | 1680054 A1 | 7/2006 |
| EP | 1708641 A1 | 10/2006 |
| EP | 1708655 A1 | 10/2006 |
| EP | 1709508 A2 | 10/2006 |
| EP | 1749482 A2 | 2/2007 |
| EP | 1750595 A2 | 2/2007 |
| EP | 1778069 A1 | 5/2007 |
| EP | 1786310 A2 | 5/2007 |
| EP | 1799145 A1 | 6/2007 |
| EP | 1817072 A2 | 8/2007 |
| EP | 1832250 A1 | 9/2007 |
| EP | 1850811 A1 | 11/2007 |
| EP | 1850812 A1 | 11/2007 |
| EP | 1868513 A1 | 12/2007 |
| EP | 1881781 A2 | 1/2008 |
| EP | 1887977 A2 | 2/2008 |
| EP | 1887995 A2 | 2/2008 |
| EP | 1895887 A2 | 3/2008 |
| EP | 1937164 A1 | 7/2008 |
| EP | 1992314 A1 | 11/2008 |
| EP | 1416861 B1 | 12/2008 |
| EP | 1749480 B1 | 12/2008 |
| EP | 2010270 A2 | 1/2009 |
| EP | 1610720 B1 | 2/2009 |
| EP | 2023828 A2 | 2/2009 |
| EP | 2026713 A2 | 2/2009 |
| EP | 2061397 A1 | 5/2009 |
| EP | 2066243 A1 | 6/2009 |
| EP | 2068719 A2 | 6/2009 |
| EP | 2080242 A2 | 7/2009 |
| EP | 1520528 B1 | 9/2009 |
| EP | 1610719 B1 | 1/2010 |
| EP | 1603488 B1 | 4/2010 |
| EP | 1585460 B1 | 5/2010 |
| EP | 1933721 B1 | 5/2010 |
| EP | 1768618 B1 | 4/2011 |
| EP | 1883370 B1 | 8/2011 |
| EP | 2945566 A1 | 11/2015 |
| JP | 2005-500127 A | 1/2005 |
| JP | 2007-513684 A | 5/2007 |
| JP | 2007-513685 A | 5/2007 |
| JP | 2013-538606 A | 10/2013 |
| KR | 2012-0008492 A | 1/2012 |
| WO | 98/49943 A2 | 11/1998 |
| WO | 01/66020 A2 | 9/2001 |
| WO | 02/96327 A2 | 12/2002 |
| WO | 03/17882 A2 | 3/2003 |
| WO | 03/86246 A1 | 10/2003 |
| WO | 03/86247 A1 | 10/2003 |
| WO | 03/94785 A1 | 11/2003 |
| WO | 2004/011085 A1 | 2/2004 |
| WO | 2004/017863 A2 | 3/2004 |
| WO | 2004/041133 A1 | 5/2004 |
| WO | 2004/049982 A2 | 6/2004 |
| WO | 2004/064680 A1 | 8/2004 |
| WO | 2004/064685 A1 | 8/2004 |
| WO | 2004/087014 A2 | 10/2004 |
| WO | 2004/087233 A2 | 10/2004 |
| WO | 2005/037152 A1 | 4/2005 |
| WO | 2005/058415 A2 | 6/2005 |

(56) References Cited

FOREIGN PATENT DOCUMENTS

| | | |
|---|---|---|
| WO | 2005/060869 A1 | 7/2005 |
| WO | 2005/060882 A1 | 7/2005 |
| WO | 2005/065412 A2 | 7/2005 |
| WO | 2005/097012 A2 | 10/2005 |
| WO | 2005/099591 A2 | 10/2005 |
| WO | 2005/110244 A1 | 11/2005 |
| WO | 2005/110280 A2 | 11/2005 |
| WO | 2005/112822 A1 | 12/2005 |
| WO | 2005/120363 A1 | 12/2005 |
| WO | 2006/014496 A2 | 2/2006 |
| WO | 2006/016894 A1 | 2/2006 |
| WO | 2006/020370 A2 | 2/2006 |
| WO | 2006/023352 A1 | 3/2006 |
| WO | 2006/028898 A2 | 3/2006 |
| WO | 2006/034062 A1 | 3/2006 |
| WO | 2006/060049 A2 | 6/2006 |
| WO | 2006/062996 A2 | 6/2006 |
| WO | 2006/078781 A1 | 7/2006 |
| WO | 2006/078927 A1 | 7/2006 |
| WO | 2006/102012 A1 | 9/2006 |
| WO | 2006/102240 A2 | 9/2006 |
| WO | 2006/124880 A2 | 11/2006 |
| WO | 2006/127593 A2 | 11/2006 |
| WO | 2006/133311 A2 | 12/2006 |
| WO | 2006/135551 A2 | 12/2006 |
| WO | 2007/001468 A2 | 1/2007 |
| WO | 2007/019117 A1 | 2/2007 |
| WO | 2007/030829 A2 | 3/2007 |
| WO | 2007/038715 A1 | 4/2007 |
| WO | 2007/041598 A1 | 4/2007 |
| WO | 2007/075396 A2 | 7/2007 |
| WO | 2007/092390 A2 | 8/2007 |
| WO | 2007/107990 A2 | 9/2007 |
| WO | 2007/127209 A2 | 11/2007 |
| WO | 2007/136468 A2 | 11/2007 |
| WO | 2007/139920 A2 | 12/2007 |
| WO | 2007/142829 A1 | 12/2007 |
| WO | 2007/142832 A1 | 12/2007 |
| WO | 2007/142833 A1 | 12/2007 |
| WO | 2007/142834 A1 | 12/2007 |
| WO | 2007/145684 A2 | 12/2007 |
| WO | 2008/005510 A2 | 1/2008 |
| WO | 2008/030403 A1 | 3/2008 |
| WO | 2008/033409 A1 | 3/2008 |
| WO | 2008/033474 A2 | 3/2008 |
| WO | 2008/039800 A2 | 4/2008 |
| WO | 2008/101048 A2 | 8/2008 |
| WO | 2008/106041 A1 | 9/2008 |
| WO | 2008/106279 A1 | 9/2008 |
| WO | 2008/112942 A2 | 9/2008 |
| WO | 2008/127552 A2 | 10/2008 |
| WO | 2008/141288 A1 | 11/2008 |
| WO | 2008/148047 A2 | 12/2008 |
| WO | 2008/150905 A1 | 12/2008 |
| WO | 2008/154450 A1 | 12/2008 |
| WO | 2008/154594 A2 | 12/2008 |
| WO | 2009/011881 A1 | 1/2009 |
| WO | 2009/011882 A2 | 1/2009 |
| WO | 2009/012335 A1 | 1/2009 |
| WO | 2009/036244 A1 | 3/2009 |
| WO | 2009/046126 A1 | 4/2009 |
| WO | 2009/082710 A1 | 7/2009 |
| WO | 2009/085107 A1 | 7/2009 |
| WO | 2009/086549 A1 | 7/2009 |
| WO | 2009/097582 A1 | 8/2009 |
| WO | 2009/097585 A1 | 8/2009 |
| WO | 2010/115011 A1 | 10/2010 |
| WO | 2011/062882 A1 | 5/2011 |
| WO | 2011/073970 A1 | 6/2011 |
| WO | 2011/099940 A8 | 10/2011 |
| WO | 2012/026965 A2 | 3/2012 |
| WO | 2012/103531 A2 | 8/2012 |
| WO | 2014/113483 A1 | 7/2014 |
| WO | 2015/138465 A1 | 9/2015 |

OTHER PUBLICATIONS

Buchwald, Henry et al., "Bariatric Surgery: A Systematic Review and Meta-Analysis", JAMA, Oct. 13, 2004, 292(14), pp. 1724-1737.

Cummings, David E. et al., "Role of the bypassed proximal intestine in the antidiabetic effects of bariatric surgery", Surgery for Obesity and Related Diseases 3 2007, pp. 109-115.

Daniels, Stephen, "Probiotics may 'counter obesity and diabetes1: NIH study", Jul. 10, 2013, downloaded from http://www.nutraingredients-usa.com/research/probiotics-may-counter-obesity-and-diabetes-NIH-study, 2 pages.

International Search Report and Written Opinion issued in PCT/US12/58202, dated Jan. 23, 2013, 14 pages.

International Search Report and Written Opinion issued in PCT/US2010/029648, dated Aug. 24, 2010.

International Search Report and Written Opinion issued in PCT/US2010/041574, dated Jan. 25, 2011.

International Search Report and Written Opinion issued in PCT/US2011/020560, dated Mar. 28, 2011, 10 pages.

International Search Report and Written Opinion issued in PCT/US2011/061193.

International Search Report and Written Opinion issued in PCT/US2012/023048, dated Jun. 22, 2012.

International Search Report and Written Opinion issued in PCT/US2014/011702, dated Mar. 21, 2014, 9 pages.

International Search Report and Written Opinion issued in PCT/US2015/019730, dated Mar. 10, 2015, 15 pages.

International Search Report and Written Opinion received for PCT Patent Application No. PCT/US2017/033573, dated Oct. 12, 2017, 11 pages.

International Search Report and Written Opinion received for PCT Patent Application No. PCT/US2019/024950, dated Jul. 30, 2019, 11 pages.

Invitation to Pay Additional Fees issued in PCT/US2010/029648, mailed Jun. 1, 2010.

Invitation to Pay Additional Fees received for PCT Patent Application No. PCT/US2017/033573, mailed on Aug. 14, 2017, 2 pages.

Ley, Ruth E. et al., "Microbial ecology: human gut microbes associated with obesity", Nature, vol. 44, No. 7122, pp. 1022-1023, 2006.

Nachenberg, Carey S.; U.S. Appl. filed Mar. 31, 2009., U.S. Appl. No. 12/415,834.

Pories, Walter J. et al., "Surgical Treatment of Obesity and its Effect on Diabetes: 10-6 Follow-up", Am J Clin Nutr 1992, 55, 582S-585S.

Pories, Walter J. et al., "Who Would Have Thought It? An Operation Proves to be the Most Effective Therapy for Adult-Onset Diabetes Mellitus", Annals of Survery, Sep. 1995, 222(3), pp. 339-352.

Rodriguez-Grunert, Leonardo et al., "First Human Experience With endoscopically Delivered and retrieved duodenal-jejunal bypass sleeve", Surgery for Obesity and Related diseases 4 (2008) 55-59.

Rubino, Francesco et al., "Potential of Surgery for Curing Type 2 Diabetes Mellitus", Annals of Surgery, Nov. 2002, 236(5), 554-559.

Rubino, Francesco et al., "The Mechanism of Diabetes Control After Gastrointestinal Bypass Surgery Reveals a Role of the Proximal Small Intestine in the pathophysiology of Type 2 Diabetes", Annals of Surgery, 244(5), Nov. 2006, pp. 741-749.

Rubino, Francesco et al,, "Effect of Duodenal-Jejunal Exclusion in a Non-Obese Animal Model of Type 2 Diabetes", Annals of Surgery, vol. 239, No. 1, Jan. 2004, pp. 1-11.

Schouten, Ruben et al., "A Multicenter, Randomized Efficacy Study of the endoBarrier Gastrointestinal Liner for Presurgical Weight Loss Prior to Bariatric Surgery", Annals of Surgery, vol. 251, No. 2, Feb. 2010, pp. 236-243.

Strader, Apr. et al., "Weight Loss Through Ileal transposition is accompanied by increased ileal hormone secretion and synthesis in rats", Am J Physiol Endocrinol Metab 288: E447-E453, 2005.

Supplemental European Search Report issued in EP Application 14740554 dated Sep. 26, 2016, 7 pages.

(56) References Cited

OTHER PUBLICATIONS

Troy, Stephanie et al., "Intestinal Gluconeogenesis is a key factor for early metabolic changes after gastric bypass but not after gastric lap-band in mice", Cell metabolism 8, 201-211, Sep. 3, 2008.
US Application entitled Pyloric Anchors and Methods for Intestinal Bypass Sleeves filed Mar. 3, 2016, U.S. Appl. No. 15/060,418.
Vetter, Marlon et al., "Narrative Review: Effect of bariatric Surgery on Type 2 Diabetes Mellitus", Annals of Internal Medicine, Jan. 20, 2009, 150(2), pp. 94-104.
Woodard et al., Probiotics Improve Outcomes After Roux-en-Y Gastric Bypass Surgery: A Prospective Randomized Trial, J Gastrointest Surg (2009) 13:1198-1204.
Yadav, Hariom et al., Beneficial Metabolic Effects of a Probiotic via Butyrate-induced GLP-1 Hormone Secretion, Journal of Biological Chemistry, 2013, vol. 288, pp. 25088-25097.

\* cited by examiner

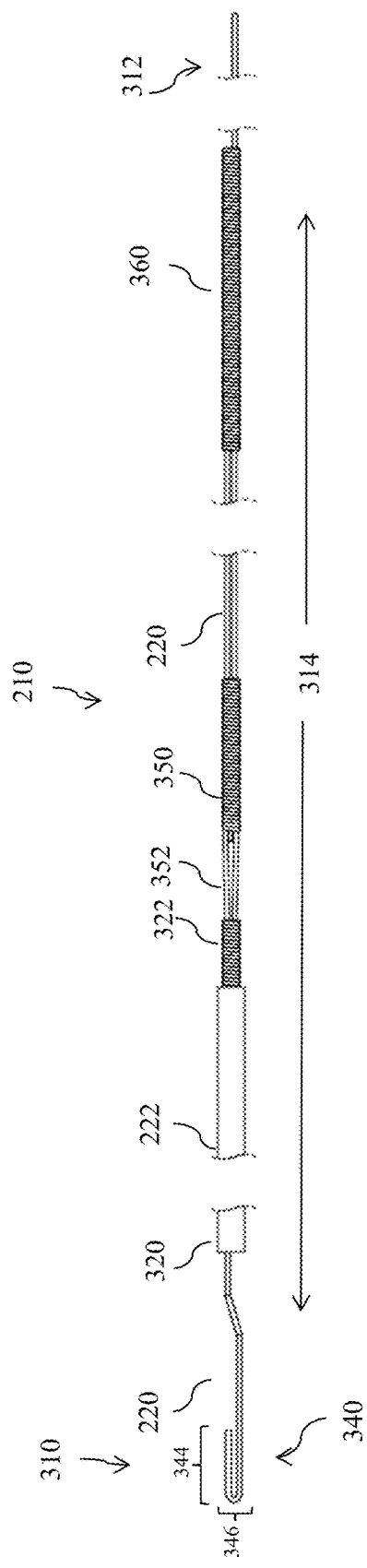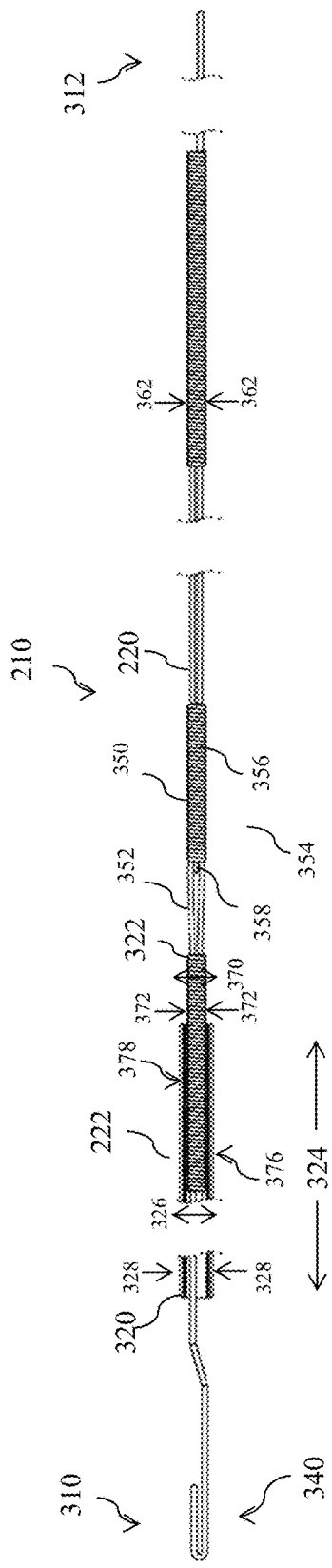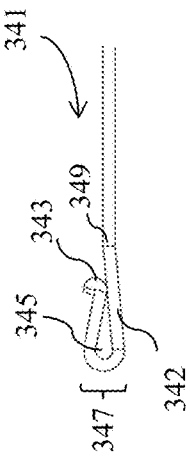
FIG. 9A
FIG. 9B
FIG. 9C

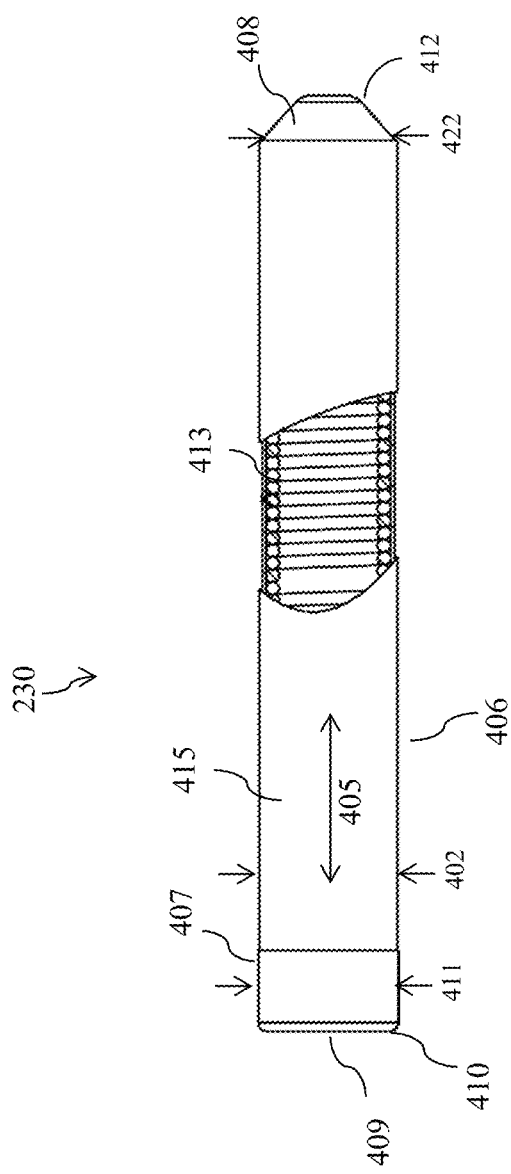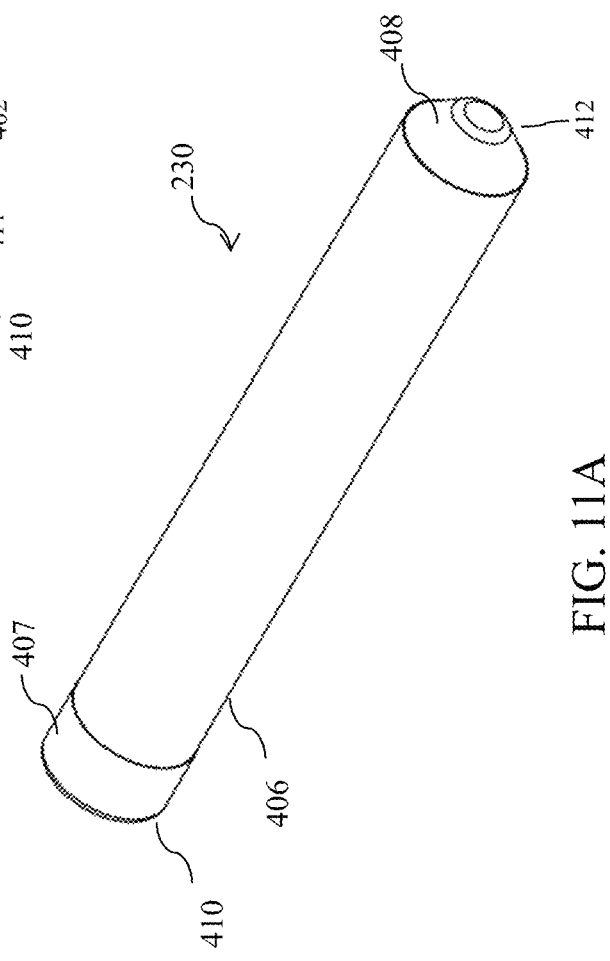
FIG. 11B
FIG. 11A

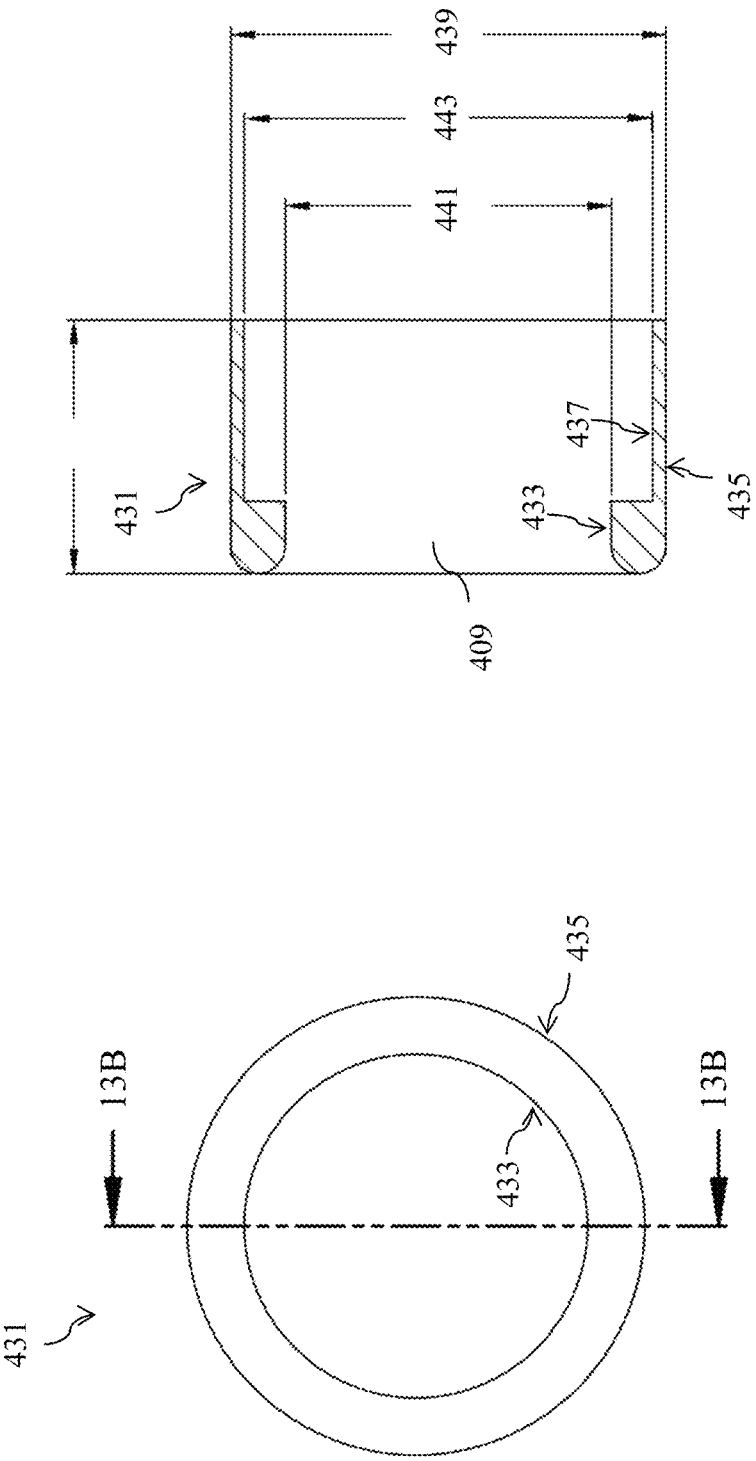

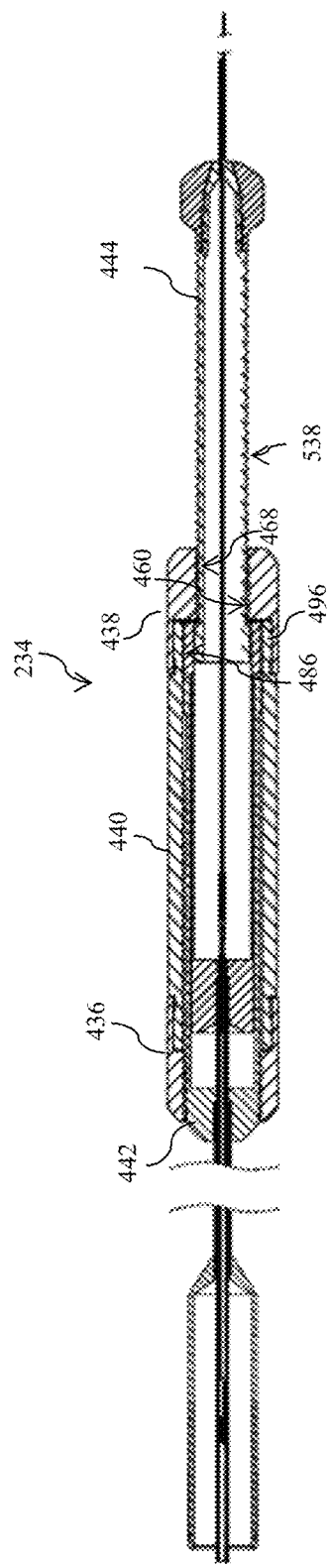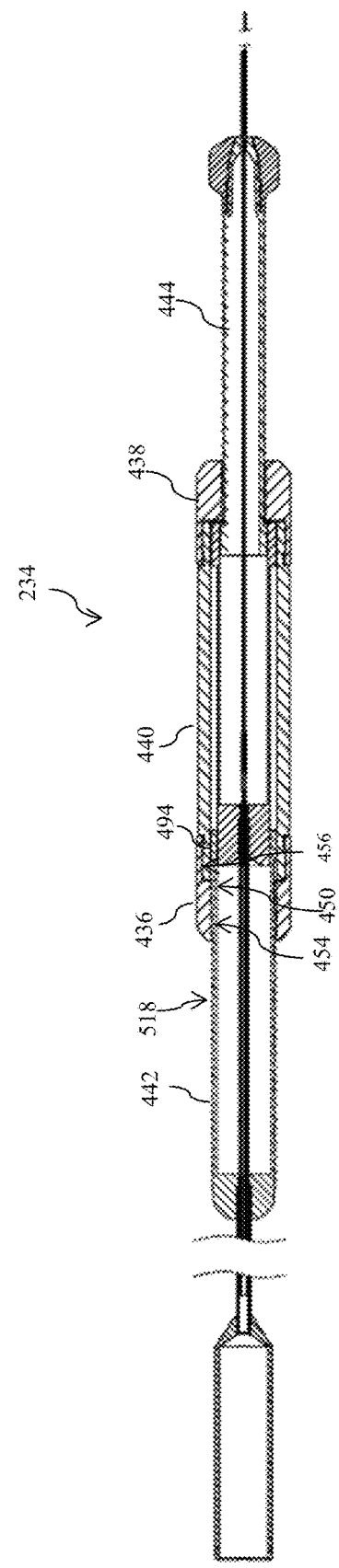
FIG. 22A
FIG. 22B

PYLORIC ANCHOR RETRIEVAL TOOLS AND METHODS

CROSS-REFERENCE TO RELATED APPLICATION

This application is a continuation of U.S. application Ser. No. 15/600,214, filed May 19, 2017, which claims priority to Provisional Application No. 62/338,896, filed May 19, 2016, both of which is herein incorporated by reference in its entirety.

TECHNICAL FIELD

The instant disclosure relates generally to implants placed within gastrointestinal systems, including the esophagus, the stomach and the intestine. More particularly, it relates to devices and methods for implanting and retrieving systems having components implantable and removable using endoscopic techniques for treatment of obesity, diabetes, reflux, gastroparesis and other gastrointestinal conditions.

BACKGROUND

Bariatric surgery procedures, such as sleeve gastrectomy, the Roux-en-Y gastric bypass (RYGB) and the bileo-pancreatic diversion (BPD), modify food intake and/or absorption within the gastrointestinal system to effect weight loss in obese patients. These procedures affect metabolic processes within the gastrointestinal system, by either short circuiting certain natural pathways or creating different interactions between the consumed food, the digestive tract, its secretions and the neuro-hormonal system regulating food intake and metabolism. In the last few years, there has been a growing clinical consensus that obese patients who undergo bariatric surgery see a remarkable resolution of their type-2 Diabetes Mellitus (T2DM) soon after the procedure. The remarkable resolution of diabetes after RYGB and BPD typically occurs too fast to be accounted for by weight loss alone, suggesting there may be a direct impact on glucose homeostasis. The mechanism of this resolution of T2DM is not well understood, and it is quite likely that multiple mechanisms are involved.

One of the drawbacks of bariatric surgical procedures is that they require fairly invasive surgery with potentially serious complications and long patient recovery periods. In recent years, there has been increased effort to develop minimally invasive procedures to mimic the effects of bariatric surgery. One such procedure involves the use of gastrointestinal implants that modify transport and absorption of food and organ secretions. For example, U.S. Pat. No. 7,476,256 describes an implant having a tubular sleeve with anchoring barbs, which offer the physician limited flexibility and are not readily removable or replaceable. Moreover, stents with active fixation means, such as barbs that deeply penetrate into surrounding tissue, may potentially cause tissue necrosis and erosion of the implants through the tissue, which can lead to complications, such as bacterial infection of the mucosal tissue or systemic infection. Also, due to the intermittent peristaltic motion within the digestive tract, implants such as stents have a tendency to migrate.

SUMMARY

Described herein is a retrieval device for retrieving a foreign body from within a patient. The retrieval device comprises an attachment assembly including an attachment cable having an arrest mechanism and an attachment cable sheath. The retrieval device also includes a capsule assembly including a capsule, a capsule sheath, and a handle having a first end attached to the capsule sheath second end, a second end having a cable assembly lock and defining a length between the handle first end and second end. The handle also has an elongation mechanism configured to elongate the handle such that in a first configuration the handle first end is a first distance from the handle second end, and in a second configuration the handle first end is a second distance from the handle second end. The capsule, capsule sheath, and handle inner diameter are sized to receive the attachment assembly outer diameter, and the cable assembly lock is configured to engage the attachment assembly arrest mechanism such that the attachment assembly is inhibited from moving relative to the handle in a longitudinal direction.

Also disclosed herein is an extractor system for extracting a medical device from within a patient. The extractor system comprises a connection assembly including an elongated wire having a connection mechanism, a wire lock, and an arrest mechanism. The retrieval device also has a wire lumen having a first end, a second end, an inner diameter, and an outer diameter, the second end defining an inner surface configured to engage the wire lock, the wire lumen configured to receive the elongated wire first end. The retrieval device also has a withdrawal mechanism including a retrieval lumen, a retrieval tube, and a tensioning system configured to extend the length of the tensioning system first end and second end from each other. The connection assembly is configured to be received within the withdrawal mechanism, and the tensioning system clamp is configured to prevent longitudinal movement of the elongated wire in relation to the tensioning system second end, such that extending the length of the tensioning system first end and second end from each other draws the elongated wire first end into retrieval lumen first end.

Also disclosed herein is a method of extracting a foreign object from within the body of a patient. The method comprises inserting a wire assembly into the patient, the wire assembly including a wire within a wire tube, the wire having a first end having an attachment device, and a second end, attaching the wire attachment device to the foreign object, and advancing a withdrawal sheath around the wire assembly and into the patient, the withdrawal sheath having a first open end, a length, and a second end having a wire locking mechanism. The method also includes fixing the wire locking mechanism to the wire second end; extending the withdrawal sheath length such that the wire assembly and foreign object is pulled into the withdrawal sheath first open end; and removing the withdrawal sheath having the foreign object inside the body of the patient.

Also disclosed herein is a method of removing a gastrointestinal device having a drawstring, an expandable proximal flange, and a distal flange from a patient. The method comprises inserting a hook assembly into the patient, the hook assembly including a first end, a second end, a hook cable having a hook, the hook cable received inside a hook sheath. The method also includes attaching the hook to the drawstring of the gastrointestinal device; drawing the hook cable into the hook sheath first end and pulling the drawstring into the hook sheath first end to collapse the expandable proximal flange; and advancing a capsule assembly over the hook assembly into the patient, the capsule assembly having a first end with a capsule, a length, and a second end. The method also includes securing the hook assembly second end to the capsule second end; elongating the capsule assembly such that the hook assembly first end and the collapsed proximal flange is drawn into the capsule assembly first end; advancing the hook assembly second end over the gastrointestinal device distal flange such that the distal flange is received within the capsule assembly first end; and withdrawing the capsule assembly containing the gastrointestinal device from the patient.

Also disclosed herein is a retrieval system for extracting implants from within a patient's body. The retrieval system includes an insertion assembly configured to be at least partially inserted within the patient's body. The insertion assembly includes a capsule having a length, an internal diameter, and an external diameter, and an elongated lumen connected to the capsule, the elongated lumen having a first end attached to the sheath, a second end, and a length in between, wherein the elongated lumen is configured to be minimally compressible along the length. The retrieval system also includes a handle assembly connected to the elongated lumen second end, configured to be located outside the patient's body, and including a screw mechanism. The screw mechanism is configured to provide a mechanical force to the insertion assembly, and the insertion assembly is configured to transmit the mechanical force to collapse the implant from a larger expanded configuration into a smaller contracted configuration and receive it within the capsule inner diameter.

Also disclosed herein is a retrieval system for capturing self-expandable stents from within a patient's body. The retrieval system comprises a protective capsule; a screw handle mechanism configured to impart a mechanical force required to collapse and receive the self-expandable stent within the protective capsule from a larger expandable configuration to a smaller collapsed configuration; and a minimally compressible catheter assembly attached to the protective capsule and the screw handle and configured to remotely transmit the mechanical force from the screw handle to the protective capsule.

Also disclosed herein is a retrieval device comprising a hook assembly and a capsule assembly. The hook assembly has a first end, a second end, and a length in between. The hook assembly has an attachment feature at the first end. The capsule assembly includes a capsule, a capsule shaft, and a handle connected in series and defining an inner bore along a length of the capsule assembly along a central longitudinal axis. The capsule has a first end defining an opening to an inside of the capsule. The inner bore of the capsule assembly is configured to slidably receive the hook assembly. The handle has a central portion, a first extension portion having a first end defining a first end of the handle and attached to the capsule shaft, and a second extension portion having a second end defining a second end of the handle. The second extension portion has a hook assembly lock at the second end. The handle has a retracted configuration with the first end a first distance from the second end, and an extended configuration with the first end a second distance from the second end along the central longitudinal axis. The hook assembly lock is configured to lock the hook assembly to the second extension portion. The second extension portion is configured to pull the hook assembly relative to the capsule shaft, and the first extension portion is configured to push the capsule shaft relative to the hook assembly along the central longitudinal axis.

Also disclosed herein is a retrieval device for retrieving an object from within the body of a patient. The retrieval device comprises a hook assembly and a capsule assembly. The hook assembly includes a sheath having a first end, a second end, and a wall extending between the first end and second end and defining a lumen in between. The hook assembly also includes a cable having an attachment feature at a first end. The cable is configured to be slidably received within the lumen of the sheath. A second end of the cable is configured to be locked to the second end of the sheath to inhibit longitudinal motion of the cable relative to the sheath. The capsule assembly includes a capsule, a capsule shaft, and a handle connected in series and defining an inner bore along a length of the capsule assembly. The capsule has a first end defining an opening to an inside of the capsule. The handle has a first end, a second end, and a hook assembly lock configured to lock the hook assembly to the second end of the handle such that the hook assembly is inhibited from moving relative to the second end of the handle. The handle has a retracted configuration with the first end a first distance from the second end, and an extended configuration with the first end a second distance from the second end. The inner bore of the capsule assembly is configured to slidably receive the hook assembly along a central longitudinal axis. Transitioning the handle between the retracted configuration and the expanded configuration slides the hook assembly relative to the capsule shaft along the central longitudinal axis.

Also disclosed herein is a method of extracting a medical device from within a patient. The method comprises inserting an attachment assembly into a body of a patient. The attachment assembly includes an attachment cable having a first end having an attachment feature, and a second end. The method includes coupling the attachment feature to a medical device positioned within the body of the patient and advancing a capsule assembly into the body of the patient with the capsule assembly around the attachment assembly. The capsule assembly has a capsule at a first end and a handle having a second end defining a second end of the capsule assembly. The method includes locking the second end of the attachment cable to the second end of the handle. The method also includes transitioning the handle from a collapsed configuration to an expanded configuration such that the handle draws the attachment assembly through the capsule assembly and the attachment feature is drawn into the capsule, and removing the capsule assembly and attachment assembly coupled to the medical device from inside the body of the patient.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 9A is an overall schematic of an attachment assembly, in accordance with various aspects of the present disclosure.

FIG. 9B is an overall schematic of an attachment assembly showing a cross sectional view, in accordance with various aspects of the present disclosure.

FIG. 9C is a side view of a hook that may be used with the attachment assembly of FIGS. 9A and 9B, in accordance with various aspects of the present disclosure.

FIG. 11A is a perspective view of a capsule, in accordance with various aspects of the present disclosure.

FIG. 11B is a side view of the capsule depicted in FIG. 11A with a partial cutaway view, in accordance with various aspects of the present disclosure.

FIG. 13A is an end view of a portion of the capsule depicted in FIG. 11A, in accordance with various aspects of the present disclosure.

FIG. 13B is a side view of a portion of the capsule depicted in FIG. 11A, in accordance with various aspects of the present disclosure.

FIG. 22A is an overall view of a handle in a contracted configuration, in accordance with various aspects of the present disclosure.

FIG. 22B is an overall view of a handle in an expanded configuration, in accordance with various aspects of the present disclosure.

DETAILED DESCRIPTION

Figure 1:
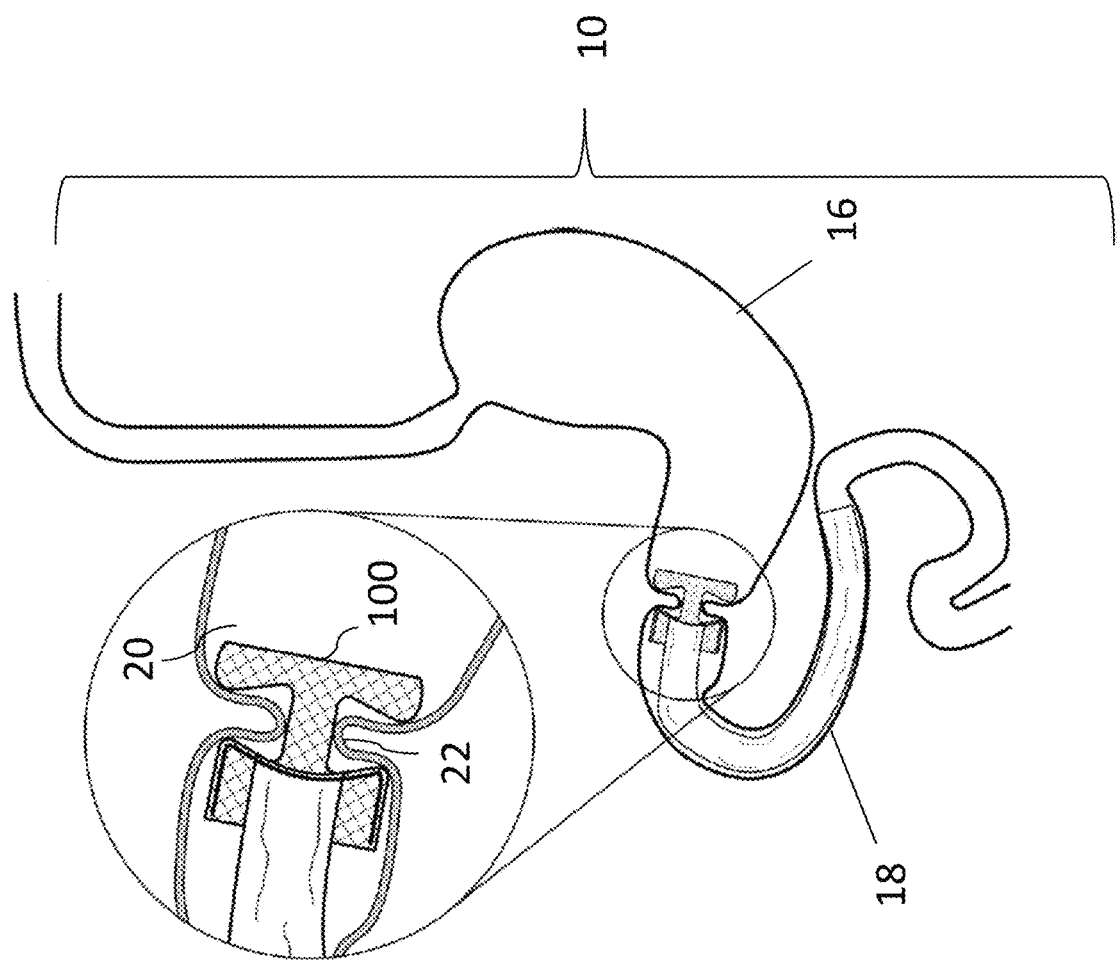
FIG. 1 is a cross-sectional view of a portion of the digestive tract in a human body with an anchor positioned in the pylorus and a sleeve attached to the anchor, according to some embodiments.

Persons skilled in the art will readily appreciate that various aspects of the present disclosure can be realized by any number of methods and apparatuses configured to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

The present disclosure relates to a system and methods to place and/or retrieve a device from within a body of a patient. Using the system and methods disclosed herein, a device may be implanted and/or retrieved from within the body of a patient endoscopically through the mouth, throat, stomach and intestine. Some examples relate to a system and method for placing and/or retrieving a device from within the gastrointestinal tract of a patient, such as within the pyloric antrum, pylorus, duodenum and/or the jejunum of a patient, when the device is loaded into a catheter.

In some instances, the system and methods disclosed herein may be used to position and/or retrieve a device, such as a gastrointestinal device, from within a stomach, intestine, pyloric antrum, pylorus, duodenum, or jejunum of a patient. The system and methods disclosed herein may be used to remove a device that has an expanded configuration and a collapsed configuration from within the gastrointestinal tract of a patient. For example, the system and methods disclosed herein may be used to position a device in a collapsed configuration within a patient and transition the device into the expanded configuration for retaining the device within the patient. The system and methods disclosed herein may be used to retrieve a device that is within a body of a patient in an expanded configuration by transitioning the device into a collapsed configuration and extracting the device from within the patient.

FIG. 1 shows a cross-sectional view of a portion of a human digestive tract 10, showing a stomach 16 and intestine 18. As shown in FIG. 1, a gastrointestinal device 100 may be positioned between the stomach 16 and the intestine 18. The gastrointestinal device 100 may be positioned within the pylorus 20 with portions of the gastrointestinal device 100 configured to be positioned within the pyloric antrum 22. The gastrointestinal device 100 may be positioned with certain portions of the gastrointestinal device 100 positioned within the stomach 16, the pylorus 20, and the intestine 18.

Figure 2:
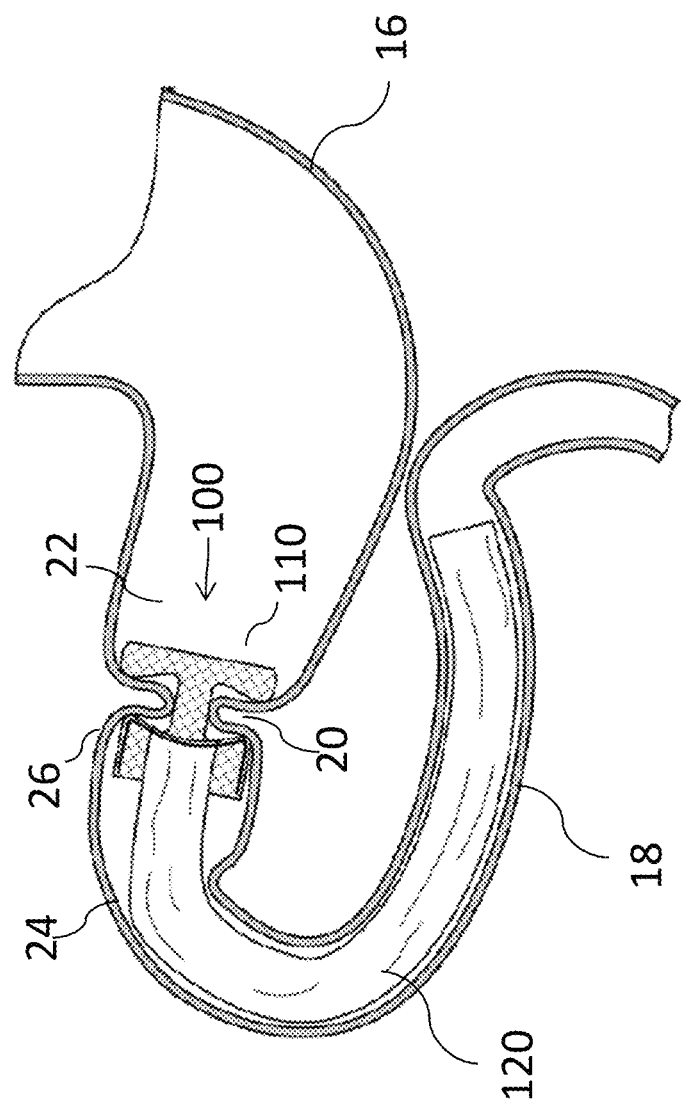
FIG. 2 is a cross-sectional view of a portion of the digestive tract in a human body with an anchor positioned in the pylorus and a sleeve attached to the anchor, according to some embodiments.

FIG. 2 is a cross-sectional view of a portion of the digestive tract in a patient showing the pylorus 20, pyloric antrum 22, duodenum 24, and duodenal bulb 26. FIG. 2 shows the gastrointestinal device 100 positioned between the stomach 16 and intestine 18. As shown in FIG. 2, the gastrointestinal device 100 may include an anchor 110 that holds or retains the gastrointestinal device 100 in place when positioned within the body of a patient, and a sleeve 120 attached to the anchor 110. The gastrointestinal device 100 may be an implant, a gastrointestinal implant, or a pyloric implant. Upon deployment, the anchor 110 of the gastrointestinal device 100 can transition to an expanded configuration and hold the gastrointestinal device 100 in place after implantation. In some instances, upon deployment, the sleeve 120 may be positioned within the intestine 18 of a patient. The sleeve 120 of the gastrointestinal device 100 that is shown within the intestine 18 may be an intestinal sleeve, a bypass sleeve such as an intestinal bypass sleeve, an intestinal liner, or a bypass liner. The sleeve 120 may be designed to be positioned in the duodenum 24 from the pylorus 20 to the ligament of treitz upon deployment. When deployed within a patient, the sleeve 120 is held in place in the intestine 18 by the anchor 110 of the gastrointestinal device 100 that is positioned within or on the pylorus 20.

Figure 3:
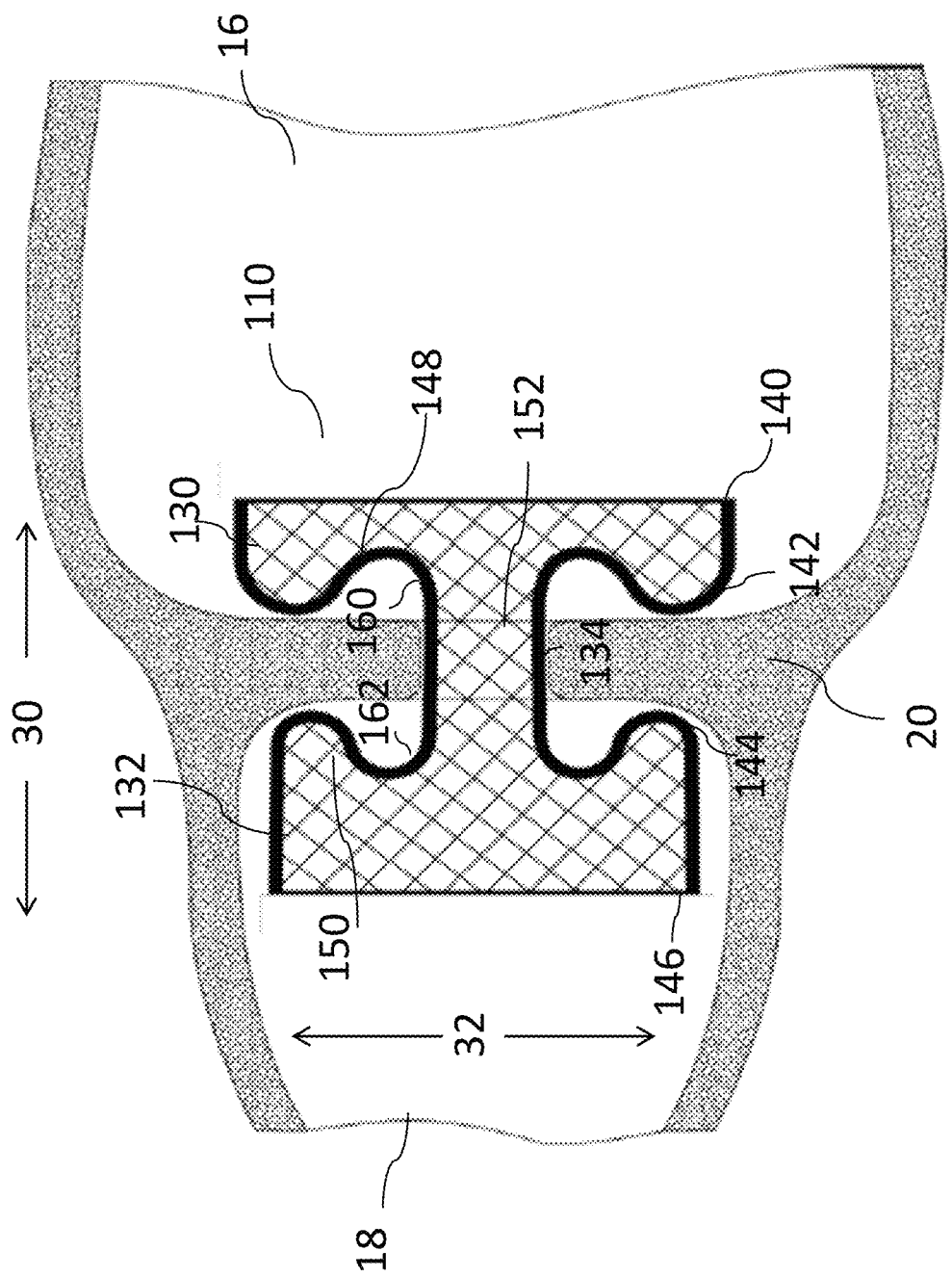
FIG. 3 is a cross-sectional view of a portion of the digestive tract in a human body with an anchor implanted in the pylorus, showing a structure of the anchor, according to some embodiments.

FIG. 3 shows a side view of the anchor 110. As shown in FIG. 3, the anchor 110 has an overall cylindrical shape with a length 30 in the longitudinal direction and a width 32 in the radial direction. In some embodiments, the anchor 110 defines a central longitudinal axis along the length 30 of the anchor 110. The anchor 110 has a proximal portion 130, a distal portion 132, and a neck portion 134.

In some embodiments, the proximal portion 130 is circular or disk shaped. In further examples, the proximal portion 130 has a proximal end 140, a distal end 142, and an outer wall in between. In some instances, the proximal end 140 and the distal end 142 define an overall cylindrical or tubular shape. In some embodiments, the proximal portion 130 includes a proximal flange wall 148. The proximal flange wall 148 is shaped as a disk and is attached to the distal end 142 of the proximal portion 130. The proximal flange wall 148 is oriented transverse to the central longitudinal axis of the anchor 110. The distal end 142 and/or the proximal flange wall 148 of the proximal portion 130 may be concave, for example, the proximal flange wall 148 may resemble a bowl. When positioned within a patient, the proximal portion 130 may be located on the side of the pylorus 20 that is in the stomach 16. In the expanded configuration, the proximal portion 130 may be open to allow chyme to enter. That is, the proximal portion 130 has an overall cylindrical shape with a proximal end 140 that is open and has a first diameter. The distal end 142 ends at the proximal flange wall 148 which tapers down to a diameter of the neck portion 134 that is smaller than the first diameter of the proximal end 140. The proximal flange wall 148 can be shaped with an angle in relation to the central longitudinal axis.

In some embodiments, the proximal portion 130 is circular or disk shaped. In some embodiments, the distal portion 132 is shaped as a flange. In further examples, the distal portion 132 may be shaped as a cylinder having a proximal end 144, a distal end 146 and an outer wall extending in between. The distal portion 132 includes a distal flange wall 150. The distal flange wall 150 is located on the proximal end 144 of the distal portion 132. The distal flange wall 150 is oriented transverse to the central longitudinal axis of the anchor 110. When positioned within a patient, in an expanded configuration, the distal portion 132 may be located in the duodenum. The distal portion 132 may define an opening at the distal end 146 that faces into the intestine 18.

The neck portion 134 comprises a first end 160, a second end 162 and a wall extending between the first and second ends 160, 162. The neck portion 134 may be shaped as a cylinder that extends between the proximal portion 130 and the distal portion 132. The neck portion 134 defines a through-lumen 152 that allows chyme to flow from the stomach 16 to the intestine 18. The neck portion 134 may be rigid to hold the pylorus 20 open or it may be compliant to allow the opening and closure of the through-lumen 152 with the pylorus 20. As used herein, the term "open" refers to a configuration that is expanded in the radial direction. That is the proximal portion 130, the neck portion 134, and/or the distal portion 132 may be open when expanded to increase the width 32.

The proximal flange wall 148 and distal flange wall 150 can be angled in relation to the neck portion 134 in order to provide certain spatial relationships to the pylorus 20 at particular locations. In some embodiments, both the proximal portion 130 and distal portion 132 are shaped to apply force F to the proximal and distal face of the pylorus 20, respectively. The effect of this force can help keep the implant in place, anchored across the pylorus 20. The anchor 110 may be formed form a braided wire structure. The braided wire structure may help position the anchor 110 within a patient. For example, the braided wire structure may provide structural support to the anchor 110 and help maintain the shape of the anchor 110.

As shown in FIG. 3, in some embodiments, the outer diameter of the distal portion 132 may define a gap or space between the distal portion 132 and the duodenum. In some embodiments, a gap or space between the outer diameter of the distal portion 132 and the duodenum may allow the anchor 110 to rotate or turn in a direction generally perpendicular to the central longitudinal axis of the anchor 110 or a longitudinal axis defined through the opening of the pylorus. If the anchor 110 is allowed to rotate after it is implanted in a patient, the distal portion 132 or the anchor 110 as a whole may undergo unwanted movement or deflection and in some cases become dislodged. Rotation or turning of the anchor 110 or the distal portion 132 may be inhibited by providing a distal portion 132 having a suitable length and diameter. A distal portion 132 having a suitable length may allow the distal portion 132 to contact the duodenum and prevent further rotation before the distal portion 132 or anchor 110 become deflected or dislodged. The length of the distal portion 132 may determine the degree of rotation the anchor 110 may undergo before contacting the duodenum.

The length and diameter of the distal portion 132 can be sized to prevent canting or tilting within a tubular anatomical structure such as the duodenum. In some embodiments, the length and the diameter of the distal portion 132 are sized such that upon rotation or canting of the anchor 110 away from the longitudinal axis, the distal end 146 of the distal portion 132 will make contact with the intestinal wall and therefore will resist migration of the anchor 110 within a patient. A suitable distal portion 132 length that may inhibit unwanted rotation, canting, or longitudinal deflection may be from about 10.0 mm to about 50.0 mm or any length in between. In some embodiments, the distal portion 132 may have a length that is sized in relation to the width of the distal portion 132. In some embodiments, the distal portion 132 may have a length that is sized in relation to the length of the proximal portion 130. For example, the length of the distal portion 132 may be the same length as the proximal portion 130. In some embodiments, the length of the distal portion 132 may be multiples of the length of the proximal portion 130. For example, the distal portion 132 may be one and a half, two times, three times, or greater, the length of the proximal portion 130.

In some embodiments, the diameter of the distal portion 132 may be from about 5.00 mm to about 60.0 mm, or any range in between, for example from about 20.0 mm to about 50.0 mm, or from about 30.0 mm to about 40.0 mm. For example, the distal portion 132 can have a length of roughly 18.0 mm and a diameter of 35.0 mm, to ensure the structure can remain positioned within a tubular anatomic structure such as the duodenal bulb with a diameter of about 40.0 mm. An anchor 110 has been formed with the diameter of the distal portion 132 of about 35.0 mm in diameter.

In some embodiments, the diameter of the proximal portion 130 is about 10.0 mm to about 75.0 mm, or any range in between, for example from about 25.0 mm to about 60.0 mm, and from about 40.0 mm to about 55.0 mm. In one example, an anchor 110 was formed with the diameter of the proximal portion 130 of about 40.0 mm.

In some embodiments, the diameter of the neck portion 134 may be from about 2.0 mm to about 30.0 mm, or any range in between, for example, from about 5.0 mm to about 30.0 mm, and from about 10.0 mm to about 20.0 mm. In one example, an anchor 110 was formed with the diameter of the neck portion 134 of about 15.0 mm.

In some embodiments, the length of the neck portion 134 may be approximately the width of a patient's pylorus. In some embodiments, the length of the neck portion 134 may be longer than the width of a patient's pylorus to provide a gap between the proximal flange wall 148, the distal flange wall 150 and the pylorus 20. In some embodiments, the neck portion 134 may be sized to allow the proximal flange wall 148 and the distal flange wall 150 to contact the pylorus 20.

The overall length of the anchor 110 can be from about 10.0 mm to about 100.0 mm, but varying sized anchors may be formed, depending on a patient's anatomy or anatomical fit. In some embodiments, the anchor 110 length may be from about 10.0 mm to about 100 mm, from about 25.0 mm to about 75.0 mm, from about 40.0 mm to about 60.0 mm, or any length within these ranges. In some instances the anchor 110 may be between about 45.0 mm and 55.0 mm long. In one example, an anchor 110 that was formed was about 50.0 mm long. In some embodiments, the anchor 110 is compressible in diameter and the overall diameter can be reduced to about 5.00 mm to about 10.0 mm in diameter, for example to allow the anchor 110 to be loaded into a catheter.

Figure 4:
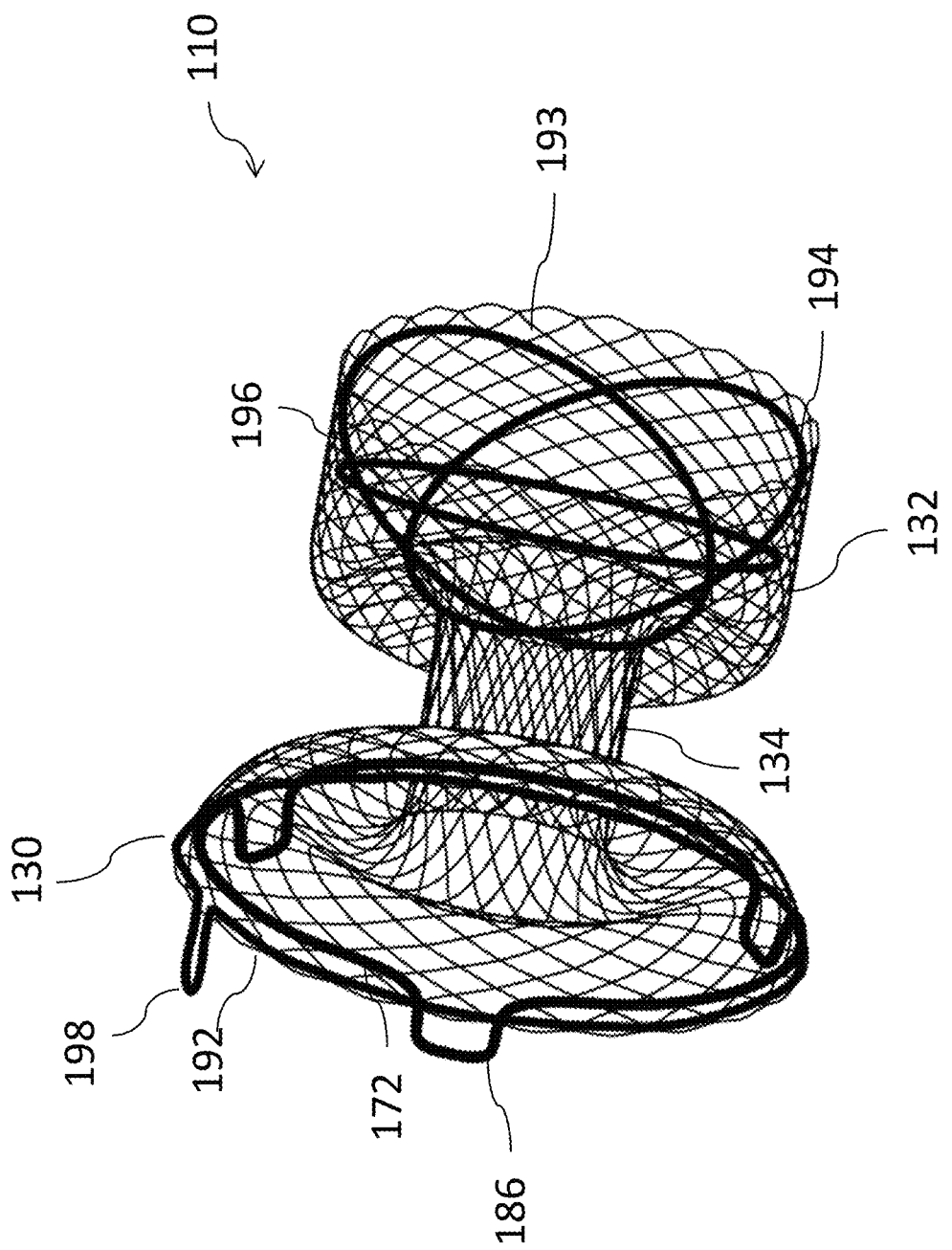
FIG. 4 is a schematic of an anchor and sleeve, according to some embodiments.

FIG. 4 is a perspective view of the anchor 110. In some embodiments, the anchor 110 may be self-expandable. In some embodiments, the anchor 110 includes a structural element contained within the braided wire structure. As shown in FIG. 4, in some embodiments, the anchor 110 has a distal structural element 196. The distal structural element 196 may be comprised of rings 193, 194 attached to the distal portion 132 and/or the neck portion 134. The distal structural element 196 can be made from a metal such as Nitinol (nickel-titanium alloy), a nickel-cobalt base alloy such as that sold under the tradename MP35N®, a cobalt alloy such as Alloy L605, a cobalt-chromium-nickel-molybdenum alloy such as that sold under the tradename Elgiloy®, stainless steel, or from a plastic such as PET, PEEK, apolyoxymethylene such as that sold under the tradename Delrin® or any other suitable material. The distal structural element 196 can be made from superelastic Nitinol wire formed into a suitable shape. In an exemplary embodiment, a distal structural element 196 was formed from three rings of Nitinol wire. If the distal structural element 196 is desired with a certain rigidity or stiffness, the size and material that the distal structural element 196 is made from can be used to control these properties. For example, Nitinol wire can be used to form stiffening elements with a suitable compressive and expansive strength as a function of the diameter of the wire used to make the distal structural element 196.

The distal structural element 196 may be formed of material having a thickness in the range from about 0.010 inch to about 0.040 inch, or any range in between such as from about 0.015 inch to about 0.030 inch, from about 0.020 inch to about 0.025 inch. In an example embodiment, a distal structural element 196 comprised of a plurality of rings was formed from material having a thickness of about 0.020 inch, or about 0.51 mm. Generally, each of the rings 193, 194 that may form the distal structural element 196 have the same diameter which is from about 1.0 inch to about 2.0 inches, and any range within such as from about 1.2 inches to about 1.8 inches, and from about 1.3 inches to about 1.7 inches. In an example embodiment, the distal structural element 196 comprised material formed into rings 193, 194, each having a diameter of about 1.38 inches, or about 35.0 mm.

As shown in FIG. 4, the rings 193, 194 of the distal structural element 196 are arranged around the distal portion 132 and are attached to the distal portion 132, such as by being integrally woven into the flange material. The rings 193, 194 of the distal structural element 196 are attached by first weaving the rings 193, 194 though the braided structure of the distal portion 132 and then the wire ends can be inserted into a connection sleeve and crimped or welded.

As shown in FIG. 4, in some embodiments, the anchor 110 may have a proximal structural element 172 attached to the proximal portion 130. The proximal structural element 172 may be a compression biasing element, such as a spring. The proximal structural element 172 may be constructed as a substantially circular frame having nodes 186. The proximal structural element 172 may be constructed from the same material that forms the distal structural element 196. The proximal structural element 172 may also provide structural support to the proximal portion 130. For example, the proximal structural element 172 generally has an overall frame that is compressible, yet also is rigid. The proximal structural element 172 may impart additional radial strength to the proximal portion 130 and help keep the proximal end 140 of the proximal portion 130 open. The proximal structural element 172 can be shaped to bias the direction of collapse of the anchor 110 for removal from a patient and for loading the device onto a delivery catheter for delivery within a patient.

Figure 5:
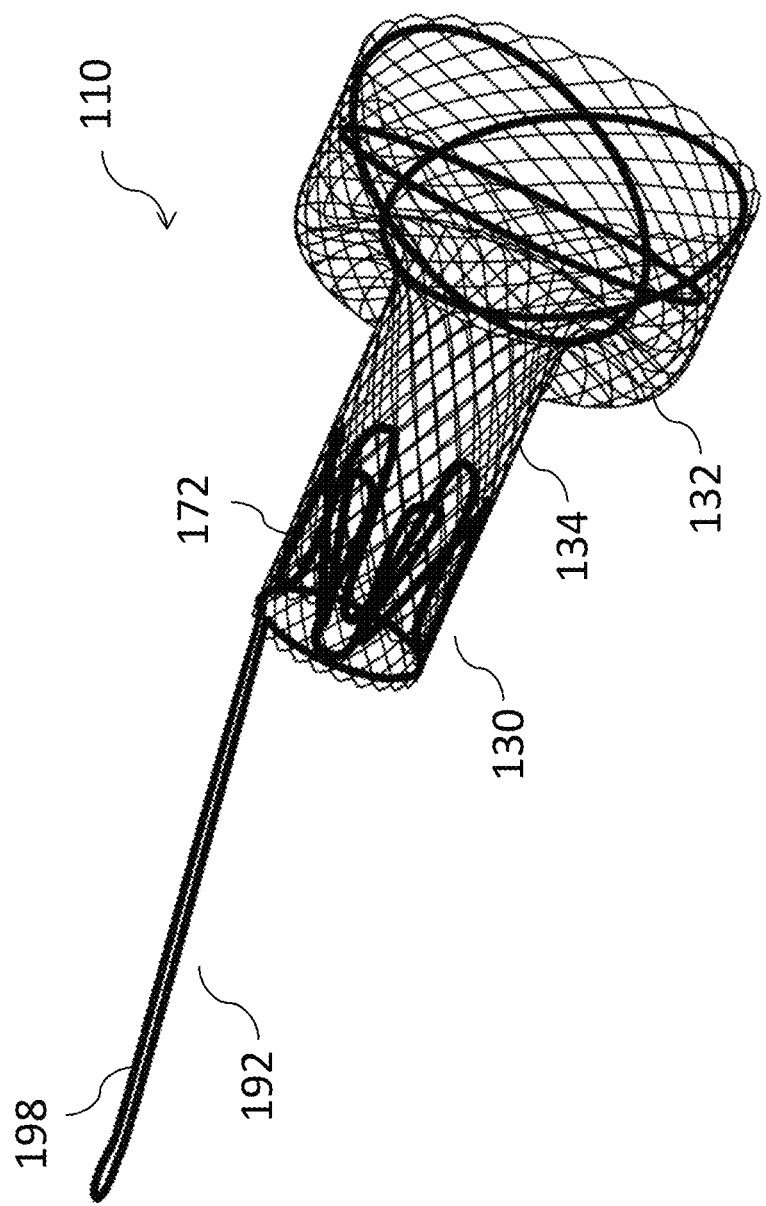
FIG. 5 is a schematic of an anchor and sleeve, according to some embodiments.

As shown in FIG. 4, in some embodiments, the anchor 110 may include a drawstring 192. The drawstring 192 is attached to the proximal portion 130. The drawstring 192 can be attached to the proximal portion 130 by weaving the drawstring 192 through the material of the proximal portion 130. As shown in FIG. 5, the drawstring may be weaved through the material of the proximal portion and have a portion of the drawstring forming a loop 198. For example, the drawstring 192 may be constructed from a string or suture that is weaved through alternating cells in the braided wire structure of the anchor 110. The loop 198 allows the drawstring 192 to be attached to a retraction tool, for example, to a hook or a clamp. In some embodiments, the drawstring 192 is a suture that is weaved through the proximal portion 130. The drawstring 192 may be a separate structure from the proximal structural element 172. The drawstring 192 may be constructed from a suture material and may comprise a thin wire or cable.

FIG. 5 shows the proximal portion 130 of the anchor 110 in a collapsed configuration. The drawstring 192 can be used to elastically contract the anchor 110 by connecting at least one loop 198 to a removal device and by drawing into a sheath. In some embodiments, the drawstring 192 allows the proximal portion 130 to collapse to the diameter of the neck portion 134. The drawstring 192 may also be attached to different portions of the anchor 110 such as in the neck portion 134 or the distal portion 132. The anchor 110 may also have multiple drawstrings to collapse different portions of the anchor 110 sequentially during implantation or retrieval.

FIG. 5 shows the proximal portion 130 in a collapsed configuration, such as after the drawstring 192 has been pulled. In some embodiments, the anchor 110 may be may be configured to collapse into a suitably narrower size. For example, the anchor 110 may be collapsed into a narrower diameter for placement within or removal from a patient. In some embodiments, the anchor 110 can be collapsed by pulling the drawstring 192, for example by pulling the loop 198. The loop 198 of the drawstring 192 may be pulled away from the anchor 110, collapsing the proximal structural element 172.

Figure 6:
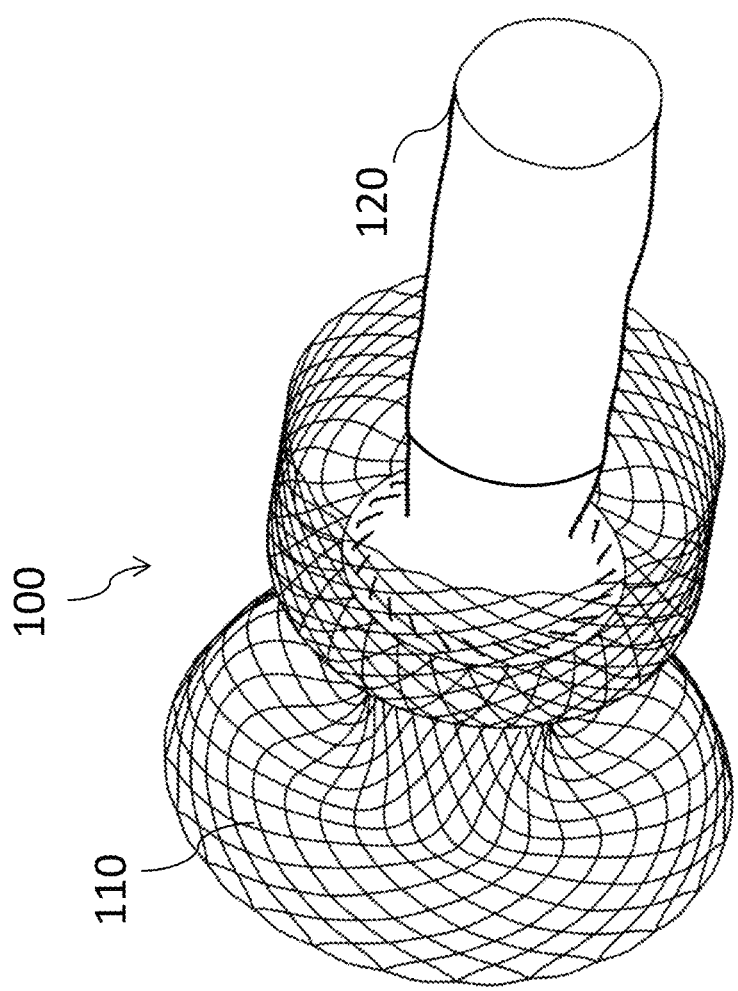
FIG. 6 is a schematic of an anchor, according to some embodiments.
Figure 7:
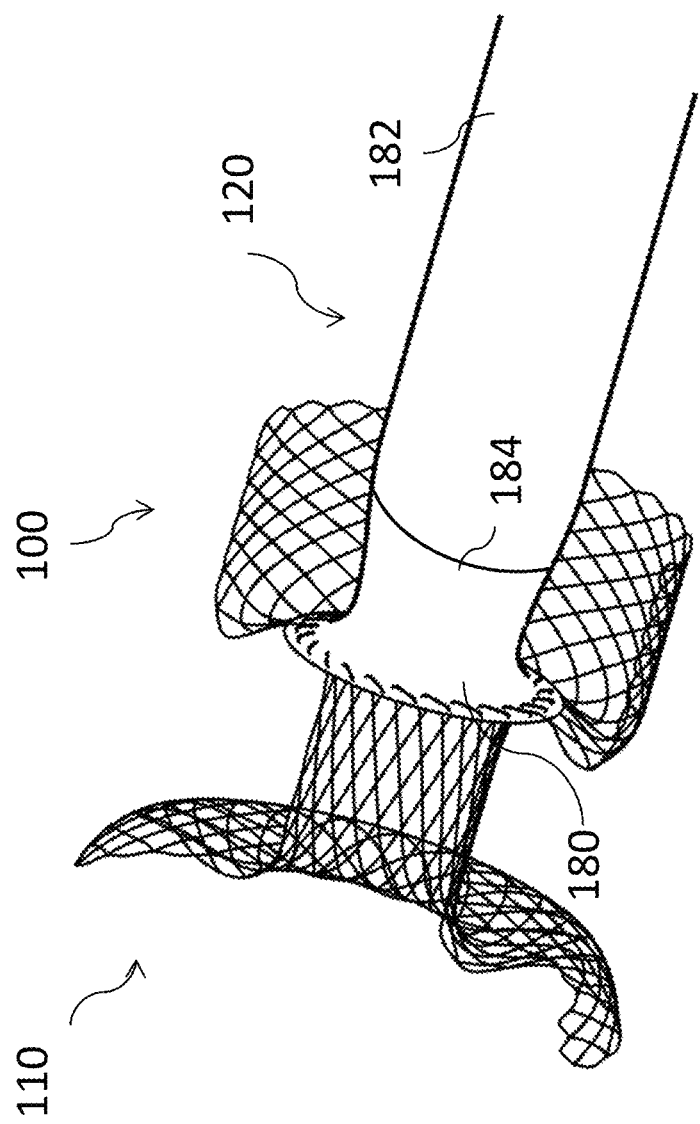
FIG. 7 is a schematic of an anchor in a collapsed configuration, according to some embodiments.

FIG. 6 is a perspective view of the gastrointestinal device 100 with the sleeve 120 attached to the anchor 110. FIG. 7 is a perspective view of the gastrointestinal device 100 with the sleeve 120 attached to the anchor 110 to illustrate additional features. As shown in FIG. 7, an overall schematic of a sleeve 120 includes a mouth 180, a sleeve body 182, and a neck 184. The diameter of the sleeve body 182 is generally sized to correspond to the diameter of the intestine of a human. The diameter of the sleeve 120 decreases at the neck 184 to be consistent with the inner diameter of the anchor 110. This change in diameter also helps to prevent sleeve eversion in which the sleeve 120 folds back into itself in response to an increase in pressure applied to the outside of the sleeve 120. According to various embodiments, the sleeve body 182 has a wall thickness of between about 0.001 inches and about 0.015 inches. The neck 184 of the sleeve 120 may be thicker than the sleeve body 182, for example, the neck 184 may have a wall thickness from about 0.001 inches to about 0.005 inches thick, to provide a second mechanism to prevent sleeve eversion. When the sleeve 120 is subjected to an external pressure, the thicker neck 184 collapses and inhibits the sleeve 120 from folding back on itself. This mechanism may essentially create a duck-bill valve.

The sleeve 120 may have a length from about 1.0 inch to about 2.0 inches in length up to several feet in length. In some embodiments, the sleeve 120 is sized to extend past the length of the duodenum up to the ligament of treitz when deployed. While various embodiments disclosed herein describe the sleeve 120 as extending into the duodenum. In general, it is also contemplated that the sleeve 120 has a length sufficient to allow it to extend partially or fully into the jejunum. A suitable length of the sleeve 120 may be dictated by the required mechanism of action. In some instances, an effective sleeve length is one that allows it to reach the proximal jejunum. This location corresponds to the location of the ligament of treitz. The length of the sleeve is determined based on the desired clinical outcome. In some examples, a sleeve roughly 2 feet in length is sufficient to modify the transport and absorption of food and organ secretions within the intestine, leading to remission of type 2 diabetes.

The sleeve 120 may be made from a thin wall of polymer material such as silicone, polyurethane, polytetrafluoroethylene, fluorinated ethylene propylene, polyethylene, expanded polytetrafluoroethylene (ePTFE) or other suitable material. In exemplary embodiments, the wall thickness of the sleeve 120 may be from about 0.0006 inches to about 0.010 inches thick. The sleeve 120 may be made by extrusion, into a tubular form or a lay flat tubing, dip coated from a liquid solution, powder coated from fine particles of polymer or paste extruded and then stretched as is the case with ePTFE.

In some embodiments, the gastrointestinal device 100 may be endoscopically implanted within, or retrieved from the pylorus 20 with the anchor 110 in the collapsed or compressed configuration. As used herein, a closed, compressed, or collapsed configuration refers to the anchor 110 having the diameter of at least one of the proximal portion 130 or the distal portion 132 reduced in the direction of the width 32 (shown in FIG. 3) of the anchor 110. After implantation, the anchor 110 may be released and assume an open or expanded configuration. Once in the open or expanded configuration, the anchor 110 generally anchors itself to remain with at least a portion of the gastrointestinal device 100 within the pylorus 20.

Figure 8:
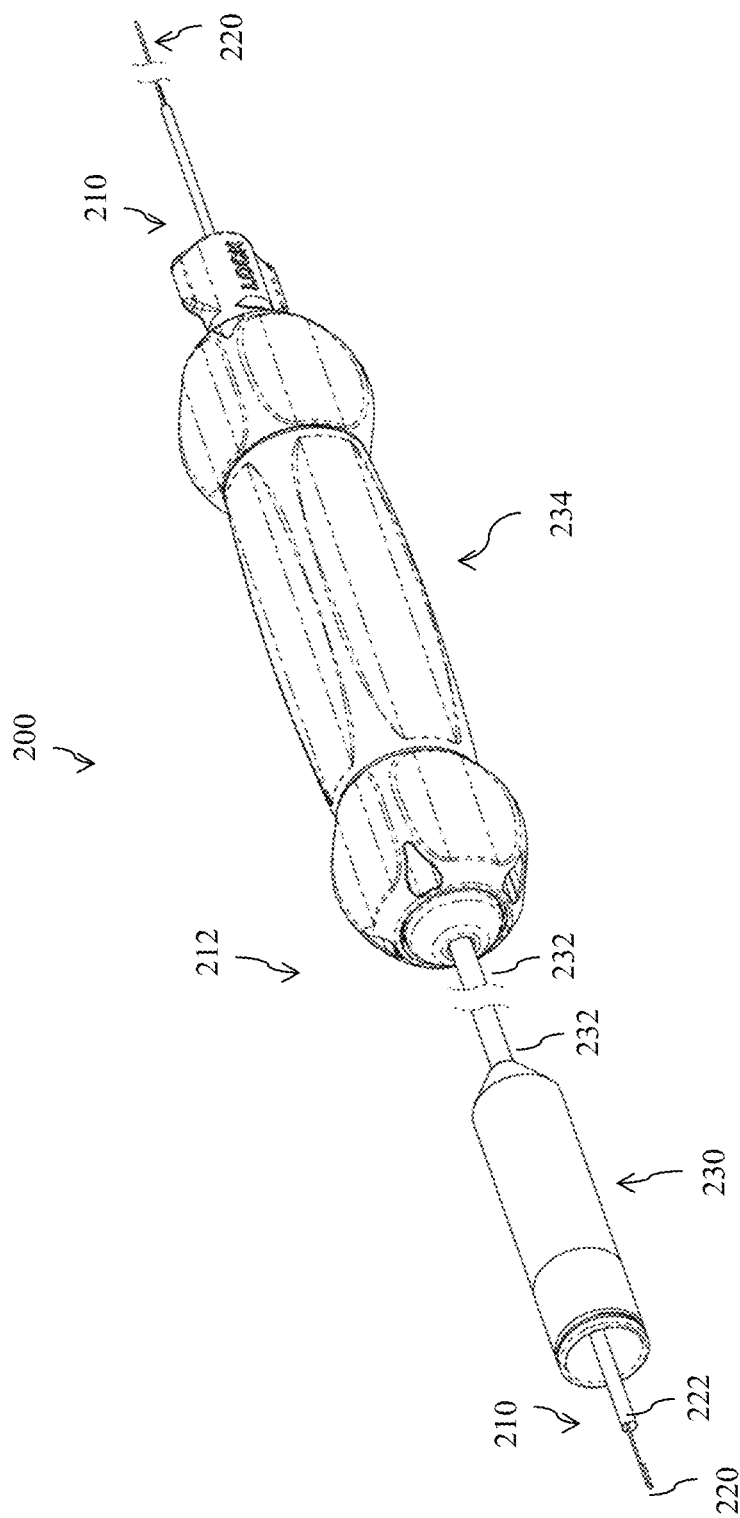
FIG. 8 is an overall schematic of a retrieval system, in accordance with various aspects of the present disclosure.

FIG. 8 is a perspective view of an overall schematic of a retrieval device 200. In some embodiments, the retrieval device 200 may be used as an extractor, for example to remove an anchor, a stent, or any foreign body such as a medical device from within the body of a patient. The retrieval device 200 may be used for removing an anchor 110 that is expandable and a sleeve 120 from the body of a patient. As described herein the retrieval device 200 is described with respect to retrieving or extracting a gastrointestinal device 100, such as the gastrointestinal device 100 previously disclosed in FIGS. 1 to 7, from the stomach or intestine of a patient. However, it is envisioned that the system and methods described herein may be used to retrieve or extract other foreign bodies from within a patient. For example, certain components may be altered or added to allow the retrieval device 200 to capture and extract foreign objects of various shapes and materials from within a patient.

As shown in FIG. 8, the retrieval device 200 includes a hook assembly 210, and a capsule assembly 212. As shown, the capsule assembly 212 includes a capsule 230, a capsule shaft 232, and a handle 234. In some embodiments, the hook assembly 210 includes a hook cable 220 and a hook sheath 222. In some embodiments, the hook assembly 210 comprises a hook cable 220 without the hook sheath 222. In some embodiments, when in use, the hook cable 220 is received within the hook sheath 222 to form the hook assembly 210. In a deployment method, a first portion of the retrieval device 200, such as a section of the hook assembly 210 and the capsule assembly 212 may be configured to be inserted into the body of a patient, with a second portion of the retrieval device 200 such as the handle 234 remaining outside the patient.

FIGS. 9A and 9B are side views of schematics of a hook assembly 210 that may be used with the retrieval device 200 of FIG. 8. In some examples, the hook assembly 210 comprises the hook cable 220 and the hook sheath 222. In further examples, the hook assembly 210 may comprise the hook cable 220 without the hook sheath 222. In some examples, the hook cable 220 and the hook sheath 222 may be formed as a single unitary body. For example, the hook cable 220 and the hook sheath 222 may be joined together to form a single unitary and form the hook assembly 210. In further examples, the hook cable 220 and the hook sheath 222 may be formed as two separate devices which are joined together to form the hook assembly 210. As shown in FIGS. 9A and 9B, the hook assembly 210 has the hook cable 220 and a hook sheath 222. In some embodiments, the hook assembly 210 fits within the working channel of a standard endoscope. In some embodiments, the hook assembly 210 fits within the working channel of a standard endoscope that has an inner diameter of about 1.4 mm, about 1.6 mm, about 1.8 mm, or about 2.2 mm, about 2.4 mm or about 2.6 mm, or between any pair of the foregoing values, although additional sizes are contemplated. For example, the hook assembly 210 may be suitably sized to be inserted within the working channel of an endoscope that has about a 2.8 mm inner diameter. In one example, a hook assembly 210 has been formed to fit in an endoscope channel having an inner diameter of 2.0 mm.

As shown in FIG. 9A, the hook cable 220 has a first end 310, a second end 312 and a length in between and defines a longitudinal axis 314. In examples of the hook assembly 210 having the hook cable 220 without the hook sheath 222, the first end 310 of the hook cable 220 may define the first end of the hook assembly 210. The first end 310 of the hook cable 220 includes an attachment feature 340 such as a grappling mechanism, a hook, a clasp, an arm, a basket, or a plurality of fingers for attaching to or grappling an object such as a medical device or foreign body. In some embodiments, the attachment feature 340 defines the first end 310 of the hook cable 220. The attachment feature 340 may have a length 344 and a width 346 sized and shaped to correspond to particular suitable dimensions. For example, the attachment feature 340 may have a length 344 suitable for attaching to and retaining a drawstring, such as the drawstring 192 previously discussed in FIGS. 4 and 5. The width 346 may be sized to allow the attachment feature 340 to fit within the hook sheath 222. That is, the width 346 may be sized to allow the entire attachment feature 340 to fit within the first inner diameter 326 and the second inner diameter 370 of the hook sheath 222. The attachment feature 340 may be used to capture and/or lock a drawstring and pull it into the hook sheath 222.

As shown in FIG. 9A, the hook assembly 210 includes a hook cable stop 360 positioned along the hook cable 220. In some embodiments, the hook cable stop 360 may define an outer diameter 362 that is greater than the first inner diameter 326 of the hook sheath 222. In some embodiments, the hook cable stop 360 may have an outer diameter 362 such that the hook cable stop 360 is inhibited from entering the hook sheath 222.

As shown in FIG. 9A, in some embodiments, the length of the hook cable 220 is greater than the length of the hook sheath 222. The hook cable 220 is sized to be received within the hook sheath 222. In some embodiments, the hook cable 220 may be inserted into the hook sheath 222 by inserting the first end 310 having the attachment feature 340 into the second end 322 of the hook sheath 222. The hook cable 220 may be advanced along the inside of the hook sheath 222 until the first end 310 of the hook cable 220 such as the attachment feature 340 extends out the first end 320 of the hook sheath 222.

As shown in FIG. 9B, the hook sheath 222 has a first end 320, a second end 322, and a length in between along the longitudinal axis 324 of the hook sheath 222. The hook sheath 222 may comprise a flexible tube with an inner surface 378 defining a lumen, and an outer surface 376. The hook sheath 222 has a first inner diameter 326 and a first outer diameter 328 at the first end 320. The hook sheath 222 may have a second inner diameter 370 and a second outer diameter 372 at the second end 322. In some embodiments, the second inner diameter 370 and second outer diameter 372 may be the same as the first inner diameter 326 and first outer diameter 328 respectively. In some embodiments, the first inner diameter 326 of hook sheath 222 is sized such that an attachment feature 340 or other retraction tool can be received within the first inner diameter 326. For example, the first inner diameter 326 and second inner diameter 370 of the hook sheath 222 may be sized such that the attachment feature 340 can be inserted into the hook sheath 222.

In some embodiments, the hook sheath 222 is constructed as a flexible tube that may bend or curve at an angle to the longitudinal axis 324. The hook sheath 222 may be flexible in a direction perpendicular to the longitudinal axis 324, yet incompressible in a longitudinal direction along the longitudinal axis 324. For example, the hook sheath 222 may be constructed as a closely packed coil made of a resilient material such as metal or plastic. The coil may bend or flex in a direction perpendicular to the length of the coil, such as along the longitudinal axis 324. The coil being closely packed may prevent it from compressing in the direction of the longitudinal axis 324, and the coil may be resilient to prevent the hook sheath 222 from extending or stretching along the longitudinal axis 324 of the hook sheath 222. That is, the hook sheath 222 may be minimally compressible such that the hook sheath 222 is maintained at a set length by the hook sheath material construction.

The hook sheath 222 may be coated on the inner surface 378 and/or the outer surface 376. For example, if the hook sheath 222 is constructed as a coil, a coating may cover or fill in the spaces between turns of the coil and provide a smooth consistent surface along the hook sheath 222 inner surface 378 and outer surface 376. In some embodiments, the hook sheath 222 may have a covering that creates a smooth consistent surface and may prevent the coils from opening spaces. Material for a coating may be chosen to reduce friction along the hook sheath 222 inner surface 378 and outer surface 376. For example, the outer surface 376 of the hook sheath 222 may be provided with a coating that is suitable for reducing friction with the tissue of a patient, such as esophageal or stomach tissue. The hook sheath 222 inner surface 378 may be provided with a coating that is suitable for reducing friction with additional features of the retrieval device 200 that may be inserted within the hook sheath 222, such as the hook cable 220. In some embodiments, the hook sheath covering may include a smooth plastic or polymer coating such as fluorinated ethylene propylene (FEP) or a polytetrafluoroethylene such as that sold under the tradename Teflon™. In some embodiments, the hook sheath covering may be made from a material that can be melted and reflowed, such as thermoplastics, or thermoplastic elastomers. For example, the hook sheath covering may be made from polyether block resins such as that sold under the tradename Pebax®.

As shown in FIG. 9A, the hook assembly 210 also includes a hook cable lock 350 positioned along the hook cable 220. In some embodiments, such as examples of the hook assembly 210 having the hook cable 220 without the hook sheath 222, the hook assembly 210 may be formed without a hook cable lock 350. In examples of the hook assembly 210 that include the hook cable 220 and the hook sheath 222, the hook cable 220 and the hook sheath 222 may be formed as two separate devices which are joined together. For example, the hook cable lock 350 may be configured to lock the hook cable 220 in longitudinal relation to the hook sheath 222. The hook cable lock 350 may include an arrestment mechanism that prevents the hook cable 220 from moving in relation to the hook sheath 222 along the longitudinal axis 324 of the hook sheath 222. As one example, the hook cable lock 350 may comprise a screw thread that may engage with a corresponding screw thread on the hook sheath 222. In a further example, the hook cable lock 350 may include tabs or fingers (not shown) within the inner diameter of the hook sheath 222 that deform when a portion of a locking sheath 354 is inserted. The fingers may be configured to hold the hook sheath 222 and the locking sheath 354 together in a first configuration and may incorporate features to defeat the lock and allow the hook sheath 222 and the locking sheath 354 to be released from one another. In another example, the hook cable lock 350 may comprise a holding mechanism such as a collet, chuck, or tabs to impart a compressive force on the hook cable 220 to prevent movement of the hook cable 220.

FIGS. 9A and 9B show an example embodiment of a hook cable lock 350 that may be configured to lock the hook cable 220 and the hook sheath 222 together to form the hook assembly 210. As shown, the hook cable 220 may comprise multiple wires 352 positioned along a section of the length of the hook cable 220. The multiple wires 352 are joined together near the second end 312 of the hook cable 220. The hook cable lock 350 may have an outer diameter 362 that is greater than the first inner diameter 326 of the hook sheath 222. In some embodiments, the hook cable lock 350 may include a locking sheath 354 having an outer portion 356 that surrounds the outer circumference of the multiple wires 352 and has a tine 358 that extends between two or more of the multiple wires 352 and attaches to the outer portion 356 of the locking sheath 354. The outer portion 356 of the locking sheath 354 may have an inner diameter that is larger than the outer circumference of the multiple wires 352, for example, both with and without the tine 358 inserted between two or more of the multiple wires 352. The tine 358 of the locking sheath 354 may have a suitable width such that when the tine is positioned between two or more of the multiple wires 352, two or more of the multiple wires 352 separate a certain distance from each other. With the tine 358 positioned between two or more of the multiple wires 352, the multiple wires 352 have an overall outer circumference that is greater than the inner diameter of the locking sheath 354. When the tine 358 of the locking sheath 354 is inserted between the multiple wires 352, the multiple wires 352 are separated a distance from each other that results in the multiple wires 352 having a total outer diameter 362 greater than the second inner diameter 370 of the hook sheath 222, at least along a portion of the hook cable 220 adjacent the tine 358. The locking sheath 354 may be moved along the hook cable 220 toward the second end 322 of the hook sheath 222. As the locking sheath approaches the hook sheath 222 second end 322, the tine 358 separates the multiple wires 352 to create an overall diameter greater than the second inner diameter 370 of the hook sheath 222. This may prevent the hook cable 220 from moving further into the hook sheath 222.

As shown in FIG. 9B, the locking sheath 354 may be located along the length of the hook cable 220 outside the hook sheath 222. A portion of the length of the hook cable 220 comprises two wires, and the hook cable lock 350 may advance or retract along the length of the hook cable 220 outside the hook sheath 222. The tine 358 of the hook cable lock 350 is in between the two wires and the outer portion 356 is around the two wires. With the tine 358 of the hook cable lock 350 in between the two wires, the hook cable 220 is expanded such that the outer diameter of the hook cable 220 is wider than the second inner diameter 370 of the hook sheath 222. In this configuration, the hook cable 220 is prevented from moving longitudinally into the hook sheath 222 into the second end 322. According to some embodiments, the features of the locking mechanism for locking the hook cable may be of the type described in European Patent Patent No. 1832250, which is hereby incorporated by reference.

In some embodiments, the hook cable 220 may be made from material having a suitable tensile strength that is also biocompatible. For example, the hook cable 220 may be made of metal or metal alloys such as stainless steel, Nitinol, MP3 5N (nickel-cobalt-chromium-molybdenum alloy), formed into a single cable, or as strands. In some embodiments, the hook cable 220 may include composite materials, polymers, or plastics to impart additional material properties. The hook cable 220 may have an outer diameter that is from about 0.020 inches wide to a width that corresponds to the inner diameter of the hook sheath. In an example embodiment, a hook cable was made that was 0.025 inches in diameter.

In some embodiments, the locking sheath 354 and/or the hook cable stop 360 may be made from any suitable material that is incompressible in the longitudinal direction yet flexible at an angle to the longitudinal axis, such as in the transverse direction. In some embodiments, the locking sheath 354 and/or the hook cable stop 360 may be made from a material that is rigid and can be shaped to fit within the hook sheath 222. In some embodiments, the locking sheath 354 and/or the hook cable stop 360 may be made from the same material as the hook cable 220. The locking sheath 354 and/or the hook cable stop 360 may be made from steel. The locking sheath 354 and/or the hook cable stop 360 may include a coating such as a plastic or polymer coating. In some embodiments, the locking sheath 354 and/or the hook cable stop 360 may be color coded for ease of use.

FIG. 9C shows a side view of a hook 341 that may be used with the hook assembly 210 shown in FIGS. 9A and 9B. As shown, the hook 341 includes a shank 342 and a point 343. The hook 341 may include a gap 345 formed by and between the shank 342 and the point 343. The hook 341 may be shaped such that an object can be positioned within the gap 345. The hook 341 may include a bend 349 along a portion of the shank 342. The shank 342 and the point 343 may be configured such that an object positioned within the gap 345 is retained on the hook 341. For example, the point 343 may be positioned near the shank 342, and may be in contact with the shank 342. When the hook 341 is deployed, the point 343 may be used to retain an object within the gap 345, and the point 343 and shank 342 may be shaped to inhibit the object from being released from the hook 341. The shank 342, the point 343, and the gap 345 may define a profile 347 of the hook 341. In some examples, profile 347 of the hook 341 may be sized such that the hook 341 may be inserted into a lumen of an endoscope. In a further example, the profile 347 of the hook 341 may have a suitable size and/or shape to be inserted within the hook sheath 222 shown in FIGS. 9A and 9B. The hook 341 may define a profile 347 that is from about 1.0 mm, about 1.4 mm, or about 1.8 mm, to about 2.2 mm, about 2.6 mm or about 3.0 mm wide, or between any pair of the foregoing values, although additional sizes are also contemplated.

Figure 10:
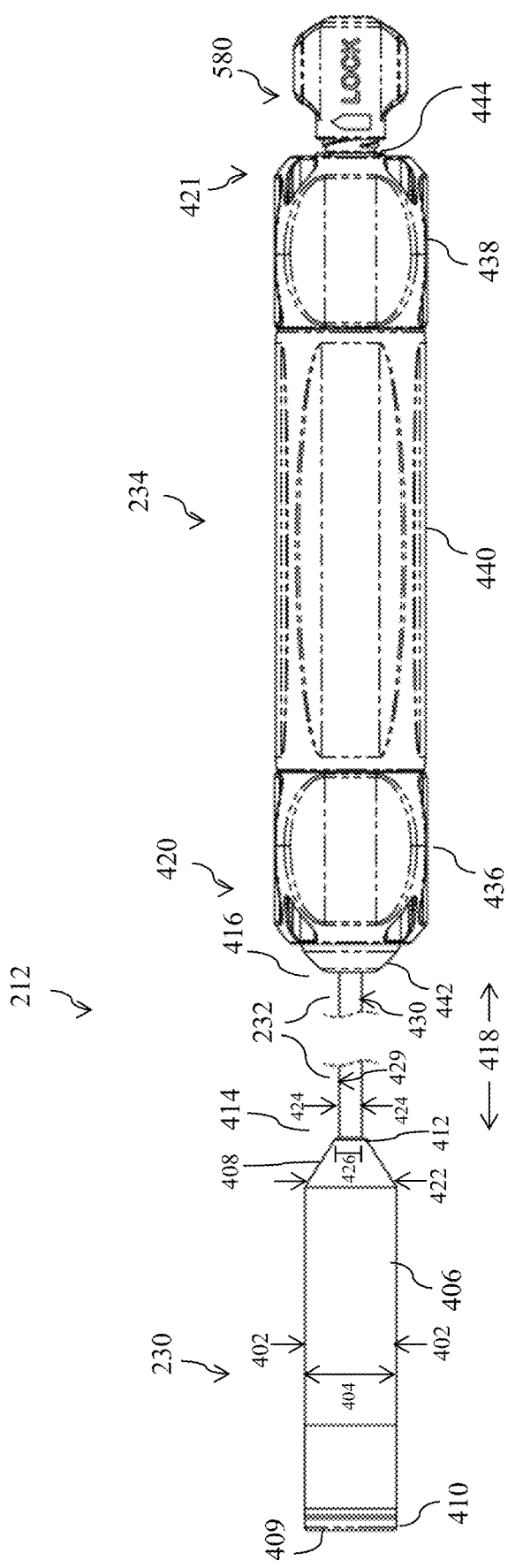
FIG. 10 is an overall schematic of a capsule assembly, in accordance with various aspects of the present disclosure.

FIG. 10 shows a side view of the capsule assembly 212. As shown in FIG. 10, the capsule assembly 212 includes a capsule 230, a capsule shaft 232, and a handle 234. The capsule 230, the capsule shaft 232, and the handle 234 are attached to each other to form the capsule assembly 212. The handle 234 has a first end 420 and a second end 421. The capsule shaft 232 has a first end 414, a second end 416 and a length 418 in between. In some embodiments, the capsule 230 has a first end 410 and a second end 412. The first end 410 defines an opening 409 to the inside of the capsule 230. The first end 414 of the capsule shaft 232 is attached to the second end 412 of the capsule 230. The first end 420 of the handle 234 is attached to the second end 416 of the capsule shaft 232.

The capsule 230, the capsule shaft 232, and the handle 234 may each have an outer diameter. The capsule 230, the capsule shaft 232, and the handle 234 may each have an inner bore defining an inner diameter. After assembly, the capsule 230, the capsule shaft 232, and the handle 234 may be assembled with the inner bore of each of the capsule 230, the capsule shaft 232, and the handle 234 adjacent and in series to form a continuous inner bore along the length of the capsule assembly 212.

In some embodiments, the handle 234 has a first control knob 436 located at the first end 420, a second control knob 438 located at the second end 421, and a central core 440. In some embodiments, the handle 234 includes a third sheath 444, nested within a second sheath 442, which is nested within the central core 440. The central core 440 forms an outer sheath to the handle 234. In some embodiments, the handle 234 may include a hook assembly lock 580. In some embodiments, the handle 234 may be an extraction mechanism, a withdrawal mechanism, or a tensioning mechanism. In some embodiments, the handle 234 may have a contracted or compressed configuration and an extended or elongated configuration.

As shown in FIG. 10, the capsule shaft 232 is generally shaped as an elongated tube having an inner diameter 426 and an outer diameter 424. In some embodiments, the capsule shaft 232 inner diameter 426 and outer diameter 424 vary at certain points along the length 418 of the capsule shaft 232. The outer diameter 424 and/or inner diameter 426 of the capsule shaft 232 at the first end 414 may be sized to correspond with the inner diameter 404 and outer diameter 422 of the capsule 230 at the second end 412. In some embodiments, the capsule shaft 232 is constructed as a flexible tube that may bend or curve at an angle to or relative to the longitudinal axis of the capsule shaft 232. The capsule shaft 232 may be incompressible in the longitudinal direction along the length 418 of the capsule shaft 232. For example, the capsule shaft 232 may be constructed as a closely packed coil made of a resilient material such as metal or plastic. The coil may bend or flex in a direction perpendicular to the length of the coil. The coil being closely packed may be prevented from compressing in the longitudinal direction, and the coil may be resilient to prevent the capsule shaft 232 from extending or stretching along the length 418. That is, the length 418 of the capsule shaft 232 is maintained at a set length by the construction of the capsule shaft 232.

The capsule shaft 232 may be coated on the inner surface 429 and/or the outer surface 430. In some instances, if the capsule shaft has spaces along the inner surface 429 and/or the outer surface 430, such as if the capsule shaft 232 is constructed as a coil, a coating may cover or fill in the spaces between turns of the coil and provide a smooth consistent surface along the inner surface 429 and/or outer surface 430 of the capsule shaft 232. The coating may be chosen to reduce friction along the inner surface 429 and outer surface 430 of the capsule shaft 232 with other objects. For example, the outer surface 430 of the capsule shaft 232 may be provided with a coating that is suitable for reducing friction with the tissue of a patient, such as esophageal or stomach tissue. The inner surface 429 of the capsule shaft 232 may be provided with a coating that is suitable for reducing friction with objects that may be inserted within the capsule shaft 232, for example additional features of the retrieval device 200, such as the hook sheath 222 previously described. The coating may include a smooth plastic or polymer coating. For example, the coating may be made from any suitable material that provides a smooth surface with a low coefficient of friction. The coating may be made from a medical grade material that provides a low friction surface. For example, the coating may include a smooth plastic or polymer coating such as fluorinated ethylene propylene (FEP) or a polytetrafluoroethylene such as that sold under the tradename Teflon™. The coating may comprise a material that can be melted and reflowed, such as thermoplastics, or thermoplastic elastomers. For example, the coating may be made from polyether block resins such as that sold under the tradename Pebax®.

As shown in FIG. 10, the capsule 230 is generally cylindrical in shape and has a first end 410, a second end 412, a first section 406, and a second section 408. As shown, the capsule 230 has an outer diameter 402 along the first section 406, an outer diameter 422 along the second section 408, and an inner bore defining an inner diameter 404. The capsule 230 may be shaped to facilitate insertion of the capsule 230 into a body of a patient, such as into a body lumen. In some embodiments, the first end 410 of the capsule 230 may be rounded or tapered and the second end 412 may be rounded or tapered. That is, the inner and/or outer diameter of the capsule 230 may change in size at various locations along the outer diameter 422 and inner diameter 404, for instance, to define a suitable shape to help insert or extract the capsule 230 from within a patient. The outer diameter 402 along the first section 406 of the capsule may be substantially constant along a length of the capsule 230, and the outer diameter 422 along the second section 408 that changes in size, such as tapering near the second end 412. In some embodiments, the second section 408 of the capsule 230 may have an outer diameter 422 that tapers or reduces in size from the outer diameter 402 of the first section 406 to a size that is substantially the same as an outer diameter 424 of the capsule shaft 232.

The first section 406 of the capsule 230 may have an inner diameter 404 that is relatively constant along the length of the inside of the capsule 230. In some embodiments, the inner diameter of the second section 408 tapers inward near the second end 412 of the capsule 230. In some embodiments, the second section 408 has a tapering inner diameter that reduces from the inner diameter 404 of the first section 406 down to an inner diameter that is substantially the same as the inner diameter 426 of the capsule shaft 232.

In some embodiments, the capsule 230 may be formed from a single unitary body. That is, the capsule may be formed as a continuous piece of material that forms the entire capsule 230. In another example, the capsule 230 may be formed from multiple components form the capsule 230. Having the capsule 230 formed from multiple components may provide various additional features. This is disclosed further below with reference to FIGS. 11 to 14.

In some embodiments, the capsule 230 may be constructed from a rigid durable material such as metal, plastic, or other polymer. For example, the capsule 230 may be made from any suitable medical grade material that provides a smooth surface with reduced friction. In some embodiments, the capsule 230 may be from fluorinated ethylene propylene (FEP), polyoxymethalene (POM), polycarbonate, PEEK, or nylon. In some embodiments, the capsule 230 may be constructed from a flexible material that may bend or deform around objects yet is substantially rigid and incompressible along the capsule length. For example, the capsule 230 may be flexible to assist with advancement of the capsule into the body of a patient. The capsule 230 may be flexible such that the capsule 230 can bend at an angle to a longitudinal axis of the capsule 230. In some embodiments, the capsule 230 may be formed of a tube or a lumen. In some embodiments, the capsule 230 may be made from a coil reinforced tube, or a tube cut to create a spring or a coil. The capsule 230 may incorporate segments along the length of the capsule with each segment including space in between. The spaces may allow the capsule to flex or bend in a traverse direction; yet collapse in response to a compressive force applied along the length of the capsule to form a rigid structure.

The capsule 230 may have a liner or coating over a portion of the surface of the capsule 230 along inner diameters 404, 428 and/or a coating over a portion of the surface of the capsule 230 along the outer diameters 402, 422. The liner or coating may be a low friction or friction reducing liner. A low or reduced friction liner may enable the capsule 230 to be inserted into a body of a patient or allow objects to be drawn into the capsule 230 with less force. For example, a coating made from FEP or a polytetrafluoroethylene such as that sold under the tradename Teflon™ may be added to the surface of the inner diameters 404, 428 and/or the outer diameters 402, 422 of the capsule 230. In some embodiments, the capsule 230 may include material that allows the capsule 230 to be viewed while inside the patient using radiography.

FIGS. 11A and 11B show a perspective view and a side view, respectively, of a further example of the capsule 230, in accordance with various aspects of the present disclosure. As shown in FIGS. 11A and 11B, the capsule 230 includes a first section 406, a second section 408 and a third section 407 located toward the first end 410. As shown in FIG. 11B, the third section 407 defines the opening 409 to the inside of the capsule 230. The opening 409 is sized and shaped to allow the capsule 230 to receive objects within the capsule 230, such as the anchor 110 shown in FIG. 6. In some embodiments, the third section 407 has an outer diameter 411 that is the same as the outer diameter 402 of the first section 406. Alternative configurations of the capsule 230 are also envisioned. For example, in some instances, the third section 407 has an outer diameter 411 that is larger than the outer diameter 402 of the first section 406. In some instances the third section 407 has an outer diameter that is widest near the first end 410 and is narrowest near the first section 406. The third section 407 may also have an inner diameter that is widest at a section near the opening 409 at the first end 410 and tapers to a narrower diameter near the first section 406. The second section 408 may have an outer diameter 422 that is widest at a section nearest the first section 406 and the outer diameter 422 tapers to a smaller diameter near the second end 412.

FIG. 11B includes a partial cut away view along a section of the capsule 230 to show additional features. As shown, at least a portion of the capsule 230 comprises a coil 413 formed from a length of material rotated about a central longitudinal axis, which generally corresponds to an axis indicated by the arrow 405. In another example, the capsule may comprise a material formed into a braided or woven structure. In some embodiments, the coil 413 defines the body of the capsule 230. That is, the coil 413 extends from the first end 410 to the second end 412 and defines the entire length of the capsule 230. The coil 413 may have a radius of curvature that increases or decreases along sections of the length of the coil. The coil 413 may define an outer diameter that tapers in the direction of the central longitudinal axis, for example along the second section 408 and/or the third section 407. The coil 413 may define an inner surface that defines a lumen extending along the length of the first section 406, the third section 407, and/or the second section 408. In some examples, the third section 407 may be formed from a first end piece, and the second section 408 may be formed from a second end piece. This is described further below.

In some embodiments, the coil 413 may be uncoated, and the coil 413 defines the outer surface and inner surface of the capsule 230. As shown in FIG. 11B, the capsule 230 may include a cover 415. The cover 415 may be a coating that is applied over the coil 413. For example, the cover 415 may be a coating, such as a polymer or resin that is spread over the coil and allowed to form or harden around the outer surface and/or inner surface of the coil 413. The cover 415 may be a film that is formed separate from the coil and then laminated or wound onto the coil 413. In another example, the cover 415 may be extruded separately from the coil 413 and then then added to surfaces of the coil, for instance as a jacket. The cover 415 may fill in the spaces between each winding of the coil 413 and form a unitary body with a smooth continuous surface defining the outside and/or inside surface of the capsule 230.

In some instances, the cover 415 is formed from rigid material that maintains the capsule 230 in a suitable shape. In another example, the cover 415 may be formed from a flexible or pliable material such that the capsule 230 is capable of bending or flexing. For example, the cover 415 may be formed from a polymer such as a plastic or rubber that is applied over the coil 413 and allows the cover 415 to flex with the coil 413 while maintaining the cover 415 as a continuous layer over the coil 413. The cover 415 may comprise a material that reduces friction with objects that may come in contact with the capsule 230. In some embodiments, the cover 415 may include a hydrophilic material. In some embodiments, the cover 415 may comprise a polymer such as nylon, polycarbonate, polyethylene, polyethylene terephthalate, polyacetal, polyformaldehyde, a polyoxymethylene such as that sold under the tradename Delrin®, or a polyether block resin such as that sold under the tradename Pebax®. The cover 415 may include material having a low coefficient of friction such that the capsule 230 can pass within a body lumen of a patient, such as an esophagus, stomach, or intestine, or allow objects to be drawn into the capsule with minimal force. For example, the cover 415 may include material such as silicon, FEP or Teflon™.

Figure 12B:
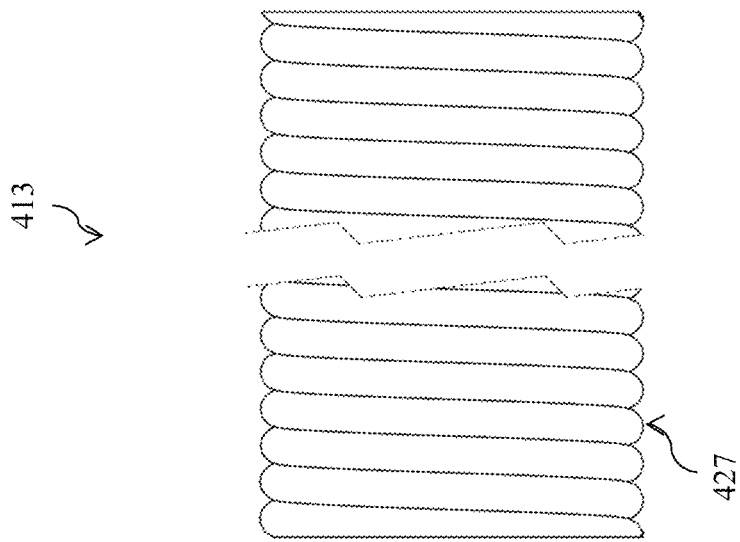
FIG. 12B is a side view of a portion of the capsule depicted in FIG. 11A, in accordance with various aspects of the present disclosure.
Figure 12A:
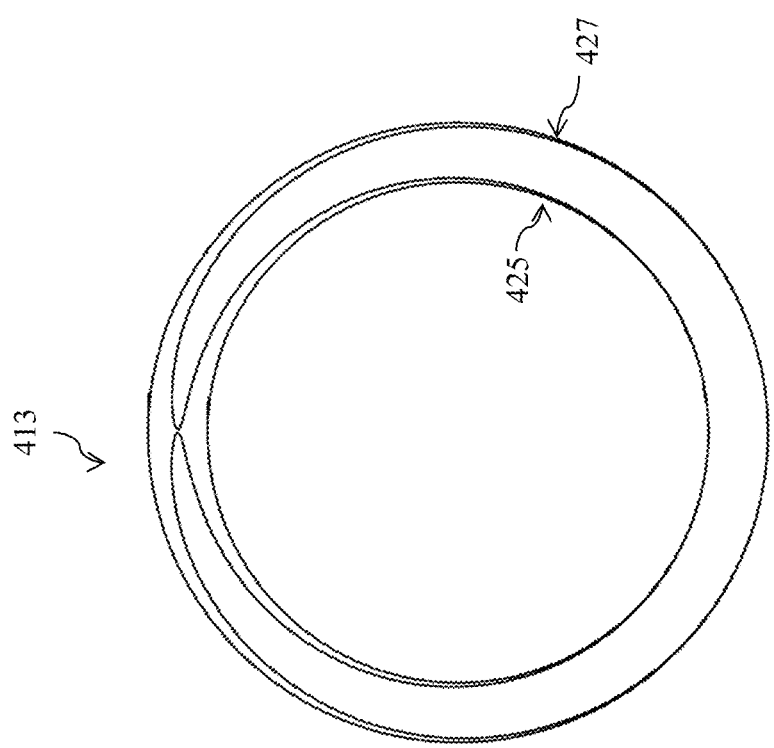
FIG. 12A is an end view of a portion of the capsule depicted in FIG. 11A, in accordance with various aspects of the present disclosure.

FIGS. 12A and 12B show an end view and a side view, respectively, of the coil 413, to show additional features. The coil 413 may be formed from a strand of material wound about a central longitudinal axis to form a cylinder. As shown in FIG. 12A, the coil 413 forms a cylinder having an inner surface 425 and an outer surface 427. The cylinder defined by the coil 413 defines an inner space that defines a lumen. As previously disclosed, in some examples, the inner surface 425 and outer surface 427 of the coil 413 define the inner surface 425 and outside surface of the capsule 230. That is, in some instances the inner surface 425 and outer surface 427 of the coil 413 are not coated or covered with an additional component. In some examples, the outer surface 427 and/or the inner surface 425 of the coil 413 may be covered with a second material. The second material may fill in spaces between adjacent windings of the coil and define a unitary, continuous surface on the inside of the capsule 230. For example, the outer surface 427 and/or the inner surface 425 of the coil may be covered with a coating or a liner of the second material, or the second material may be formed into a tube that is inserted into the coil 413 and forms the inner surface of the capsule 230. The second material may be used to reduce friction and/or provide abrasion resistance, for example to ensure smooth, uninterrupted passage of an object that is being pulled into the capsule 230. The second material may be a nonstick material, such as a hydrophilic material or a PTFE liner. In additional examples, the cover 415 shown in FIG. 11B, may be on the outer surface 427 of the coil 413 and define the outside surface of the capsule 230. Additionally or alternatively, the cover 415 may be on the inner surface 425 of the coil 413 and define the inside surface of the capsule 230 shown in FIGS. 11A and 11B. For example, the second material that may be included along the inner surface 425 the coil 413 to form the inside surface of the capsule 230 may be a polymer such as nylon, polycarbonate, polyethylene, polyethylene terephthalate, polyacetal, polyformaldehyde, a polyoxymethylene such as that sold under the tradename Delrin®, or a polyether block resin such as that sold under the tradename Pebax®. The inner surface 425 the coil 413 may be lined with a second material that is nonstick or has a low coefficient of friction, for example material such as silicon, FEP, or Teflon™.

As shown in FIG. 12B, the coil 413 may be formed from a strand of material wound about a central longitudinal axis to form a cylinder. In another example, the coil may be formed from strands of material that are formed into additional patterns such as woven, helical, braided or other patterns. The windings of the coil may be closely packed, and in some instances in contact with one another, which prevents the coil 413 from compressing along the central longitudinal axis. The coil 413 may be resilient to prevent the coil 413 from extending or stretching along the central longitudinal axis and allowing gaps to open between adjacent windings. The individual windings of the coil 413 may be adjacent and in contact with one another, yet able to move relative to each other in a direction perpendicular to the central longitudinal axis such that the coil 413 can flex or bend in a direction perpendicular to the central longitudinal axis. The coil 413 may also be resilient to resist compressing or collapsing of the coil 413 inward toward the axis of the coil 413. With the coil 413 resistant to compression or expansion along the central longitudinal axis, the coil 413 can be inserted into, or withdrawn from within a body lumen without the individual windings of the coil separating and opening gaps between adjacent windings, which can form pinch points when the gaps close.

The coil 413 may be configured such that the coil 413 is resilient and maintains a cylindrical shape defining an outer surface 427 and/or an inner surface 425 that are continuous, yet is flexible such that the coil 413 can be bent or curved along the central longitudinal axis. In some instances the coil 413 is resilient enough to withstand expansion or compression in response to forces along the length or the circumference of the coil 413. For example, the coil 413 may be resilient to withstand compression or expansion in the direction of the central longitudinal axis when an object is drawn into the coil 413. The coil 413 may also be resilient to withstand expansion or compression along the circumference while an object is positioned within the coil 413.

As shown in FIG. 12A, the coil 413 has a wall thickness defined between the inner surface 425 and outer surface 427. In some instances, the wall thickness is about 0.05 cm, about 0.10 cm, about 0.15 cm, about 0.02 cm, or a value between any pair of the foregoing values, although additional thicknesses are contemplated. In an example, a coil 413 with a wall thickness of about 0.14 cm was formed. The outer surface 427 of the coil 413 defines an outer diameter of the coil 413. In some instances, the outer diameter of the coil 413 is about 0.50 cm, about 1.0 cm, about 1.5 cm, about 2.0 cm, or a value between any pair of the foregoing values, although additional thicknesses are contemplated. In one example, a coil 413 with an outer diameter of about 1.4 cm was provided. In some instances, the length of the coil is about 5.0 cm, about 7.0 cm, about 11.0 cm, about 13.0 cm, or a value between any pair of the foregoing values, although additional lengths are contemplated. In one example, a coil with a length of about 9.5 cm was formed. Materials used to construct the coil 413 may comprise a resilient material such as a polymer, for example a plastic or rubber. In still further examples, the coil 413 may be made from a metal or an alloy such as titanium, stainless steel, or a shape memory alloy. In one exemplary embodiment, a coil 413 was formed using stainless steel.

FIGS. 13A and 13B show an end view and a side view, respectively, of a first end piece 431 that forms the third section 407 of the capsule shown in FIGS. 11A and 11B in some examples. As shown in FIG. 13A, the first end piece 431 is shaped generally as a cylinder defining a first inner surface 433 and an outer surface 435. FIG. 13B shows the first end piece 431 from a side view. As shown in FIG. 13B, the outer surface 435 defines an outer diameter 439 of the first end piece 431 which may correspond with the outer diameter 411 of the third section 407, described with reference to FIGS. 11A and 11B. The first inner surface 433 of the first end piece 431 also defines a first inner diameter 441 that corresponds with the inner diameter of the third section 407, described with reference to FIGS. 11A and 11B. As shown, the first end piece 431 includes a second inner surface 437 that defines a second inner diameter 443 that may be sized to fit around the coil 413 shown in FIG. 12B, such as along the outer surface 427. In some embodiments, the first end piece 431 may resemble a funnel with an inner diameter widest near the opening 409 and that tapers down to an inner diameter that is narrow at a point further from the opening 409.

Figure 14B:
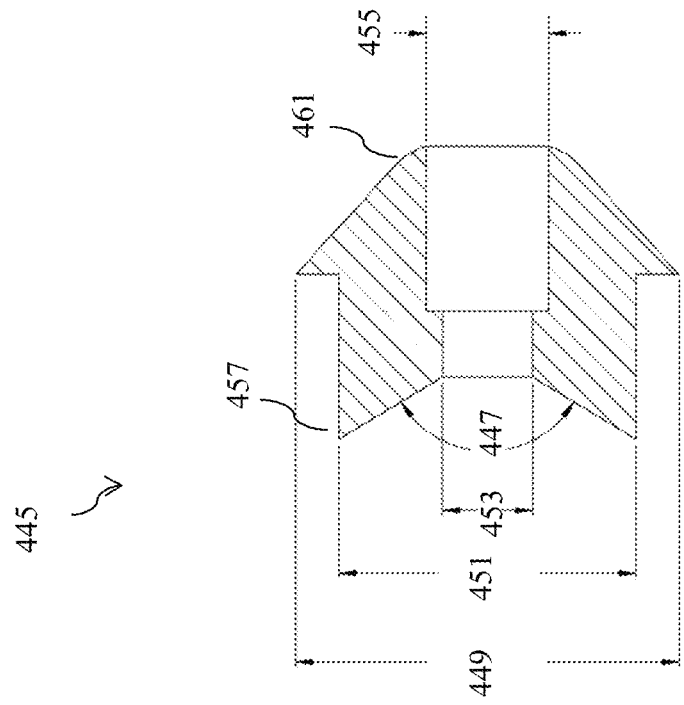
FIG. 14B is a side view of a portion of the capsule depicted in FIG. 11A, in accordance with various aspects of the present disclosure.
Figure 14A:
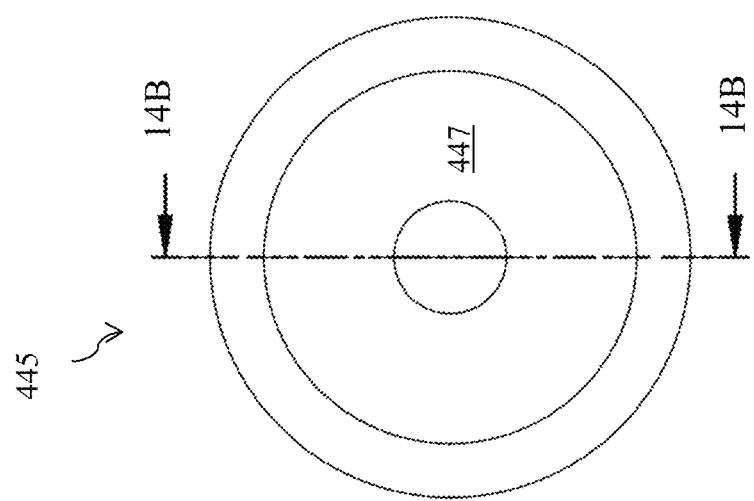
FIG. 14A is an end view of a portion of the capsule depicted in FIG. 11A, in accordance with various aspects of the present disclosure.

FIGS. 14A and 14B show an end view and a side view, respectively, of a second end piece 445 that forms the second section 408 of the capsule shown in FIGS. 11A and 11B in some examples. As shown in FIG. 14A, the second end piece 445 is generally circular when viewed along the central longitudinal axis. The second end piece 445 defines a first inner surface 447 that is generally tapered along the central longitudinal axis.

FIG. 14B shows a side view of the second end piece 445. As shown in FIG. 14B, the second end piece 445 has a first end 457, a second end 461, and defines a first outer diameter 449 that corresponds to the outer diameter 422 of the second section 408 described with reference to FIGS. 11A and 11B. As shown in FIG. 14B, the first outer diameter 449 tapers such that the first outer diameter 449 is wider at a section nearest the first end 457 and narrower at a section near the second end 461. The second end piece 445 has a second outer diameter 451 that is narrower than the first outer diameter and is sized to fit within the coil 413 shown in FIGS. 12A and 12B, such as within the lumen defined by the inner surface 425 of the coil. As shown, the second end piece 445 defines a first inner diameter 453 along a section near the first end 457, and a second inner diameter 455 along a section near the second end 461. The first inner diameter 453 may correspond with the inner diameter 426 of the capsule shaft 232 shown in FIG. 10. The second inner diameter 455 may be sized to correspond to the outer diameter 424 of the capsule shaft 232 shown in FIG. 10, such that the capsule shaft 232 may be positioned within the second end 461 of the second end piece 445.

In some embodiments, the first end piece 431 and/or the second end piece 445 may be made from a polymer such as nylon, polycarbonate, polyethylene, polyethylene terephthalate, polyacetal, polyformaldehyde, a polyoxymethylene such as that sold under the tradename Delrin®, or a polyether block resin such as that sold under the tradename Pebax®. Additionally or alternatively, the surfaces of the first end piece 431 and/or the second end piece 445, such as the first inner surface 433 and/or the outer surface 435 of the first end piece 431, may also include material that is nonstick or has a low coefficient of friction, for example material such as silicon, FEP, or Teflon™.

In certain instances, the capsule 230 shown in FIGS. 11A and 11B is formed by assembling the coil 413, shown in FIGS. 12A and 12B, the first end piece 431 shown in FIGS. 13A and 13B, and the second end piece 445 shown in FIGS. 14A and 14B. For instance, the first end piece 431 may be positioned around a section of the length of the coil 413, such as by inserting one end of the coil 413 into the first end piece 431 with the outer surface 427 of the coil 413 adjacent to the second inner surface 437 of the first end piece. The second end piece 445 may be positioned inside a section of the length of the coil 413, such as by inserting the first end 457 of the second end piece 445 into the coil 413. In this configuration, the first end piece 431 defines the opening 409 to the inside of the capsule 230 shown in FIG. 12B.

In embodiments of the capsule 230 having a cover 415 as shown in FIG. 11B, the cover 415 may be integral with the first end piece 431 and additionally or alternatively integral with the second end piece 445. That is, the first end piece 431 may be integrally formed with the cover 415 such that the first end piece 431 is a continuous unitary body with the cover 415. The first end piece 431 may be integrally formed with the cover 415 such that the capsule 11B has a smooth continuous surface along the inside and outside. The second end piece 445 may also be integrally formed with the cover 415 such that the second end piece 445 is continuous with the cover 415. The inner diameter of the capsule 230 may be defined by the first inner diameter 441 of the first end piece 431, the inner diameter of the coil 413, and/or in some instances the cover 415, for example with the cover 415 on the inside surface of the coil 413. The outer diameter of the capsule 230 may be defined by the outer diameter 439 of the first end piece 431, the outer diameter of the coil 413, the first outer diameter 449 of the second end piece 445, and/or in some instances the cover 415, for example with the cover 415 on the outside surface of the coil 413. In some instances, the inner diameter of the capsule 230 is about 0.50 cm, about 1.0 cm, about 1.5 cm, about 2.0 cm, or a value between any pair of the foregoing values, although additional thicknesses are contemplated. In one example, a capsule with an inner diameter of about 1.1 cm was provided. In some instances, the outer diameter of the capsule 230 is about 0.8 cm, about 1.2 cm, about 1.7 cm, about 2.1 cm, or a value between any pair of the foregoing values, although additional thicknesses are contemplated. In one example, a capsule with an outer diameter of about 1.5 cm was provided.

The capsule 230 described herein, for example comprising the coil 413 or an alternative structure such as a braid or woven material, is capable of flexing or bending along the longitudinal axis. During a retrieval process, the capsule 230 may be inserted within a body lumen, such as the throat, esophagus, stomach, or intestine of a patient. With the capsule 230 able to flex or bend, the capsule 230 may be more maneuverable when being inserted or retracted from a within body lumen compared with a capsule that cannot flex or bend. The capsule 230 that is able to flex or bend may help a user to more easily maneuver the capsule 230 within a body lumen, for example through bends or curves in a patient's throat or esophagus. The capsule 230 that is able to flex or bend may also help a user to more easily maneuver the capsule 230 through a body lumen when an object is positioned within the capsule 230. Additionally, the capsule 230 having certain surfaces formed from a material that has a low coefficient of friction may help to make a deployment or retrieval process easier. For example, with a coating comprising a nonstick or low stick material such as silicon or a fluorocarbon such as Teflon™ on the leading edge and/or the inside surface of the capsule 230, an object may be pulled into or deployed from inside the capsule 230 than without such a coating. As a further example, with a coating comprising a nonstick or low stick material on the outside surfaces of the capsule 230, the capsule 230 may be inserted through or extracted from inside a body lumen than a capsule 230 without such a coating.

Figure 15A:
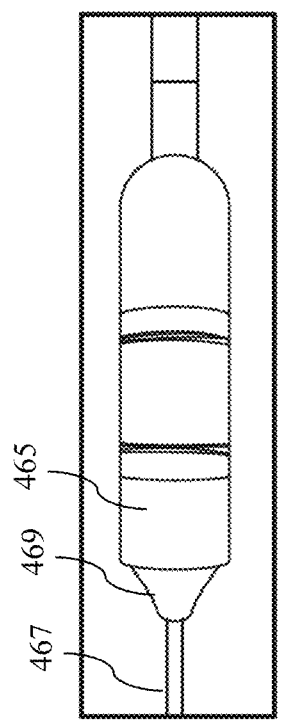
FIGS. 15A to 15C are side views of various example features that may be used with a capsule, in accordance with various aspects of the present disclosure.
Figure 15C:
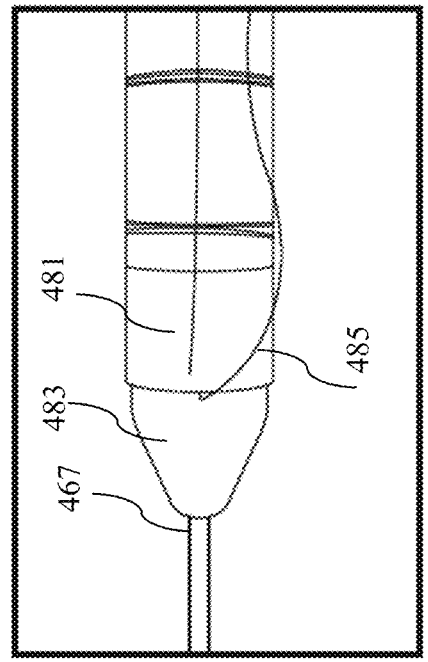
Figure 15B:
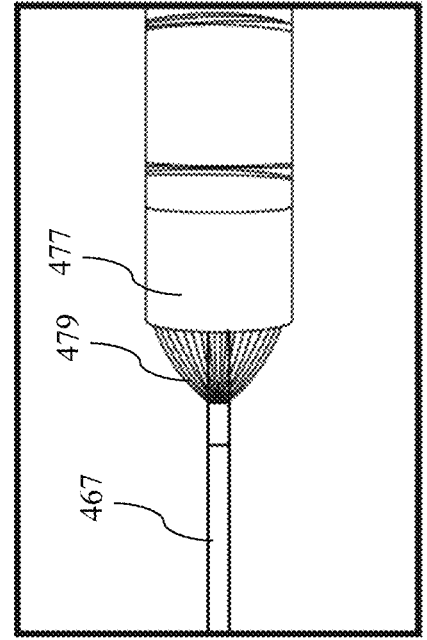

FIGS. 15A to 15B are side views of various example capsules showing additional features that may be included, for example with the capsule 230 described above. FIG. 15A is a side view of a capsule 465 with a catheter 467 and including a tip 469 that may be included at the opening to the inside of the capsule 465. In some instances, the tip 469 may be positioned at the opening 409 to the capsule 230 shown in FIG. 10. In some embodiments, the tip 469 may provide a transition around the capsule 465 such that the capsule 465 is more easily advanced along a line of travel, such as within a lumen. The tip 469 may provide a tapered transition from the foremost location on the capsule 465 to the outer diameter of the capsule 465 and may act as a wedge to ease the insertion of the capsule 465 through a lumen. The tip 469 may also cover the opening to the capsule 465 such that objects are prevented from entering the capsule 465 as it is advanced along a line of travel, such as being inserted within a lumen. In some instances, the capsule 465 is used to deploy a device from inside the capsule 465. For example, the anchor 110 and/or sleeve 120 shown in FIG. 4 may be deployed from within the capsule 465. When the capsule 465 is deployed, the tip 469 may be removed to allow a device to be deployed from within the capsule 465.

FIGS. 15B and 15C show various example designs for a tip and capsule that may facilitate removing the tip from the capsule. FIG. 15B shows a capsule 477 with a tip 479 that may be formed from multiple pieces such with as a woven material or a plurality of ribs. The tip 479 may be collapsible such that the tip 479 can be reduced in size to help fit the tip 479 inside the capsule 477. When the capsule 477 is deployed, the tip 479 may be removed from the opening at the first end of the capsule 477 by collapsing the tip 479 and retracting it into the capsule 477. For example, the tip 479 may be collapsed and guided by the catheter 467 into the capsule 477. FIG. 15C shows a further example of a capsule 481 with a tip 483 that may be formed as a single solid body. The tip 483 may be connected to the capsule 481 with a fastener 485, for example a string or a clip. When the capsule 481 is deployed, for example within a body lumen of a patient, the tip 483 may be removed from the opening at the first end of the capsule 481 by releasing the fastener 485 which disconnects the tip 483 from the capsule 481. For example, the fastener 485 may be a suture that connects the tip 483 to the capsule 481. The suture may be cut or untied to disconnect the tip 483 from the capsule 481, and the tip 483 may then separate from the capsule 481 and drop from the catheter 467.

Figure 16A:
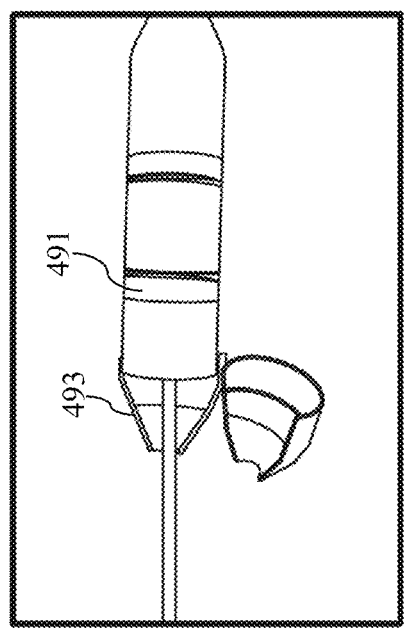
FIGS. 16A and 16B are side views of various additional example features that may be used with a capsule, in accordance with various aspects of the present disclosure.
Figure 16B:
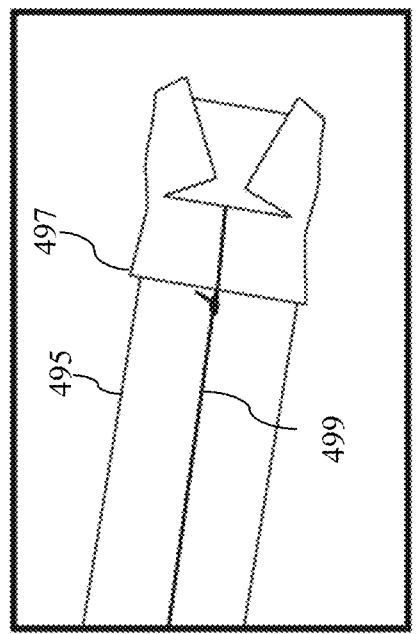

FIGS. 16A and 16B show various further designs for a tip and capsule that may facilitate removing the tip from the opening to the capsule and deploying a device from within the capsule. FIG. 16A shows a capsule 491 including a tip 493 that is configured to break into multiple pieces when the capsule 491 is deployed, such as when the capsule 491 is positioned within the body lumen of a patient. The tip 493 may be connected to an external device such as a leash (not shown) that may be used to cause the tip 493 to break and fall away from the capsule 491. FIG. 16B shows a capsule 495 including a tip 497 that can be retracted from the opening to the capsule 495, for example when the capsule 495 is deployed. The tip 497 may be maintained in a closed position over the opening to the capsule 495, for example with a spring. To remove or open the tip 497, the tip 497 may be controlled by a retraction device such as a leash 499 to pull the tip 497 back over the capsule 495. In this example, pulling the tip 497 back over the capsule 495 causes the tip 497 to open and allow access to the inside of the capsule 495.

Figure 17A:
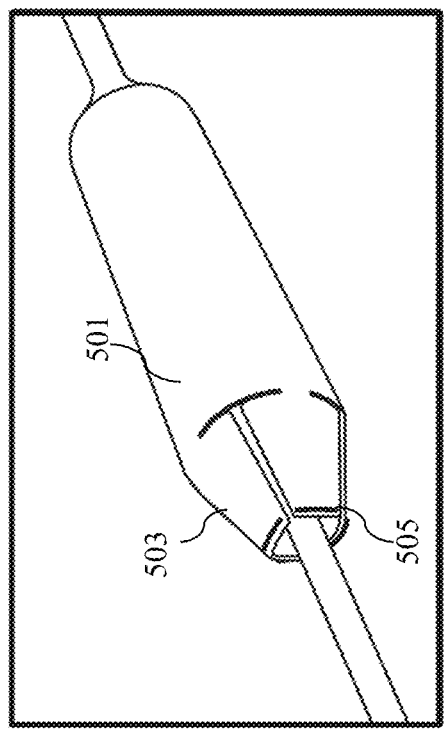
FIGS. 17A and 17B are perspective views of various additional example features that may be used with a capsule, in accordance with various aspects of the present disclosure.
Figure 17B:
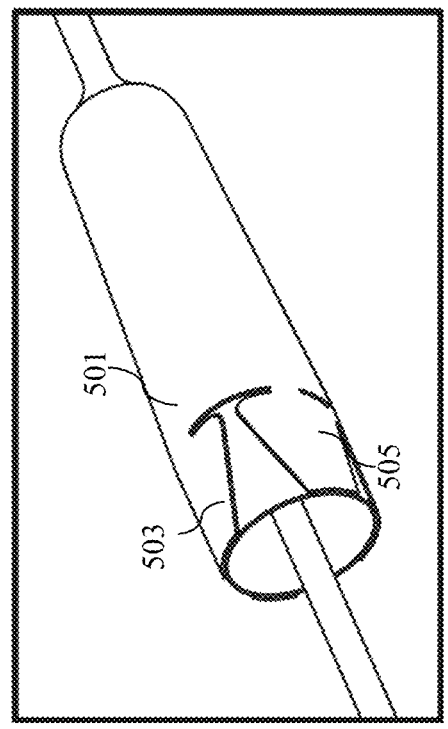

FIGS. 17A and 17B show various further designs for a tip and capsule that may facilitate removing the tip from the opening to the capsule and deploying a device from within the capsule. FIG. 17A shows a capsule 501 including a tip 503 that is formed from multiple sections that may be connected to each other to form the tip 503. For example, the tip 503 may include a first section 505 that is held in place around the opening of the capsule 501 by attaching the first section 505 to the remaining sections of the tip 503 to maintain the tip 503 in a closed position at the opening. The first section 505, for example, may be glued or sutured to the remaining sections of the tip 503. FIG. 17B shows the capsule 501 with the tip 503 removed from the opening to the capsule 501. When the capsule 501 is deployed, the tip 503 may be removed from the opening to the capsule 501, for example, by advancing the capsule 501 through the tip 503, causing the sections of the tip 503 to break apart from each other. For example, the capsule 501 may be advanced through the tip 503 breaking the suture or glue connecting the first section 505 to the remaining sections of the tip 503. After the sections of the tip 503 are separated from each other, the capsule 501 can be further advanced such that the capsule 501 is inserted through the tip 503, removing the tip 503 from the opening to the capsule 501.

Figure 18A:
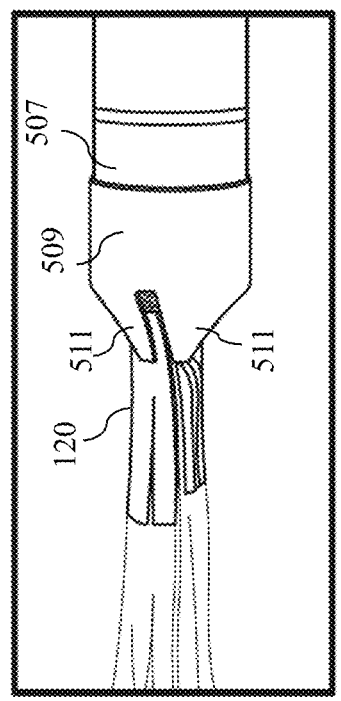
FIGS. 18A to 18C are side views of an example tip that may be used with a capsule, in various steps of deployment, in accordance with various aspects of the present disclosure.
Figure 18C:
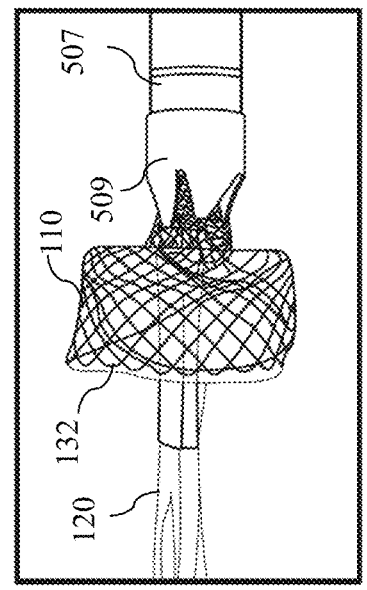
Figure 18B:
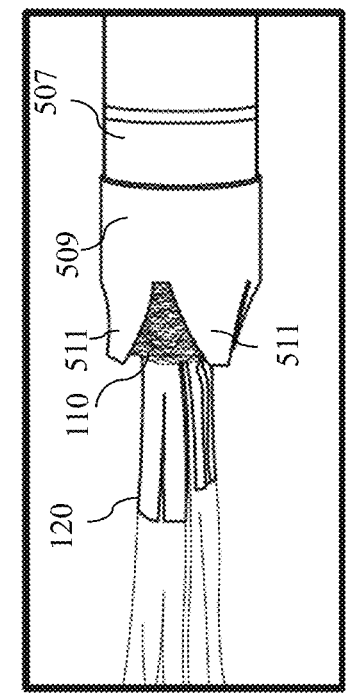

FIGS. 18A to 18C show various further designs for a tip and capsule that may be used to deploy a device from inside the capsule without removing the tip from the opening to the capsule. For example, the gastrointestinal device 100 having the sleeve 120 and anchor 110 shown in FIG. 4 can be deployed from inside a capsule using the device described herein. FIG. 18A shows a capsule 507 including a tip 509 that is formed from sections 511 that in combination form the tip 509. For example, the tip 503 may include sections 511 that are formed from a pliable or resilient material such as cloth, a plastic, or rubber. The tip 509 provides a transition from the catheter to the larger diameter of the capsule 507, helping ease insertion of the capsule 507 through a body lumen of a patient. FIG. 18A shows the capsule 507 and tip 509 with a section of the sleeve 120 positioned through an opening in the tip 509, for example between the sections 511 of the tip 509. In this configuration, the anchor is held within the capsule 507 in a collapsed configuration as the capsule 507 is inserted through a body lumen. FIG. 18B shows the sleeve 120 removed from the capsule 507 and the anchor 110 in a partially deployed position. As shown in FIG. 18B, the sections 511 of the tip 509 can separate from each other and move outward from the opening to the capsule 507. In this example, the tip 509 allows the anchor 110 to pass through the tip, and allows the anchor 110 to be deployed from within the capsule 507 without removing the tip 509 from the capsule 507. As shown in FIG. 18C, the distal portion 132 is deployed from the capsule 507 and has expanded outside the capsule 507. The remaining portions of the anchor 110 can also be deployed from inside the capsule 507 without removing the tip 509. In this example, the capsule 507 can be used to deploy the gastrointestinal device 100 having a sleeve 120 and anchor 110 shown in FIG. 6 into a patient without separating the tip 509 from the capsule 507 and without needing a mechanism to retract the tip 509 from the opening to the capsule 507. In this example, the tip 509 may be formed as a unitary body with slits that can tear and allow the sections 511 of the tip 509 to separate from each other when the anchor 110 is pushed through the tip 509. In this manner, the tip 509 is a continuous body as the capsule 507 is advanced through a body lumen, and then the tip 509 opens when the anchor 110 is deployed.

Figure 19:
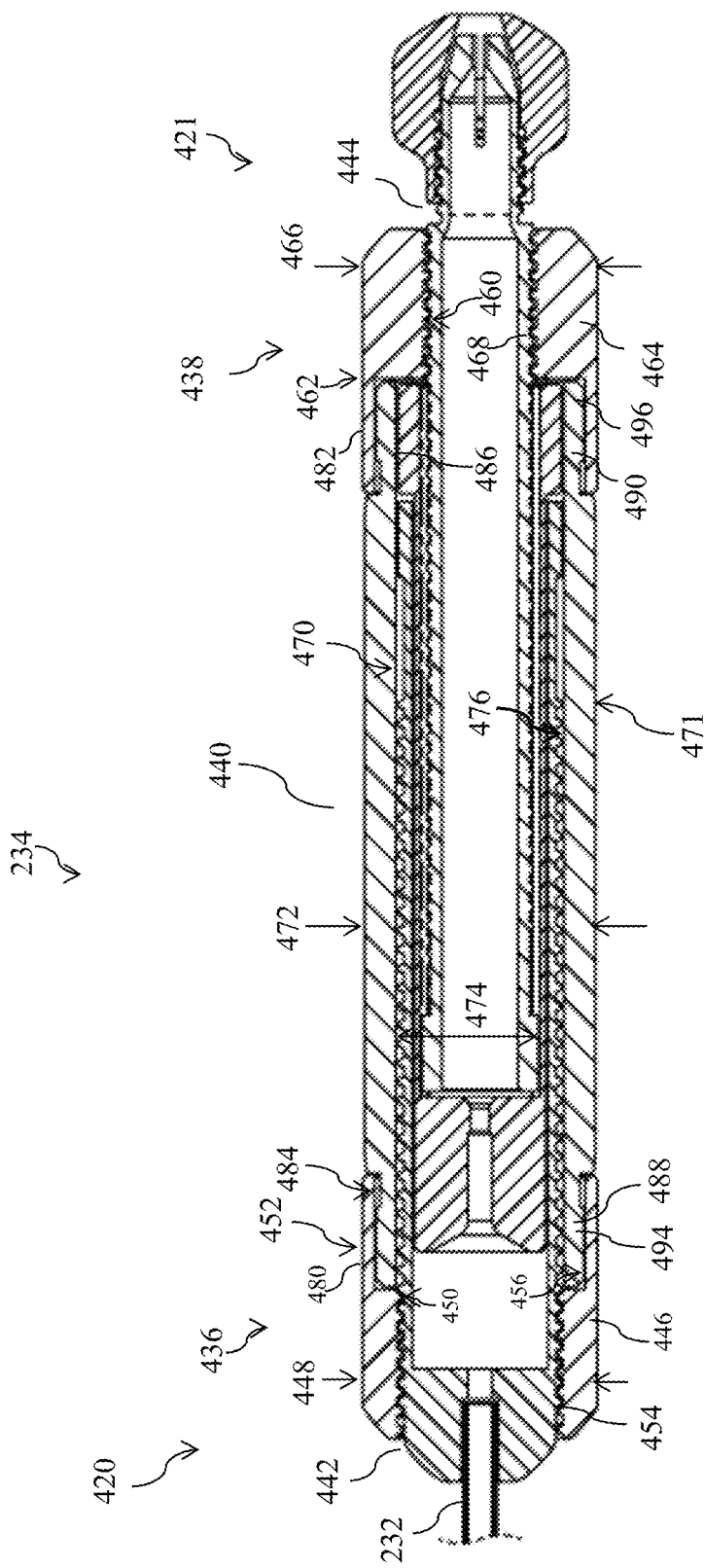
FIG. 19 is an overall schematic of a handle assembly showing certain internal features, in accordance with various aspects of the present disclosure.

FIG. 19 is a cross sectional schematic of the handle 234 shown in FIG. 10. The handle 234 may include features for moving the hook assembly 210 shown in FIGS. 9A and 9B in relation to the capsule assembly 212 shown in FIG. 10. In some embodiments, the handle 234 includes features to facilitate advancing or retracting the hook assembly 210 in relation to the capsule assembly 212, such as to pull the first end 310 of the hook cable 220 into the capsule 230 shown in FIG. 10. In some embodiments, the handle 234 may be configured to translate rotational actuation to longitudinal actuation to move the capsule assembly 212 and/or the hook assembly 210 in longitudinal relation to each other.

As previously described, the handle 234 has a first end 420, a second end 421, a first control knob 436 located at the first end 420, a second control knob 438 located at the second end 421 and a central core 440. The handle 234 defines a longitudinal axis along the length of the handle 234.

As shown in FIG. 19, the first control knob 436 has an inner surface 450 and an outer surface 452. The inner surface 450 of the first control knob 436 defines an inner diameter, and the outer surface 452 defines an outer diameter 448. In some embodiments, the outer diameter 448 of the first control knob 436 may vary along a circumference of the outer surface 452 of the first control knob 436. That is, the first control knob 436 may have features along the outer surface 452 that protrude or undulate from the outer surface 452 of the first control knob 436. Certain features may be included along the outer surface 452 of the first control knob 436 that are sized and/or shaped to facilitate a user's grip when turning the first control knob 436 in the circumferential direction in relation to the central core 440.

As shown in FIG. 19, the first control knob 436 may have a first section 446 having a first inner diameter and a second section 480 having a second inner diameter that is wider than the inner diameter of the first section 446. The inner diameter along the first section 446 of the first control knob 436 may be sized to fit the second sheath 442. The inner diameter along the second section 480 of the first control knob 436 may be sized to fit a portion of the central core 440. In some embodiments, the inner surface 450 of the first control knob 436 may be threaded along at least a first portion 454 of the inner surface 450 near the first end 420 of the handle 234. The inner surface 450 of the first control knob 436 may be smooth along a second portion 456 of the inner surface 450 of the first control knob 436 near the central core 440. The first portion 454 of the inner surface 450 of the first control knob 436 may be threaded with threads having crests that are higher along the inner surface 450 than the surface of the second portion 456 that is smooth. That is, the threads of the first portion 454 may have crests that extend radially inward further than the surface of the second portion 456.

As shown in FIG. 19, the second control knob 438 has an inner surface 460 defining an inner diameter, and an outer surface 462 defining an outer diameter 466. In some embodiments, the outer diameter 466 of the second control knob 438 may vary along a circumference of the outer surface 462 of the second control knob 438. That is, the second control knob 438 may have features along the outer surface 462 that protrude or undulate from the outer surface 462. Certain features may be included along the outer surface 462 of the second control knob 438 and may be sized and/or shaped to facilitate a user's grip when turning the second control knob 438 in the circumferential direction in relation to the central core 440.

As shown in FIG. 19, the second control knob 438 may have a first section 464 having a first inner diameter and a second section 482 that has a second inner diameter that is wider than the first inner diameter of the first section 464. The second control knob 438 may have a first inner diameter along the first section 464 which is sized to fit the third sheath 444, and a second inner diameter along the second section 482 which is sized to fit a portion of the central core 440. In some embodiments, the inner surface 460 may be smooth along a first portion 486 of the inner surface 460 near the central core 440. The inner surface 460 of the second control knob 438 may be threaded along at least a second portion 468 of the inner surface 460 near the second end 421 of the handle 234. The second portion 468 that is threaded may have threads with crests that are higher than the first portion 486 of the inner surface 460 that is smooth. That is, the threads of the second portion 468 may have crests that extend radially inward further than the surface of the first portion 486.

As shown in FIG. 19, the central core 440 has a first end 494, a second end 496, an outer surface 471 and an inner surface 476. The outer surface 471 defines an outer diameter 472 and the inner surface 476 defines an inner diameter 474. The inner surface 476 of the central core 440 may be threaded. In some instances, the inner surface 476 may be smooth. For example, the inner surface 476 may be threaded to engage threads along the outer surface of the second sheath 442. In some instances, the inner surface 476 is smooth and the inner diameter 474 is wide enough to slidably receive the second sheath 442 within the central core 440.

As shown in FIG. 19, the first end 494 of the central core 440 may include a first retaining feature 488, such as a projection or protrusion that has a corresponding fit with the second portion 456 of the inner surface 450 of the first control knob 436. The first retaining feature 488 may hold the first control knob 436 on the central core 440, while allowing the first control knob 436 to turn or swivel relative to the central core 440 without detaching from the central core 440. The second end 496 of the central core 440 may have a second retaining feature 490 such as a projection or protrusion that has a corresponding fit with the first portion 486 of the inner surface 460 of the second control knob 438. The second retaining feature 490 may hold the second control knob 438 on the central core 440, yet allows the second control knob 438 to turn or swivel relative to the central core 440 without detaching from the central core 440.

As shown in FIG. 19, the central core 440 has an outer diameter at the first end 494 that is sized to fit within the inner diameter of the second section 480 of the first control knob 436. The central core 440 has an outer diameter at the second end 496 that is sized to fit within the inner diameter of the second section 482 of the second control knob 438. The first end 494 of the central core 440 is positioned within the second section 480 of the first control knob 436, and the second end 496 of the central core 440 is positioned within the second section 482 of the second control knob 438.

Figure 20:
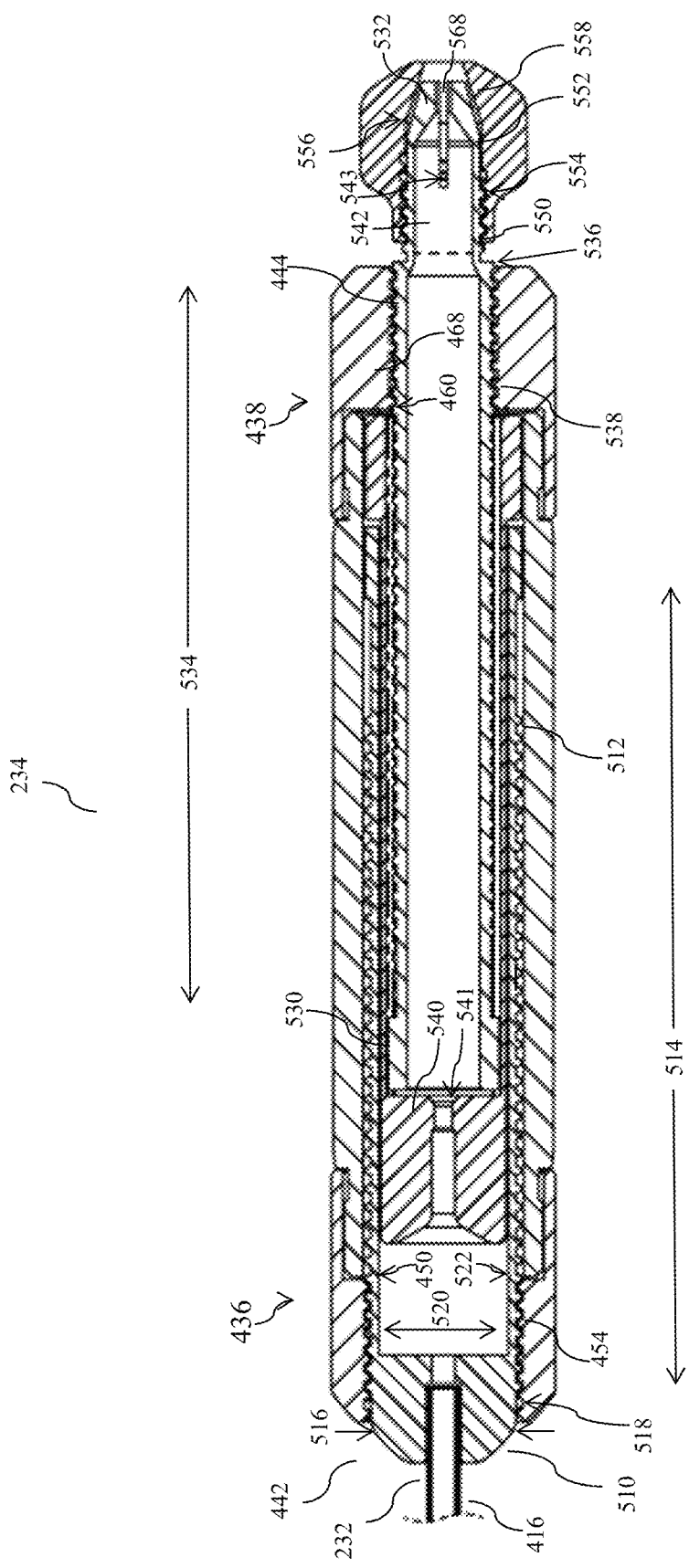
FIG. 20 is an overall schematic of a handle assembly showing certain internal features, in accordance with various aspects of the present disclosure.

FIG. 20 is a side view of a cross sectional schematic of the handle 234 of FIG. 10 showing certain features. As shown, the handle 234 includes the second sheath 442 and the third sheath 444. The second sheath 442 has a generally cylindrical shape having a first end 510, a second end 512, and a length 514 in between. The second sheath 442 has an outer surface 518 defining an outer diameter 516, and an inner surface 522 defining an inner diameter 520. In some embodiments, the first end 510 of the second sheath 442 may be attached to the second end 416 of the capsule shaft 232. As shown, the outer diameter 516 of the second sheath 442 is sized to fit within the inner diameter 474 of the central core 440, shown in FIG. 19. The outer surface 518 of the second sheath 442 may be threaded. The outer surface 518 may be threaded with a corresponding pitch as the thread located on the first portion 454 of the inner surface 450 of the first control knob 436. For example, the inner surface 450 of the first control knob 436 may have a female thread and the outer surface 518 of the second sheath 442 may have a male thread with a corresponding pitch to the thread that is on the inner surface 450 of the first control knob 436, such as the threads on the first portion 454 of the inner surface 450. In some embodiments, the inner surface 522 of the second sheath 442 may be smooth.

As shown, the third sheath 444 has a generally cylindrical shape having a first end 530, a second end 532, and a length 534 in between. The third sheath 444 has a first section 538 that has a first surface 536 that defines a first outer diameter along a portion of the length 534 of the third sheath. As shown in FIG. 20, the second end 532 of the third sheath 444 has a second section 550 having an outer diameter that is narrower than the first outer diameter along the first section 538 of the third sheath 444. In some embodiments, the second section 550 has an outer surface 554 that is threaded. The third sheath 444 has a third section 552 having an outer surface 556 that is smooth. A portion of the third section 552 is a transition section 558 with an outer diameter that tapers such that the outer diameter of a portion of the third section 552 transitions from an initial diameter that is similar in diameter to the second section 550 to a narrower final diameter. A portion of the third section 552 includes slots 568 formed through the width of the third section 552 parallel to the longitudinal axis of the handle 234.

The first outer diameter along the first section 538 of the third sheath 444 is sized to be received within the first inner diameter of the second section 550 of the second control knob 438. In some embodiments, the first outer diameter along the first section 538 of the third sheath 444 is sized to be received within the inner diameter 520 of the second sheath 442. In some embodiments the first surface 536 of the first section 538 of the third sheath 444 is threaded. The first surface 536 of the third sheath 444 may be threaded with a corresponding pitch as the thread on the second portion 468 of the inner surface 460 of the second control knob 438. For example, the inner surface 460 of the second portion 468 of the second control knob 438 may have a female thread and the outer surface of the first section 538 of the third sheath 444 may have a male thread with a corresponding pitch to a female thread on the second control knob 438 inner surface 460.

As shown in FIG. 20, the third sheath 444 includes a first section 540 having a first inner surface 541 and a second section 542 having a second inner surface 543. In some embodiments, the first inner surface 541 and/or the second inner surface 543 define a first inner diameter of the third sheath 444 section. The first inner diameter of the third sheath 444 is sized to receive the hook assembly 210, shown in FIGS. 9A and 9B. For example, the third sheath 444 may have an inner diameter that is wider than the outer diameter of the hook assembly 210. The first inner surface 541 and/or the second inner surface 543 of the third sheath 444 may be relatively smooth. In some instances, when the hook assembly 210 is deployed the hook assembly 210 may be slidably received within the third sheath 444. In some embodiments, the first inner diameter of the third sheath 444 defines the innermost diameter of the handle 234. That is, the third sheath 444 is the innermost portion of the handle 234 in the radial direction and the first inner diameter along the first section 540 of the third sheath 444 defines the inner diameter of the handle 234.

In some instances, the threads on the outer surface 518 of the second sheath 442 and the first surface 536 of the third sheath 444 have a suitable pitch angle that causes the second and third sheaths 442, 444 to advance a suitable distance in the longitudinal direction in response to each turn of the first and second control knobs 436, 438. The pitch angle of the threads on the second and third sheaths 442, 444 may also be sized such that a suitable amount of force is transferred to the second and third sheaths 442, 444 in the longitudinal direction when the first and second control knobs 436, 438 are rotated. The pitch angle of the threads on the second and third sheaths 442, 444 may also be sized such that a certain degree of rotational actuation of the first and second control knobs 436, 438 provides suitable amount of longitudinal actuation to advance the capsule assembly 212 and/or the hook assembly 210 in relation to the central core 440. In some embodiments, the handle 234 is configured to transfer a rotational force applied to the first and second control knobs 436, 438 to a longitudinal force against the second sheath 442 and/or third sheath 444. The longitudinal force applied to the second sheath 442 and/or third sheath 444 extends the second and third sheaths 442, 444 from each other and causes the capsule assembly 212 and hook assembly 210 to extend longitudinally in relation to the central core 440. The longitudinal force applied to the capsule assembly 212 and hook assembly 210 may be from about 5.0 pounds-force (22.2 Newtons) to about 25.0 pounds-force (111.2 Newtons). In some instances, the longitudinal force applied to the capsule assembly 212 and hook assembly 210 may be from about 5.0 pounds-force (22.2 Newtons) to about 35.0 pounds-force (155.7 Newtons). For example, the longitudinal force applied between the capsule assembly 212 and hook assembly 210 may be from about 5.0 pounds-force (22.2 Newtons), 10.0 pounds-force (44.5 Newtons), or about 15.0 pounds-force (66.7 Newtons), to about 25.0 pounds-force (111.2 Newtons), 30.0 pounds-force (133.4 Newtons) or about 35.0 pounds-force (155.7 Newtons), or a force between any pair of the foregoing values, although additional values are also envisioned.

As used herein, "thread" or "screw thread" is defined as a raised ridge wrapped around a cylinder or cone in the shape of a helix. As used herein, "pitch" is defined as the distance between the crest of one screw thread to the next. As used herein, screw "lead" is defined as the distance along a longitudinal axis that a screw travels in response to one complete turn of the screw. That is, the screw lead is the length traveled by a screw along the screw axis when the screw completes a 360 degree turn. As used herein, "pitch angle" is the angle of the threads of the screw in relation to the horizontal cross section of the screw. The pitch angle can also be described as the ratio of the longitudinal distance traveled by a screw in response to one complete 360 degree turn of the screw divided by the diameter of the screw.

Figure 21A:
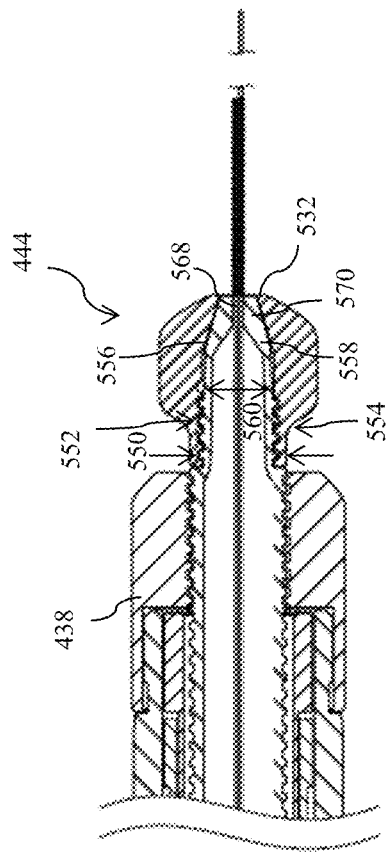
FIG. 21A is an overall schematic of a lock showing certain internal features, in accordance with various aspects of the present disclosure.

FIG. 21A shows a side view of a schematic of the second end 532 of the third sheath 444 shown in FIG. 20. As shown in FIG. 21A, the second end 532 of the third sheath 444 may have a transition section 558 with a diameter that decreases from a first outer diameter 560 similar in size to the diameter of the second section 550 to a narrower second outer diameter at the second end 532. The transition section 558 at the second end 532 of the third sheath 444 may have a smooth outer surface. The transition section 558 may comprise a slotted elongated portion having slots 568 through the third sheath 444 second end 532 extending a distance along the length of the transition section 558. The slots 568 may be formed through the entire outer diameter of the third sheath outer surface 556. That is, the slots 568 divide the second end 532 of the third sheath 444 into projections 570 or fingers, with the slots 568 in between the projections 570.

Figure 21B:
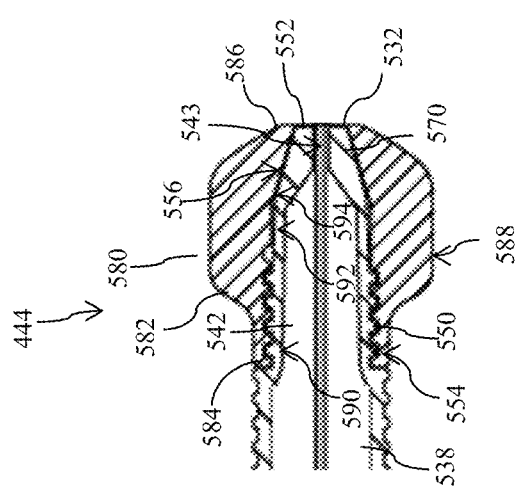
FIG. 21B is a schematic of a lock showing certain internal features, in accordance with various aspects of the present disclosure.

FIG. 21B shows a further side view of a schematic of the third sheath 444 near the second end 532. As shown in FIG. 21B, the third sheath 444 second end 532 may comprise a hook assembly lock 580. The hook assembly lock 580 includes a cap 582 having a first end 584, a second end 586, and an outer surface 588 defining an outer diameter. The outer surface 588 may include certain features, for example protrusions, to enable a user to turn the hook assembly in relation to the third sheath 444. The outer diameter of the cap 582 is larger than the inner diameter 564 of the second control knob 438, shown in FIG. 19. The hook assembly lock 580 has a first inner surface 590 defining a first inner diameter near the first end 584, a second inner surface 592 defining a second inner diameter, and a third inner surface 594 defining a third inner diameter. In some embodiments, first inner surface 590 of the cap 582 is threaded with a corresponding thread as the outer surface 554 of the second section 550 of the third sheath 444. As shown, the third inner surface 594 of the cap 582 tapers such that the third inner diameter decreases in width from a first diameter that is the same as the second inner diameter of the cap 582 to a smaller final inner diameter near the second end 586 of the cap 582. As shown, the second inner surface 592 and third inner surface 594 of the cap 582 are smooth.

As previously described with reference to FIG. 20, the third sheath 444 has a second section 550 that has an outer surface 554 that is threaded, and a third section 552 with an outer surface 556 that is smooth. As shown in FIG. 21B, to engage the hook assembly lock 580 the cap 582 is placed over the second end 532 of the third sheath 444 and turned to engage the threads on the outer surface 554 of the third sheath 444. The cap 582 can be turned to screw the cap 582 over the second end 532 of the third sheath 444 and advance the cap 582 along the third sheath 444 from the second end 532 toward the first section 538. As the cap 582 is advanced along the third sheath 444 near second end 532, the taper of the third inner surface 594 of the cap 582 compresses the second end 532 of the third sheath 444 radially inward, and decreases the size of the inner diameter of the second end 532 of the third sheath 444. As the projections 570 compress inward, the second inner surface 543 may be pressed against an object that is positioned within the inner diameter of the third sheath 444, such as the hook assembly 210. In the example shown in FIG. 21B, the hook assembly lock 580 is deployed similar to a collet. It is also envisioned that the hook assembly lock 580 may comprise an alternative configuration such as a clamp or clasp, for locking the hook assembly 210 to the third sheath 444 at the second end 532.

FIGS. 22A and 22B show side views of the handle 234 at various stages of deployment, according to some methods of use. The handle 234 may be deployed from a retracted configuration shown in FIG. 20 to an elongated or extended configuration shown in FIGS. 22A and 22B by extending the second sheath 442 and third sheath 444 away from the central core 440. FIG. 22A shows the third sheath 444 in a deployed position, and FIG. 22B shows the second sheath 442 in a deployed position. The second sheath 442 and third sheath 444 are extended from the central core 440 by rotating one or both of the first and second control knobs 436, 438.

As shown in FIG. 22A, the second control knob 438 has a first portion 486 of the inner surface 460 in contact with the second end 496 of the central core 440. The smooth surface of the first portion 486 allows the second control knob 438 to rotate in relation to the central core 440 without moving longitudinally in relation to the central core 440. As the second control knob 438 rotates in relation to the central core 440, the threads on the second portion 468 of the inner surface 460 of the second control knob 438 engage the threads on the first surface 536 of the third sheath 444 and advance or retract the third sheath 444 from the central core 440 along the longitudinal axis. By rotating the second control knob 438 in the circumferential direction in relation to the central core 440, the third sheath 444 is extended or retracted in relation to the central core 440 along the longitudinal axis of the handle 234.

As shown in FIG. 22B, the first control knob 436 has the second portion 456 of the inner surface 450 that is smooth in contact with the first end 494 of the central core 440. The first control knob 436 may rotate in relation to the central core 440 without moving longitudinally in relation to the central core 440. As the first control knob 436 rotates in relation to the central core 440, the threads of the first portion 454 of the inner surface 450 of the first control knob 436 engage the threads on the outer surface 518 of the second sheath 442 and advance or retract the second sheath 442 along the longitudinal axis. By rotating the first control knob 436 in the circumferential direction in relation to the central core 440, the second sheath 442 is extended or retracted in relation to the central core 440 along the longitudinal axis of the handle 234.

In some embodiments, the second sheath 442 is configured to extend from about 1.0 inches to about 5.0 inches away from the central core 440. That is, the second sheath 442 may be extended from the central core 440 and extend the overall length of the handle 234 by 1.0 inches to about 5.0 inches. In some embodiments, the third sheath 444 is configured to extend from about 1.0 inches to about 5.0 inches from the central core 440. That is, the third sheath 444 may be extended from the central core 440 and extend the overall length of the handle 234 by 1.0 inches to about 5.0 inches.

In one example, a handle 234 was made. An example first control knob 436 was formed having a thread pitch of 2.50 millimeters, a screw lead of 5.0 millimeters, and an inner diameter of 21.40 millimeters. An example second control knob 438 was formed having a thread pitch of 2.50 millimeters, a screw lead of 5.0 millimeters, and an inner diameter of 14.0 millimeters. An example cap 582 was formed having a thread pitch of 2.50 millimeters, a screw lead of 5.0 millimeters, and an inner diameter of 11.4 millimeters.

The system disclosed herein provides a device and methods for translating rotational motion to longitudinal motion using one or more screws. This configuration has been found to provide a high mechanical force along the longitudinal axis that is controllable. The device disclosed herein provides an apparatus that allows a user to convey a high mechanical force, such as to the remote end of an elongated device, such as a retrieval tool comprising a lumen, to allow the user to attach and retrieve objects by receiving them within a capsule or catheter attached to the lumen. The first control knob 436 and the second control knob 438 are configured to convert rotational motion applied to the first control knob 436 and the second control knob 438 to linear or longitudinal motion of the second sheath 442 and third sheath 444 respectively.

In some examples, such as shown in FIG. 8, in a deployment configuration the hook assembly 210 shown in FIGS. 9A and 9B may be slidably received within the capsule assembly 212 shown in FIG. 10. The hook assembly lock 580 may be used to lock the hook assembly 210 to the handle 234. For example, as described with reference to FIG. 9B, the hook cable 220 may first be inserted within and locked to the hook sheath 222. Next, the hook assembly 210 may be slidably received within the handle 234, and the hook assembly lock 580 may be engaged and lock the hook assembly 210 the second end 532 of the third sheath 444. With the hook assembly 210 locked to the second end 532 of the third sheath 444, moving the second end 532 of the third sheath 444 toward or away from the central core 440 slides the hook assembly 210 in relation to the remaining portions of the capsule assembly 212. Also, with the hook assembly 210 locked to the second end 532 of the third sheath 444, moving the first end 510 of the second sheath 442 toward or away from the central core 440 slides the capsule shaft 232 and capsule 230 in relation to the hook assembly 210. In an example method of deployment, with the hook assembly 210 locked to the second end 532 of the third sheath 444, the second control knob 438 may be turned to draw the attachment feature 340 into the capsule 230, and the first control knob 436 may be turned to advance the capsule 230 over the attachment feature 340.

The retrieval device 200 previously described may be used for retrieval of an anchoring device such as the anchor 110 of the gastrointestinal device 100 previously described in FIGS. 1-7. In further instances, the retrieval device 200 and the methods disclosed herein for removing an anchoring device could be used for additional or alternative applications such as retrieval of stents or foreign bodies from within the gastrointestinal tract of a patient. The device and methods disclosed herein provide certain advantages, such as being capable of exerting a substantial amount of force, both in capturing a foreign object, and retracting the foreign object within a capsule, such as the capsule 230 described above. This advantage may be especially useful if the foreign object, such as a stent, is large and the user is trying to withdraw the object into a small tube or capsule for removal from inside a patient's body, or for example, if a device such as a stent is embedded within the patient's tissue and is to be removed.

In one example, an exemplary gastrointestinal implant can assume both an expanded and contracted configuration. The gastrointestinal implant may be held in place within a pylorus of a patient by using an anchor 110 as shown in FIG. 6. As previously described with reference to FIG. 6, the anchor may be formed from a hollow tubular braided structure that can assume a collapsed configuration for placement within and removal from a patient's digestive system. In some embodiments, the retrieval device 200 may be used to retrieve the anchor 110 from within a patient's body. For example, the retrieval device 200 may be used to remove the anchor from the stomach, pylorus, or intestine of a patient. Although described herein in reference to removing a gastrointestinal device from a patient's pylorus, the methods disclosed herein may be used to retrieve foreign bodies or objects from within a patient using the devices disclosed herein and using similar steps.

FIGS. 23 to 27 show the retrieval device 200, described above, in various stages of deployment to further illustrate a method of deploying. Using the deployment methods described herein, a device, such as the gastrointestinal device 100 shown in FIG. 7 that is positioned within a patient can be removed endoscopically, such as through the esophagus and throat of the patient. Using the deployment methods described herein, the gastrointestinal device 100 can be removed from within the patient without using surgery, for example, without forming an incision into the body of the patient.

Figure 23:
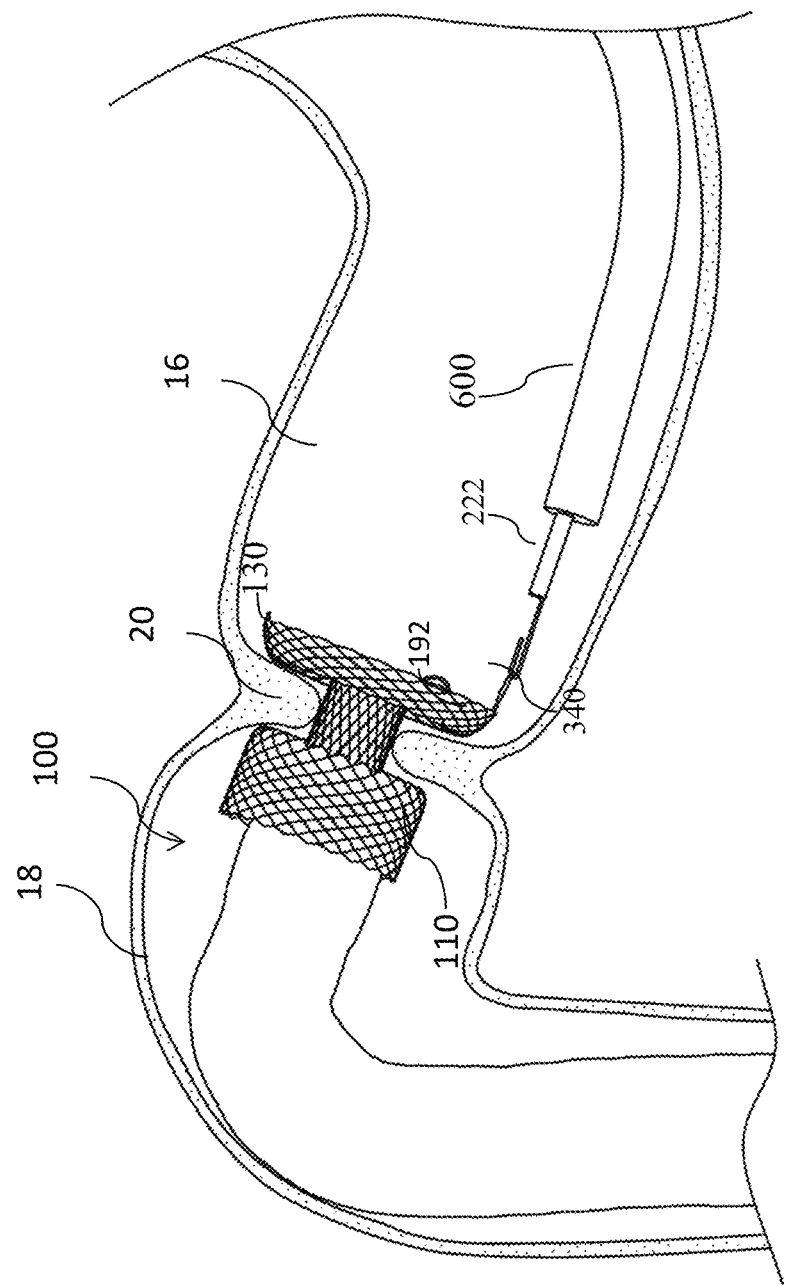
FIG. 23 is an illustration showing a deployment step in a retrieval method using the disclosed device, in accordance with various aspects of the present disclosure.

FIG. 23 shows the gastrointestinal device 100 described with reference to FIG. 7 positioned within the body of a patient with the anchor 110 positioned at the pylorus 20 between the stomach 16 and the intestine 18. In some instances, an endoscope 600 may be used to view the location of the anchor 110 and the drawstring 192. The tube of the endoscope 600 may also be used to guide the hook assembly 210 and the attachment feature 340 toward the drawstring 192 of the anchor 110. The attachment feature 340 may then be coupled to the drawstring 192 and can be pulled into the hook sheath 222 to collapse the proximal portion 130.

Figure 24:
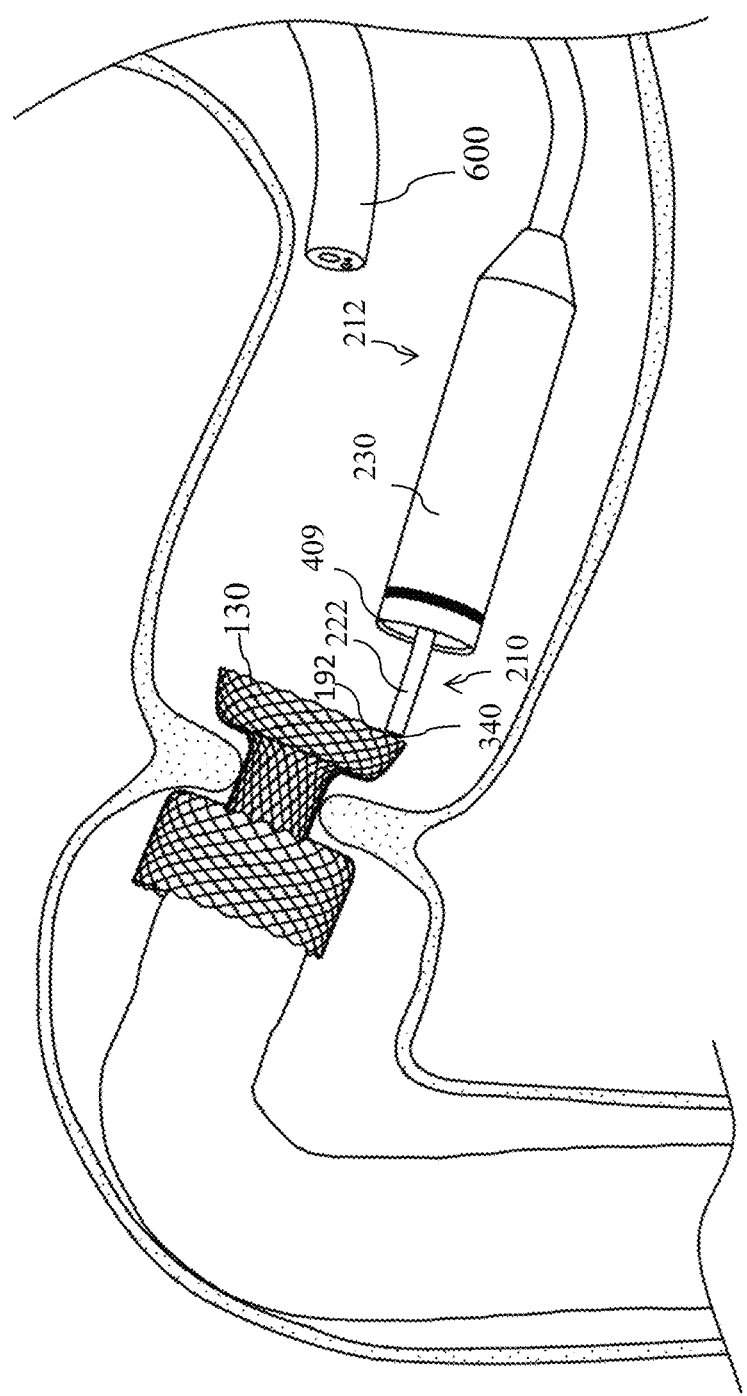
FIG. 24 is an illustration showing a deployment step in a retrieval method using the disclosed device, in accordance with various aspects of the present disclosure.

FIG. 24 shows the capsule assembly 212 and the hook assembly 210 after the endoscope 600 has been withdrawn from inside the patient. The attachment feature 340 is coupled to the drawstring 192, and the endoscope 600 has been replaced from around the hook assembly 210 by the capsule assembly 212. The capsule assembly 212 can be placed over the hook assembly 210 by inserting the second end (312 of the hook cable 220 shown in FIG. 9A) into the opening 409 of the capsule 230, and the capsule assembly 212 can be advanced into the patient around the hook assembly 210 until the capsule 230 is positioned near the attachment feature 340. The capsule assembly 212 may be positioned with the opening 409 of the capsule 230 positioned near the proximal portion 130, and may be positioned with the opening 409 of the capsule 230 positioned in contact with the proximal portion 130. The attachment feature 340 can be drawn into the capsule 230, such as by pulling the second end (312 shown in FIG. 9A) of the hook assembly 210 that remains outside the patient. The attachment feature 340 may be drawn into the capsule 230 and pull the proximal portion 130 until it contacts the opening 409 of the capsule 230. Drawing the attachment feature 340 into the capsule 230 while the proximal portion 130 remains outside the capsule 230 pulls the drawstring 192 from the proximal portion 130 and causes the proximal portion 130 to collapse in the radial direction. Once the proximal portion 130 is collapsed such that the outer diameter is smaller than the inner diameter of the capsule 230, the proximal portion 130 can be pulled into the capsule 230, such as by further pulling the hook assembly 210 through the capsule assembly 212.

Figure 25:
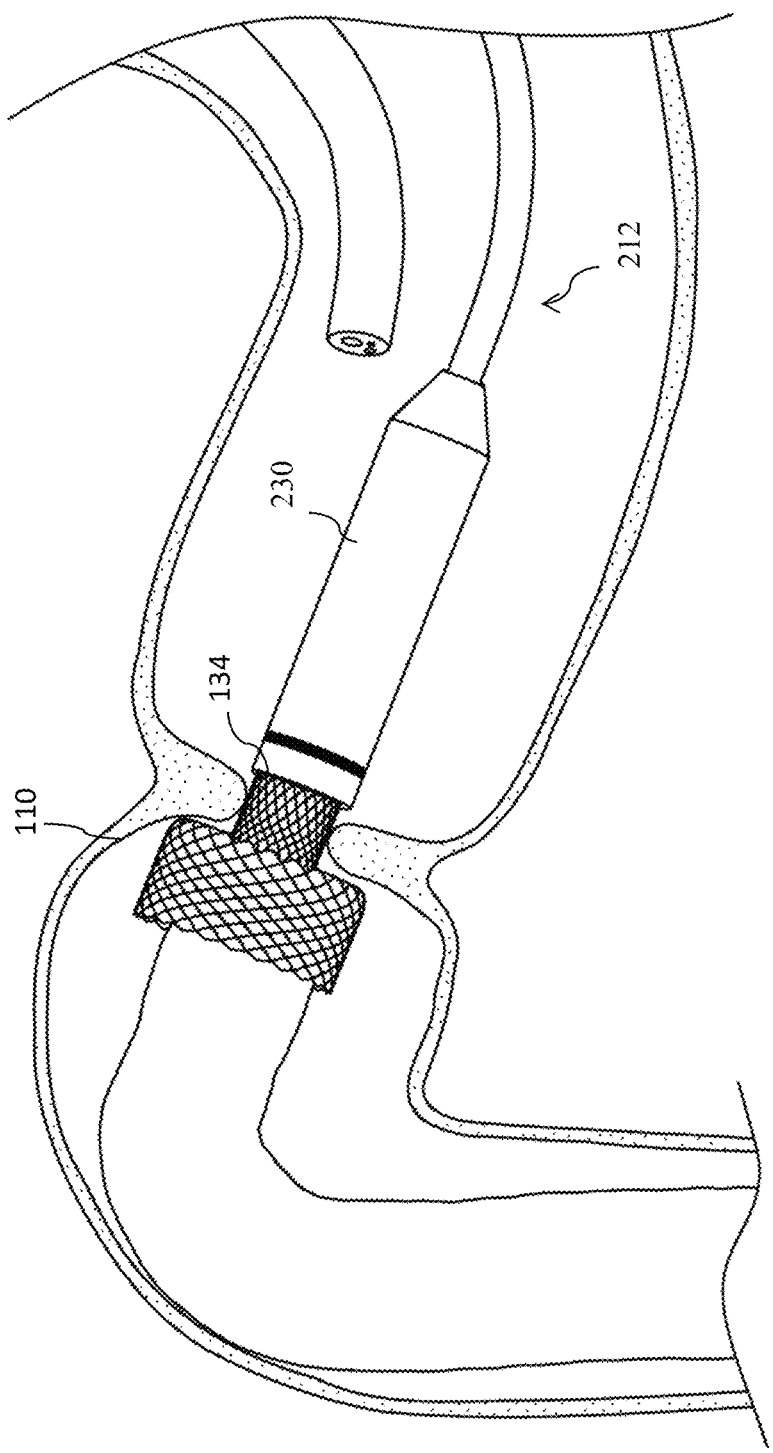
FIG. 25 is an illustration showing a deployment step in a retrieval method using the disclosed device, in accordance with various aspects of the present disclosure.

FIG. 25 shows the anchor 110 after the proximal portion 130 has been pulled into the capsule 230. As shown, the neck portion 134 is a suitable size such that it can be drawn into the capsule 230. The capsule 230 can alternatively be pushed over the neck portion 134. For example, by holding the hook assembly 210 (shown in FIG. 9A) which is still attached to the anchor 110 via the attachment feature 340 while pushing the capsule assembly 212 along the longitudinal axis, the capsule 230 is pushed over the anchor 110, and over the neck portion 134.

Figure 26:
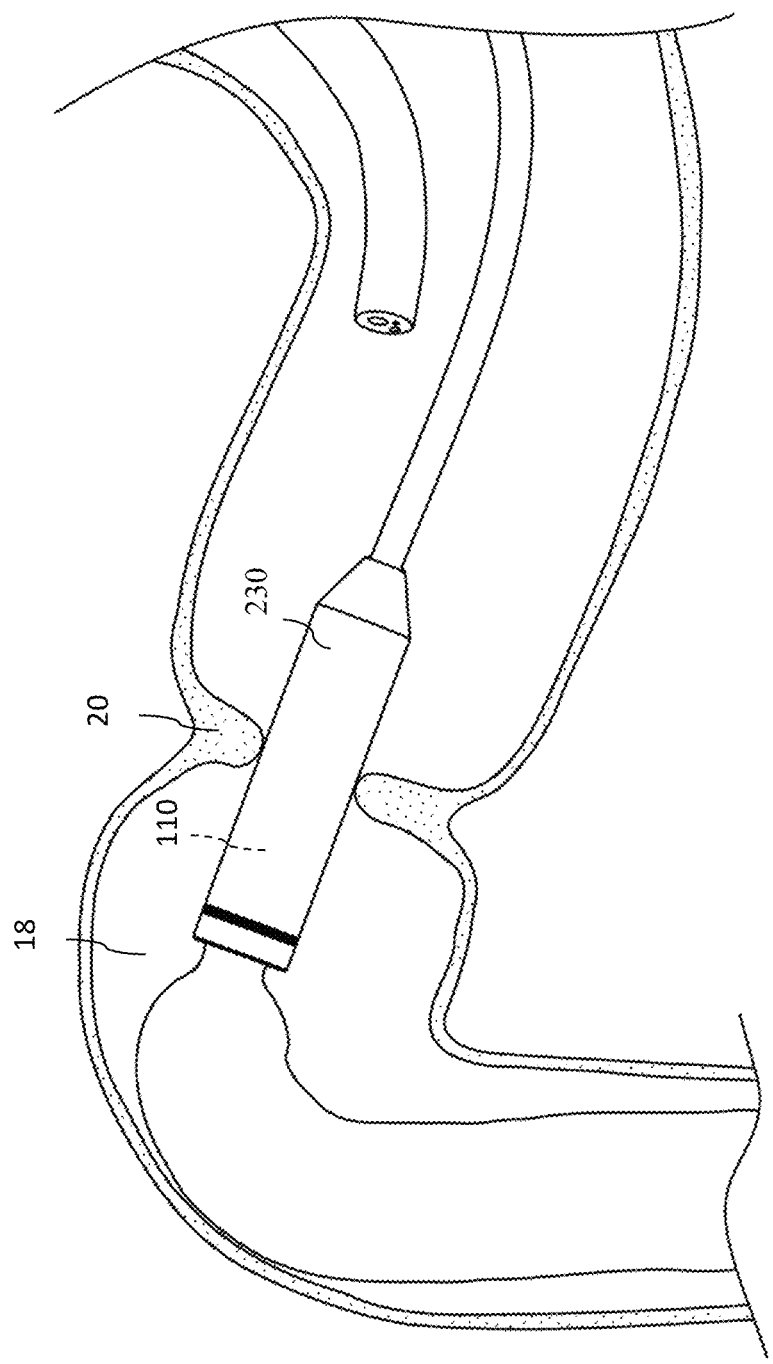
FIG. 26 is an illustration showing a deployment step in a retrieval method, in accordance with various aspects of the present disclosure.

FIG. 26 shows the capsule 230 after it has been pushed over the neck portion 134 of the anchor 110 and the remaining portions of the anchor 110, such as the distal portion (132 shown in FIG. 4). As shown, the capsule 230 may be pushed through the pylorus 20, for example, until the capsule 230 extends into the intestine 18. In some instances, the capsule 230 may be pushed over the distal portion (132), causing the distal portion 132 to collapse. The capsule 230 may be pushed through the pylorus 20 to cover the capsule 230 over the distal portion (132) of the anchor 110 and cause it to collapse.

Figure 27:
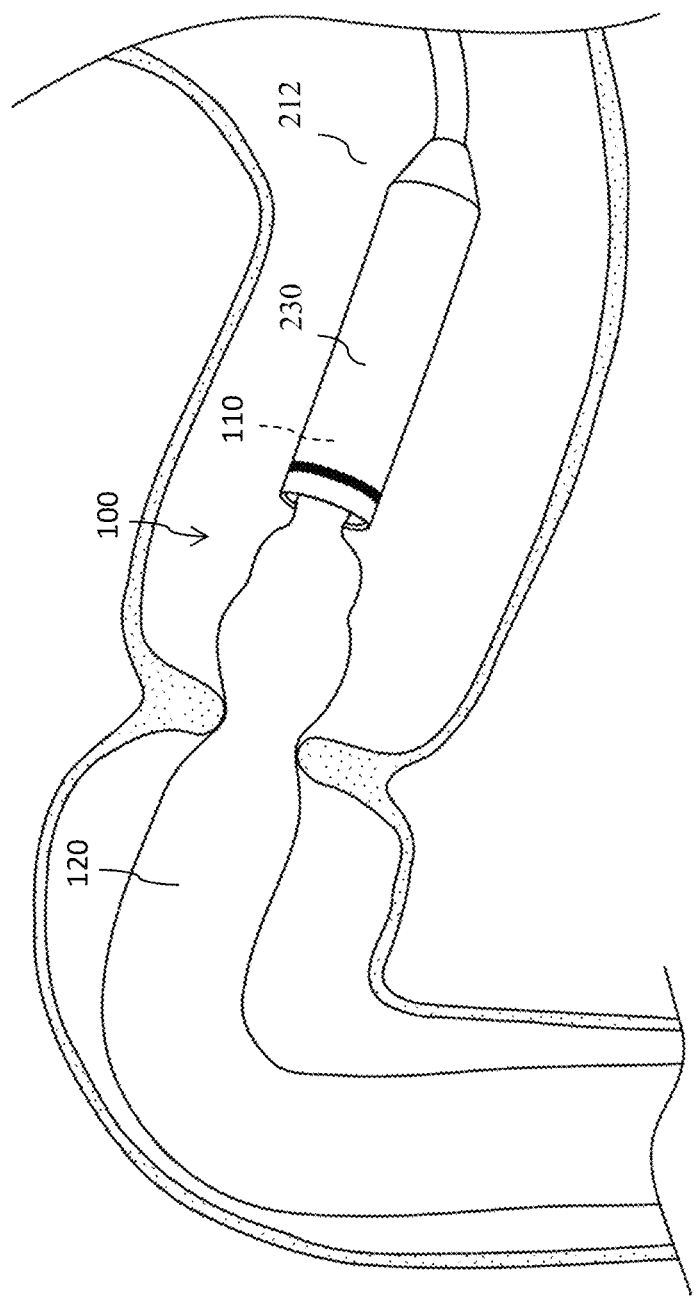
FIG. 27 is an illustration showing a deployment step in a retrieval method, in accordance with various aspects of the present disclosure.

FIG. 27 shows the gastrointestinal device 100 being withdrawn from the patient. The gastrointestinal device 100 may be pulled from inside the patient by pulling the capsule assembly 212, which draws the capsule 230 with the anchor 110 positioned inside. Pulling the anchor 110 draws the sleeve 120 which is attached to the anchor 110. The gastrointestinal device 100 may be pulled out from the patient through the esophagus and throat of the patient.

FIGS. 28 to 39 show the retrieval device 200 described above in various stages of deployment to illustrate a method of use. FIGS. 28 to 39 show various steps that may be used from a view showing sections of the retrieval device 200 within the patient and include inset views showing the deployment step from an additional vantage point, such as a different angle inside the patient and/or from outside the patient showing deployment steps for operating the portions of the retrieval device 200 that remain outside the patient.

Figure 28:
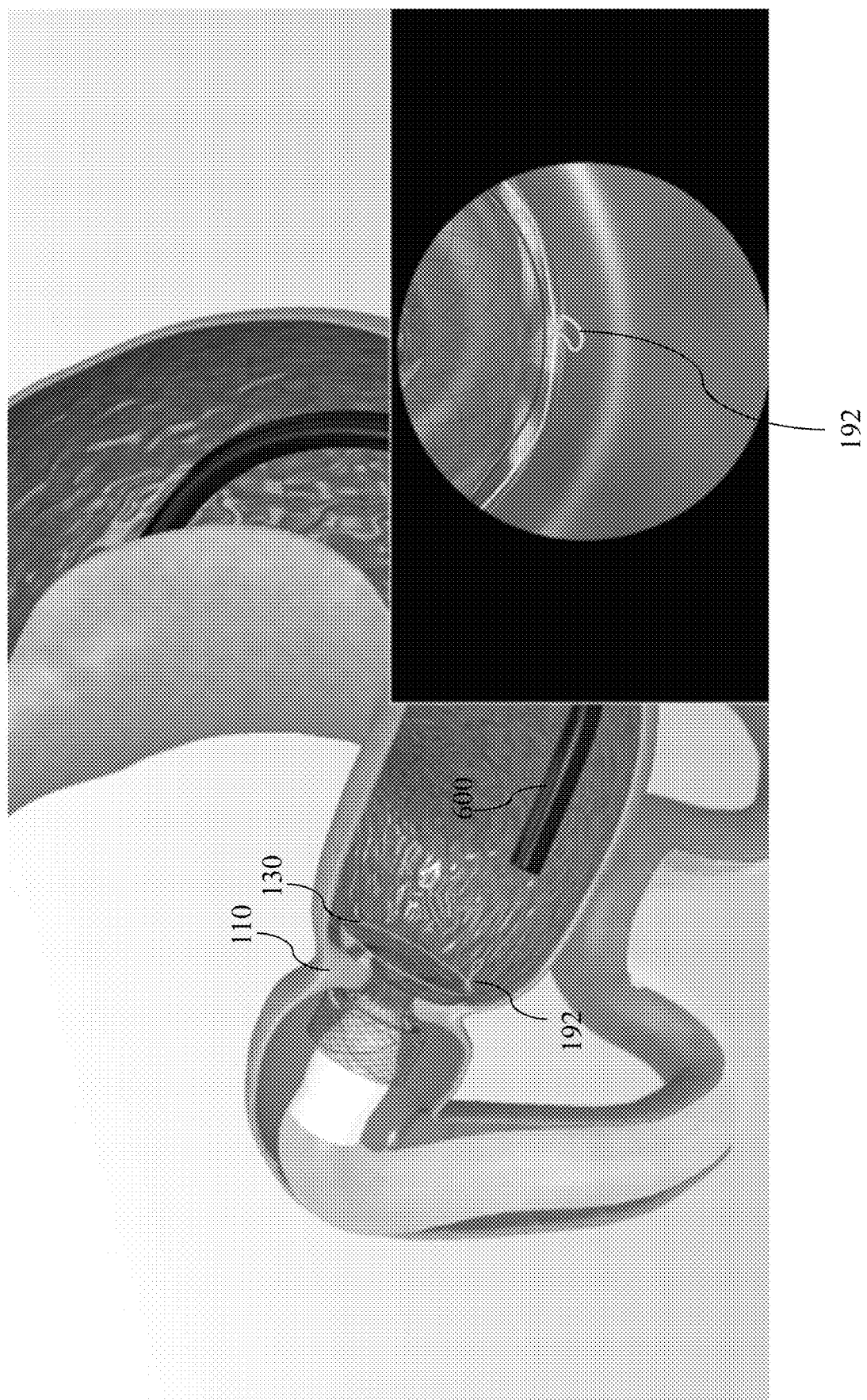
FIG. 28 is an illustration showing a deployment step in a retrieval method, in accordance with various aspects of the present disclosure.

FIG. 28 shows the anchor 110 described with reference to FIG. 6 positioned within the body of a patient at a pylorus between the stomach and the intestine. As shown in FIG. 28 in some embodiments, an endoscope 600 may be inserted into a patient and used to view the location of the anchor 110 and the drawstring 192. FIG. 28 includes an inset that is an alternative view from the perspective of the endoscope. A drawstring 192 may be included within the proximal portion 130 to provide a method of collapsing the proximal portion 130 and/or the anchor 110.

Figure 29:
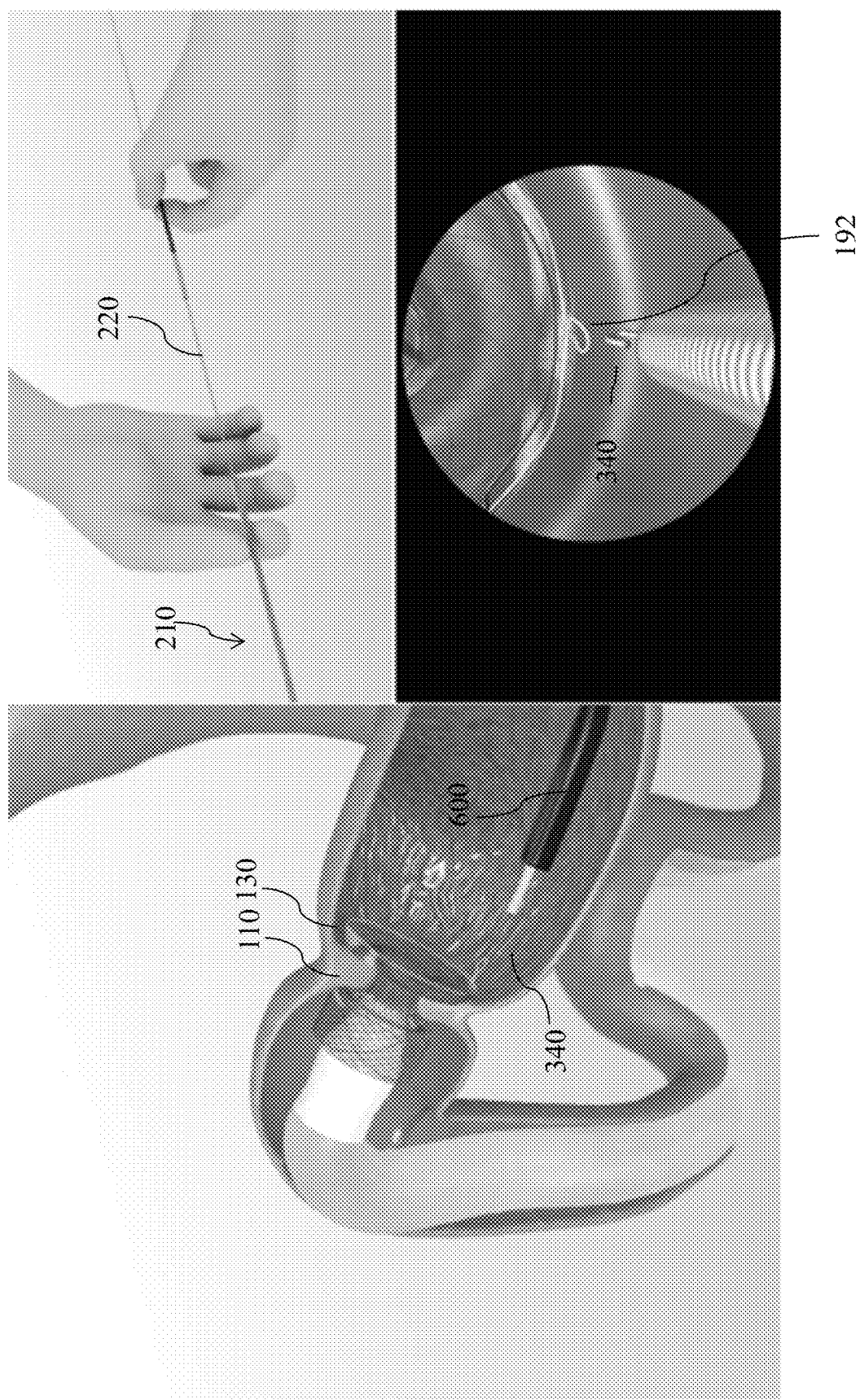
FIG. 29 is an illustration showing a deployment step in a retrieval method, in accordance with various aspects of the present disclosure.

FIG. 29 shows the hook assembly 210 including the hook cable 220 inserted into the endoscope tube. The endoscope 600 may be used to view the drawstring 192 and guide the attachment feature 340. As shown in the inset view of FIG. 29, the endoscope 600 may be used to guide the attachment feature 340 and attach it to the drawstring 192.

Figure 30:
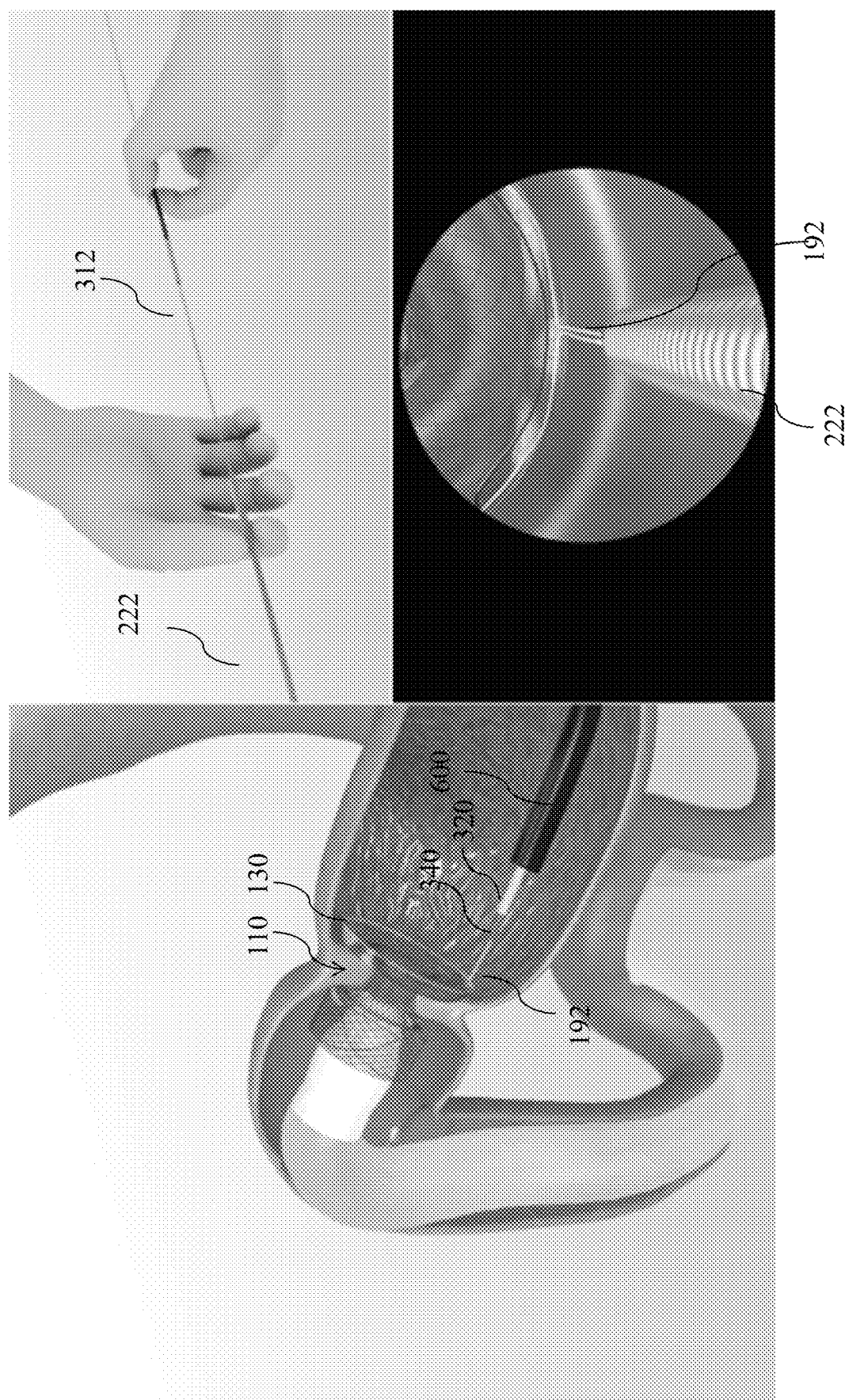
FIG. 30 is an illustration showing a deployment step in a retrieval method, in accordance with various aspects of the present disclosure.

FIG. 30 shows the attachment feature 340 attached to the drawstring 192. After attaching the attachment feature 340 to the drawstring 192, the attachment feature 340 may be retracted into the hook sheath 222 by pulling the second end 312 of the hook cable 220 (shown in FIG. 9A). Pulling the second end 312 of the hook cable 220, while maintaining the hook sheath 222 in position causes the attachment feature 340 to retract into the hook sheath 222 bringing the drawstring 192 into the hook sheath 222 as well. The first end 320 of the hook sheath 222 is too narrow for the proximal portion 130 of the anchor 110 to enter into the hook sheath 222 while in the expanded configuration. Pulling the drawstring 192 further into the hook sheath 222 pulls the drawstring 192 away from the proximal portion 130 which causes the proximal portion 130 to collapse in size. The drawstring 192 may be further pulled out from the anchor 110 which causes the proximal portion 130 to further collapse until it transitions into a contracted configuration.

Figure 31:
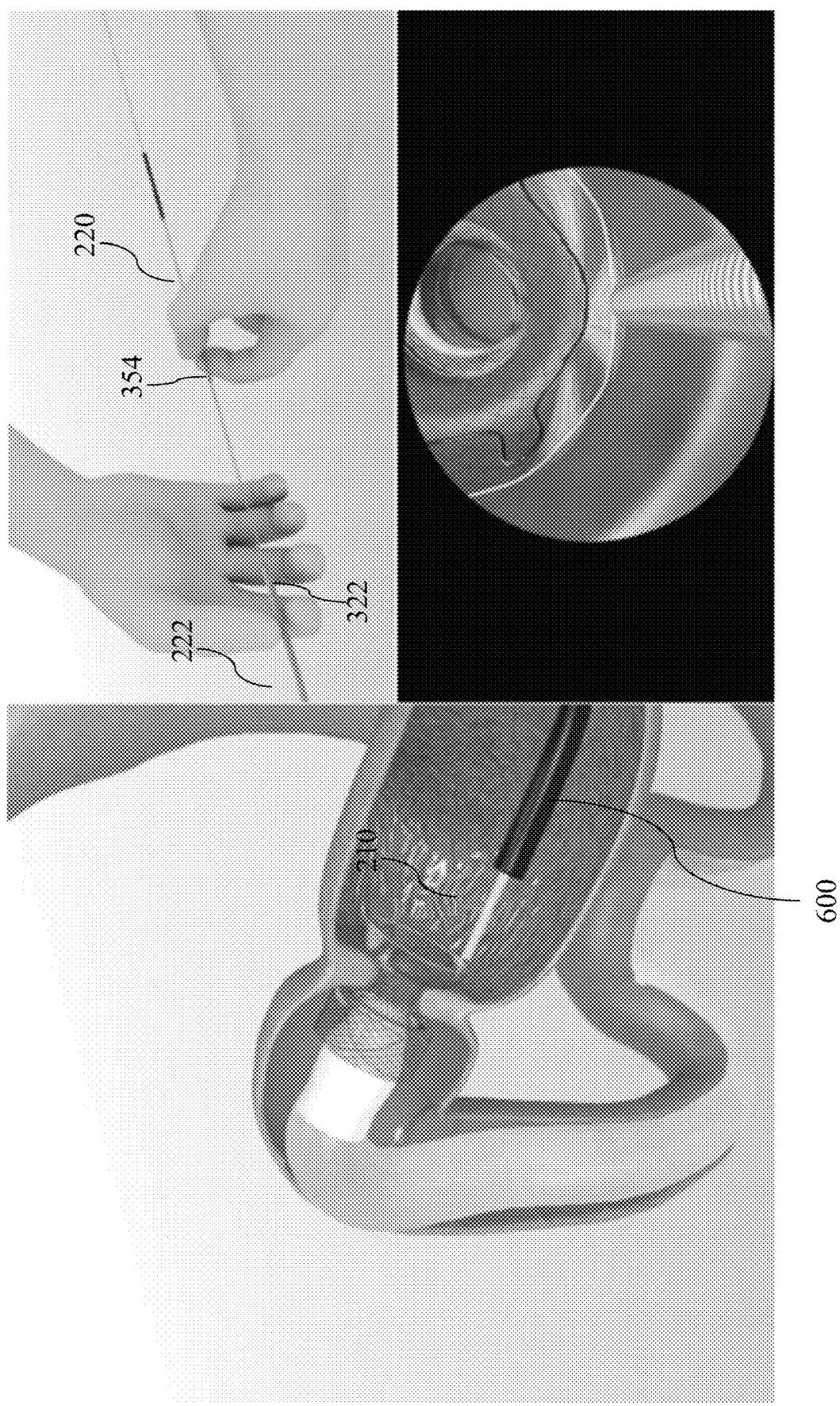
FIG. 31 is an illustration showing a deployment step in a retrieval method, in accordance with various aspects of the present disclosure.

FIG. 31 shows the locking sheath 354 being advanced along the hook cable 220 toward the second end 322 of the hook sheath 222. In some instances, the hook cable 220 and the hook sheath 222 can be locked together to prevent them from moving in longitudinal relation to each other. In some examples, the hook cable 220 and the hook sheath 222 can formed as a single unitary structure and comprise the hook assembly 210. In some examples, the hook cable lock 350 may be used to lock the hook cable 220 and the hook sheath 222 together to form the hook assembly 210. As previously described with reference to FIG. 9, in some embodiments, the locking sheath 354 can be used to prevent the hook cable 220 from advancing further into the hook sheath 222 toward the second end 322 of the hook sheath 222. In some examples, the endoscope 600 may be removed from the patient. The endoscope 600 may be removed from the patient leaving the hook assembly 210 in place inside the patient.

Figure 32:
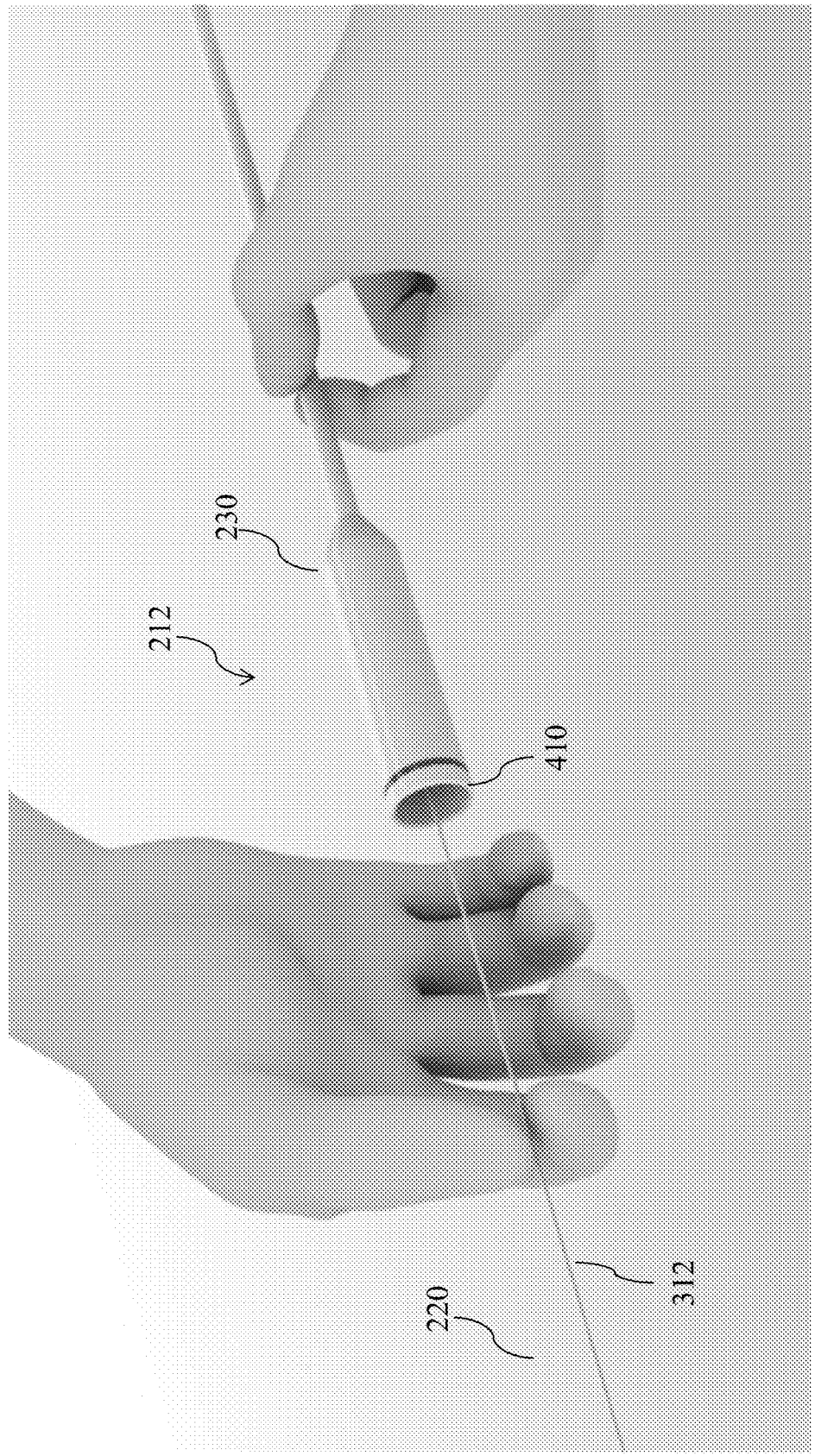
FIG. 32 is an illustration showing a deployment step in a retrieval method, in accordance with various aspects of the present disclosure.

FIG. 32 shows the second end 312 of the hook cable 220, which remains outside the body of the patient, being inserted into the capsule assembly 212. The hook cable 220 may be inserted into the capsule assembly 212 by inserting the second end 312 of the hook cable 220 into the first end 410 of the capsule 230. After the hook cable 220 is inserted into the capsule assembly 212, the capsule assembly 212 may be inserted into the patient and advanced until the capsule 230 reaches a suitable position. The capsule assembly 212 is guided into position by advancing the capsule assembly 212 over the hook cable 220 which is attached to the anchor 110 which is still in place within the patient. The capsule assembly 212 may be inserted into the patient by advancing it along the outside of the hook assembly 210. That is, the hook assembly 210 may be held stationary, while the capsule assembly 212 is advanced into the patient with the capsule assembly 212 advancing around the hook assembly 210. In this manner, the capsule assembly is guided into place adjacent the anchor 110.

Figure 33:
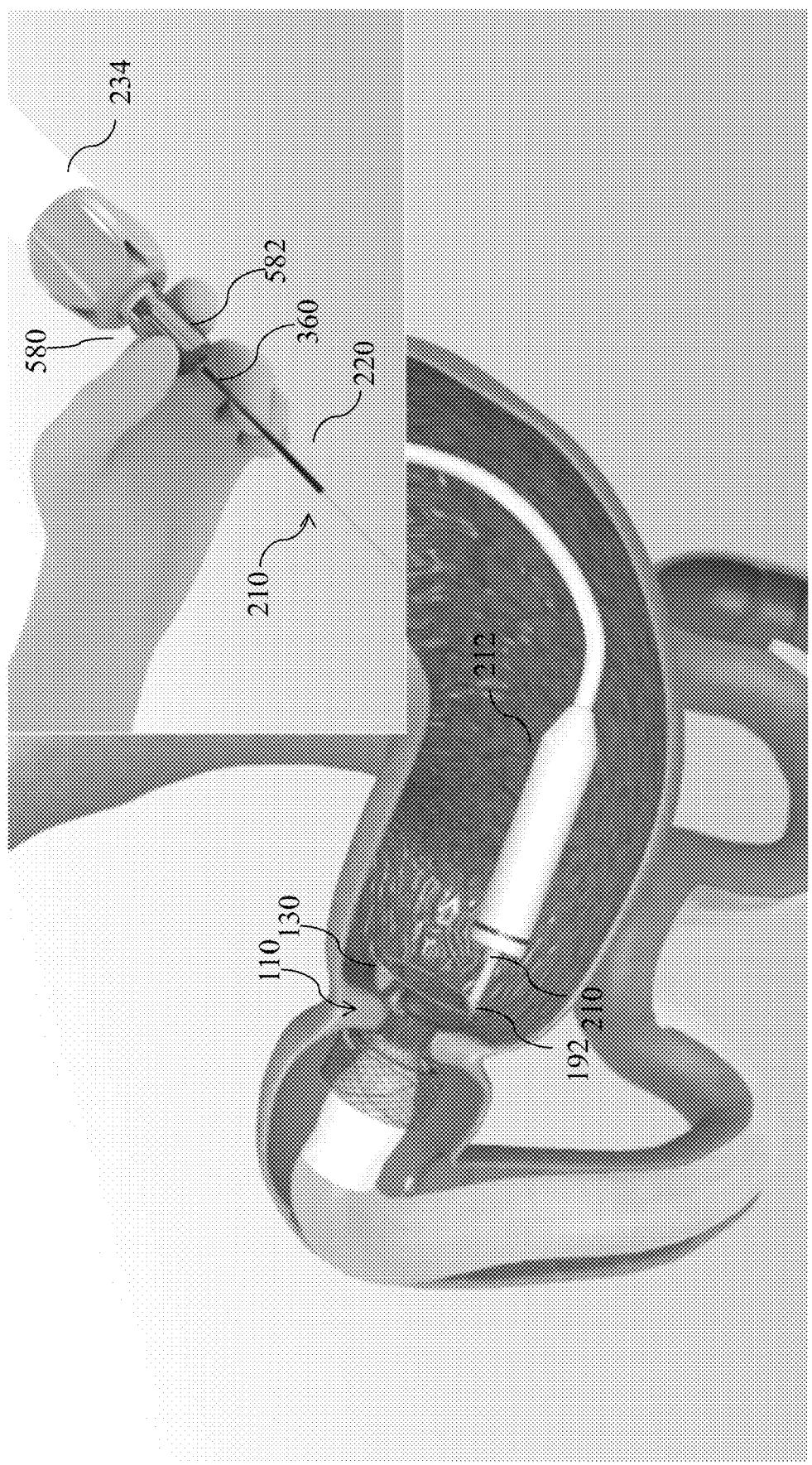
FIG. 33 is an illustration showing a deployment step in a retrieval method, in accordance with various aspects of the present disclosure.

FIG. 33 shows the capsule assembly 212 positioned inside the patient and around the hook cable 220. The capsule assembly 212 is in place within the patient, and the hook assembly 210 is attached to the drawstring 192. As shown in the inset of FIG. 28, once the capsule assembly 212 is in place, the hook assembly lock 580 may be engaged to lock the hook assembly 210 in longitudinal relation with the capsule assembly 212. As previously described in reference to FIG. 21B, turning the cap 582 of the hook assembly lock 580 decreases the inner diameter of the second end 532 of the third sheath 444. Decreasing the inner diameter of the second end 532 of the third sheath 444 with the hook cable stop 360 within the hook assembly lock 580 locks the third sheath and the hook cable 220 together and locks the hook cable 220 to the second end 532 of the third sheath 444. This also joins the hook assembly 210 and the capsule assembly 212 together in longitudinal relation to each other. In some embodiments, an endoscope may be inserted again into the patient to provide viewing for a healthcare worker.

Figure 34:
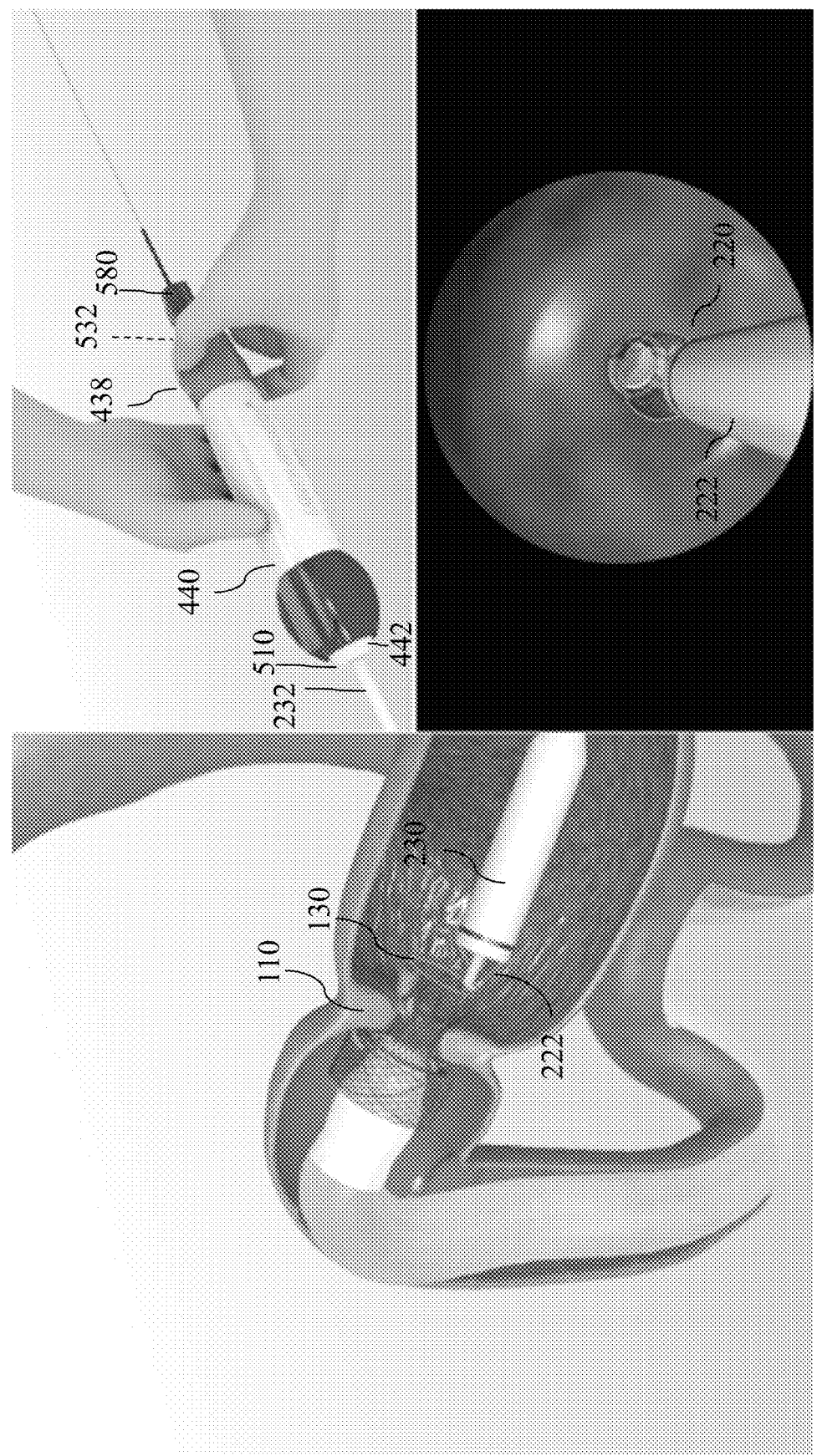
FIG. 34 is an illustration showing a deployment step in a retrieval method, in accordance with various aspects of the present disclosure.

FIG. 34 shows the second control knob 438 being turned in relation to the central core 440. As previously described with reference to FIGS. 22A and 22B, turning the second control knob 438 moves the second end 532 of the third sheath 444 in relation to the central core 440. The second control knob 438 may be turned to extend the second end 532 of the third sheath 444 away from the central core 440 and extending the length of the handle 234. As shown in FIG. 34, the first end 510 of the second sheath 442 is attached to the capsule shaft 232, which is in turn attached to the capsule 230. Because the hook sheath 222, capsule shaft 232, and capsule 230 are incompressible, and because the hook assembly 210 is attached to the second end 532 of the third sheath 444, extending the second end 532 of the third sheath 444 away from the central core 440 pulls the hook assembly 210 through the capsule shaft 232. This causes the hook cable 220 to pull the drawstring 192 further into the hook sheath 222 and collapses the proximal portion 130 of the anchor 110. The hook cable 220 may be drawn into the hook sheath 222 until the proximal portion 130 is fully collapsed.

Figure 35:
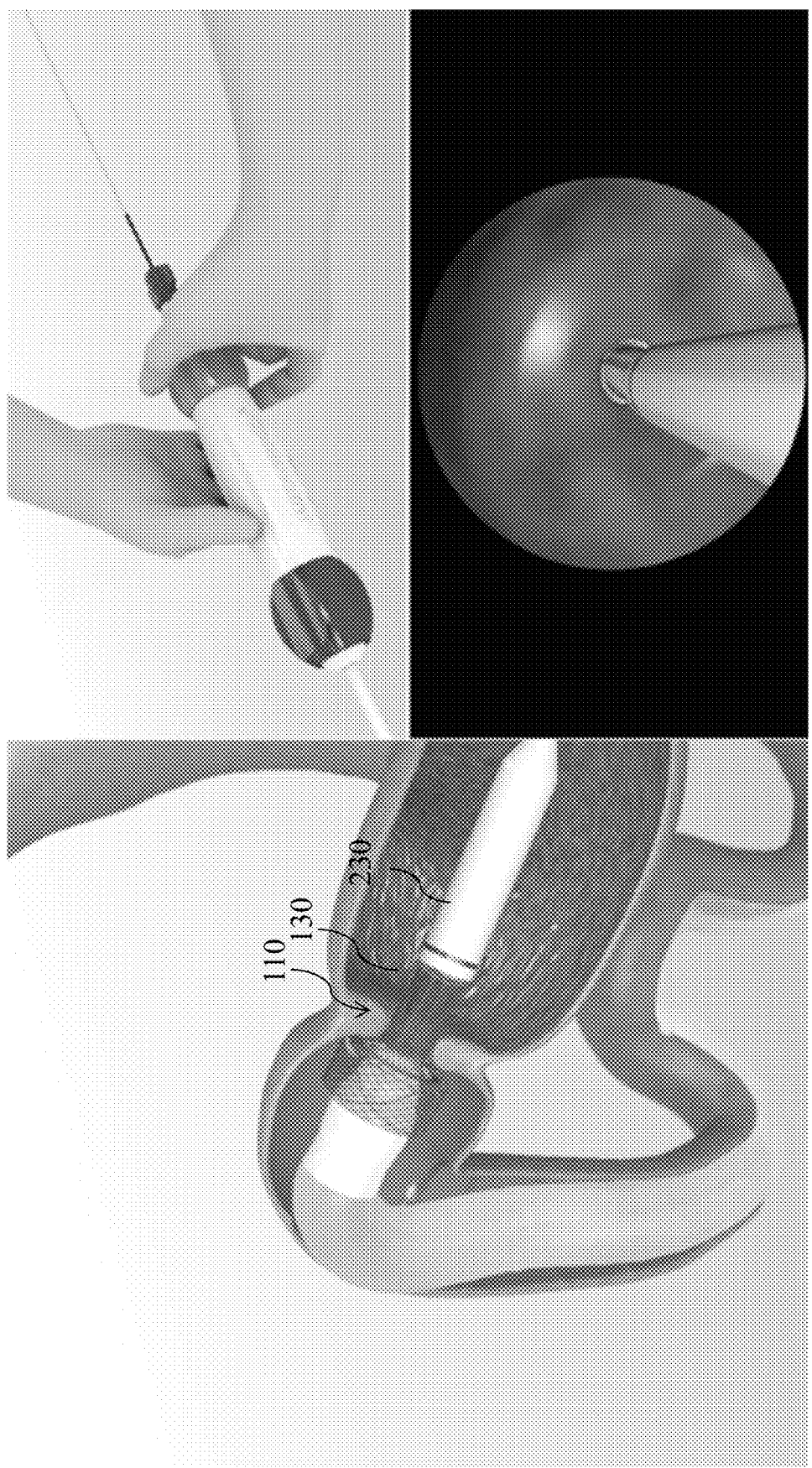
FIG. 35 illustrates a deployment step in a retrieval method, in accordance with various aspects of the present disclosure.
Figure 36:
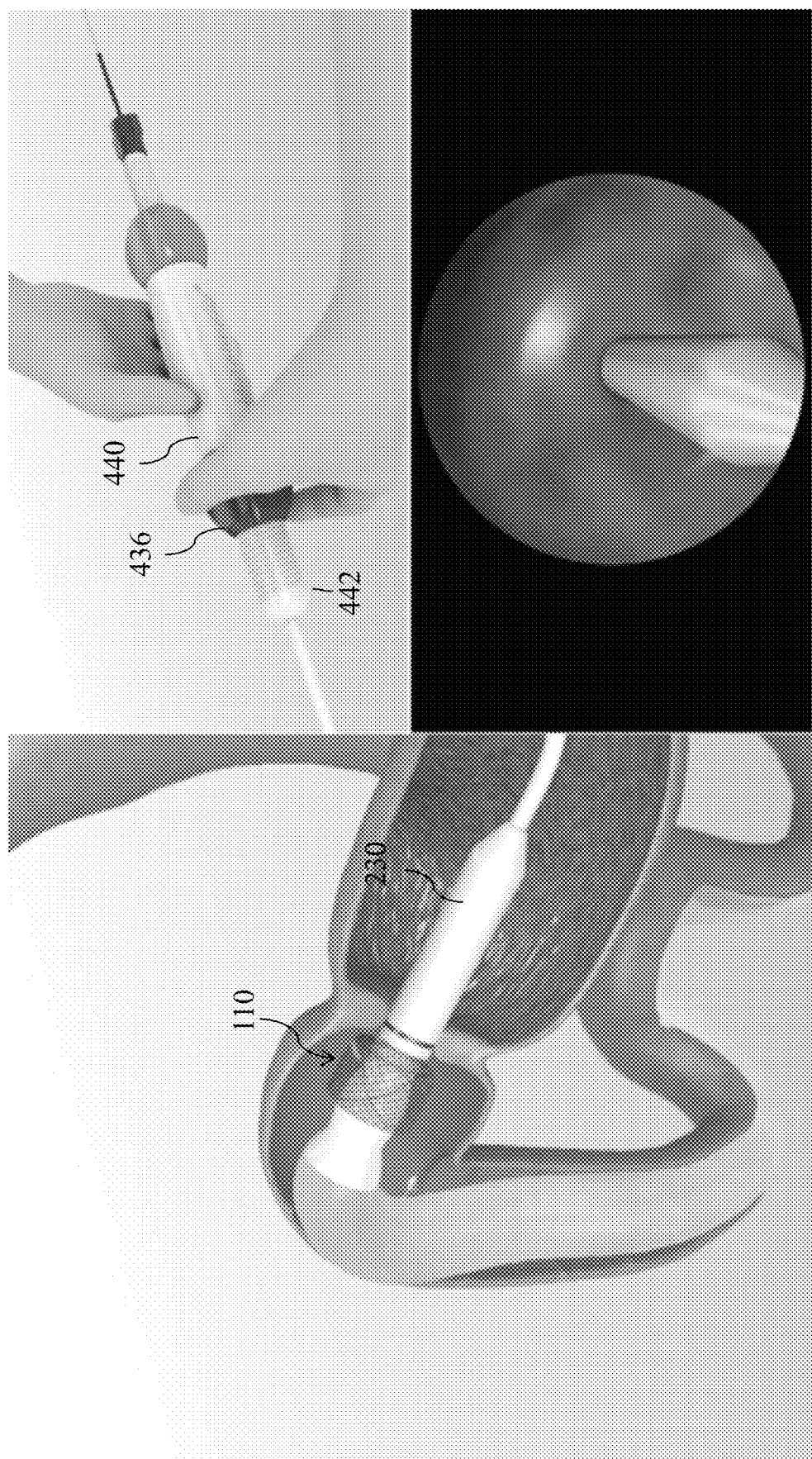
FIG. 36 illustrates a deployment step in a retrieval method, in accordance with various aspects of the present disclosure.
Figure 37:
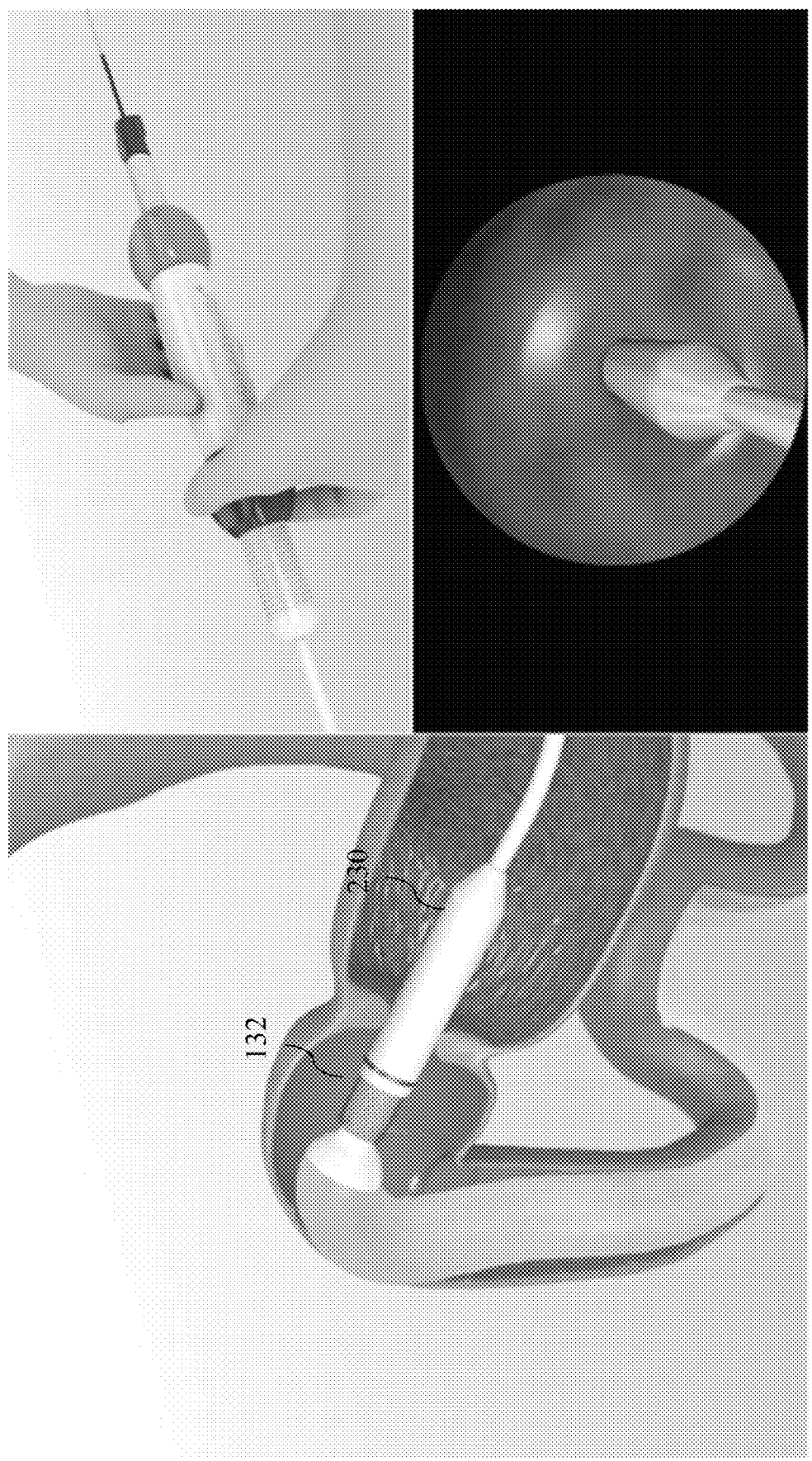
FIG. 37 illustrates a deployment step in a retrieval method, in accordance with various aspects of the present disclosure.
Figure 38:
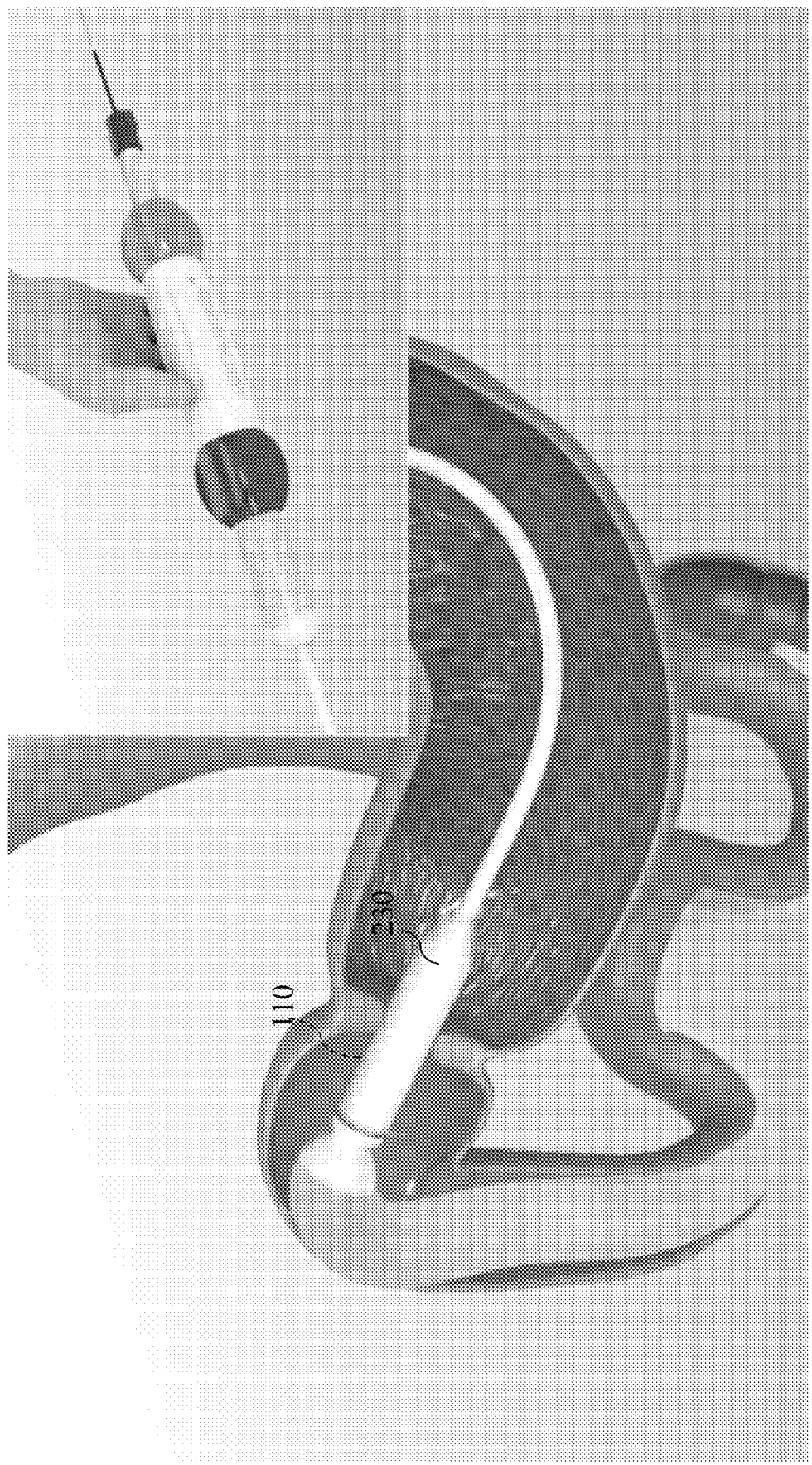
FIG. 38 illustrates a deployment step in a retrieval method, in accordance with various aspects of the present disclosure.
Figure 39:
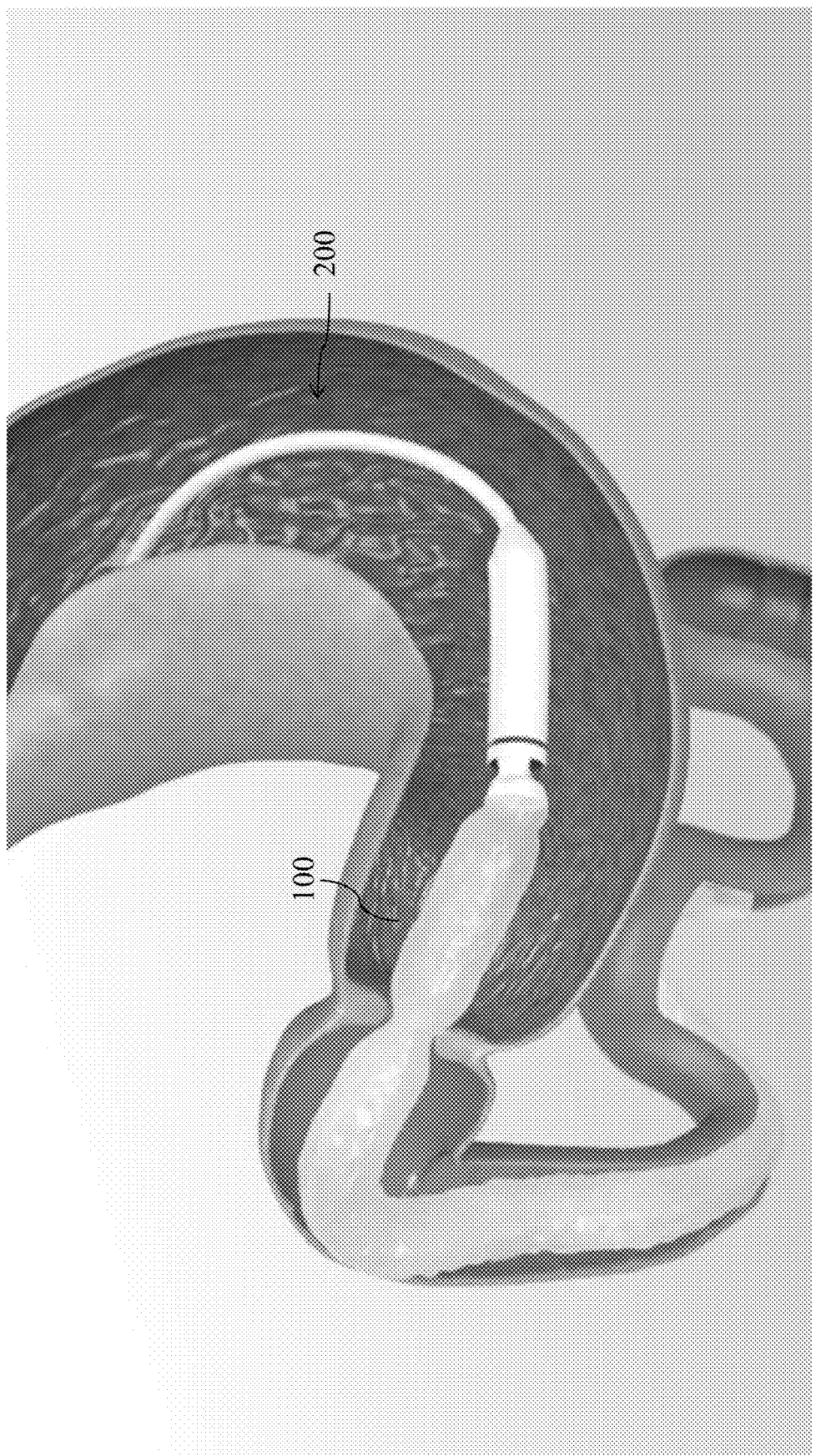
FIG. 39 illustrates a deployment step in a retrieval method, in accordance with various aspects of the present disclosure.

FIG. 35 shows the proximal portion 130 of the anchor 110 collapsed and aligned with the capsule 230. Once the proximal portion 130 of the anchor 110 is collapsed, it can be pulled into the capsule 230. FIG. 36 shows the proximal flange fully received inside the capsule 230 and the capsule 230 extending through the patient's pylorus. Once the proximal flange has been collapsed, the neck portion of the anchor 110 may be drawn into the capsule 230. Turning the first control knob 436 further, extends the second sheath 442 away from the central core 440 and pushes the capsule 230 over the anchor 110. As shown in FIG. 37, the capsule 230 may be advanced further until the capsule presses against the distal portion 132, causing the distal portion 132 to collapse. As shown in FIG. 38, the entire anchor 110 may be pulled into the capsule 230. With the anchor 110 in the fully collapsed configuration and contained inside the capsule 230, the gastrointestinal device 100 can be removed from within the patient. As shown in FIG. 39, the gastrointestinal device 100 can be removed from within the patient by pulling the retrieval device 200 out of the patient.

The device and methods described herein may be used to remove a gastrointestinal device from within a patient. In some embodiments, the device and methods disclosed herein may be used to remove a variety of foreign objects from within a patient. Generally, the device includes an attachment or securement device for attaching to the object such as a drawstring on a gastrointestinal anchor. The attachment or securement device may be withdrawn into a capsule or lumen that reduces the overall size of the foreign object to facilitate removal of the foreign object. Once the attachment or securement device is attached to or enclosing the foreign object, the capsule or lumen may be advanced over the object.

In some embodiments, the device disclosed herein provides a rigid shaft that may withstand considerable compressive forces without deforming. The device disclosed herein also provides a mechanism for drawing a foreign object into a protective lumen device to facilitate removal of the foreign object. The embodiments disclosed herein provide a cable for the attachment feature and a means of exerting a longitudinal force between the cable and the protective lumen device. The handle design and shaft characteristics disclosed herein allow for a user to exert a considerable amount of force to pull the hook into the capsule. The handle disclosed above may be used to provide very high tensile forces to the cable using a screw thread with a shallow pitch. That is, the design disclosed herein allows a handle to incorporate a shallow pitched screw thread, which enables a user to draw the hook into the capsule by transferring high amounts of force, yet requires relatively low circumferential force to turn the screw. A suitable thread pitch may be used to provide a handle that can provide high leverage through each turn of the control knobs. Thus, using the device and methods disclosed herein, a retrieval device that may transfer high tensile force to withdraw foreign objects from inside a patient is provided.

In some embodiments, the device and methods disclosed herein provide an endoscopic retrieval system that can deliver and/or remove a medical device from a patient's gastrointestinal tract with minimal trauma to the gastrointestinal tract. A delivery and/or retrieval system may include a distal capsule to hold the implant, a sleeve delivery catheter to track over a guidewire and a handle to deploy the implant. The retrieval system may employ a through-the-scope (TTS) retrieval catheter that engages a drawstring on the implant. Once the implant is engaged, the scope is removed, and a second catheter with a distal capsule is advanced over the TTS catheter and retracts the implant into the capsule. Once the implant is fully retracted into the capsule, it is removed. In some embodiments, a delivery or retrieval method may take less than 25 minutes to perform.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the above described features.

The following is claimed:

1. A retrieval device comprising:
a hook assembly having an attachment feature;
a capsule assembly including:
 a capsule, a capsule shaft, and a handle connected in series and defining an inner bore along a length of the capsule assembly, the capsule having a first end defining an opening to the inner bore of the capsule assembly and configured to slidably receive the hook assembly, and
 the handle having a central portion, a first extension portion having a first end defining a first end of the handle and attached to the capsule shaft, and a second extension portion having a second end defining a second end of the handle, the handle having a retracted configuration with the first end a first distance from the second end and an extended configuration with the first end a second distance from the second end, the first distance less than the second distance,
 wherein the handle includes a first control knob configured to transition the first extension portion between the retracted configuration and the extended configuration, and a second control knob configured to transition the second extension portion between the retracted configuration and the extended configuration.

2. The retrieval device of claim 1, wherein the second extension portion has a hook assembly lock at the second end configured to lock the hook assembly to the second extension portion, and wherein the second extension portion is configured to pull the hook assembly relative to the capsule shaft, and the first extension portion is configured to push the capsule shaft relative to the hook assembly.

3. The retrieval device of claim 1, wherein the attachment feature is a hook.

4. The retrieval device of claim 1, wherein the capsule assembly is incompressible along the central longitudinal axis.

5. The retrieval device of claim 1, wherein a second end of the capsule is attached to a first end of the capsule shaft and a second end of the capsule shaft is attached to the first end of the first extension portion.

6. The retrieval device of claim 1, wherein the capsule comprises a closely packed coil.

7. The retrieval device of claim 1, wherein the capsule is flexible to bend at an angle relative to a central longitudinal axis of the capsule assembly.

8. The retrieval device of claim 1, wherein the first control knob and second control knob are configured to convert a rotational motion to a linear motion between the hook assembly and the capsule shaft in a longitudinal direction.

9. The retrieval device of claim 1, wherein the handle is configured to draw the attachment feature into the first end of the capsule with a medical device attached to the attachment feature.

10. The retrieval device of claim 1, wherein the retrieval device is configured to transition a medical device from an expanded configuration to a collapsed configuration and draw the medical device into the capsule in the collapsed configuration.

11. The retrieval device of claim 1, further comprising a tip at the first end of the capsule, the tip configured to removably cover the opening to the inside of the capsule.

12. A retrieval device for retrieving an object from within a body of a patient, the retrieval device comprising:
- a hook assembly including:
    - a sheath having a first end, a second end, and a wall extending between the first end and the second end and defining a lumen in between,
    - a hook cable lock situated proximal the second end of the sheath, and
    - a cable having an attachment feature at a first end, the cable configured to be slidably received within the lumen of the sheath,
    - wherein the hook cable lock is configured to lock a second end of the cable to inhibit longitudinal motion of the cable relative to the sheath; and
    - wherein the hook assembly includes a hook cable stop situated proximal the hook cable lock along the cable and configured to be inhibited from entering the sheath; and
- a capsule assembly including:
    - a capsule, a capsule shaft, and a handle connected in series and defining an inner bore along a length of the capsule assembly, the capsule having a first end defining an opening to the inner bore of the capsule assembly and configured to slidably receive the hook assembly in the inner bore, and
    - the handle having a central portion, a first end defining a first end of the handle and attached to the capsule shaft, and a second end defining a second end of the handle configured to lock the hook assembly to the second end of the handle such that the hook assembly is inhibited from moving relative to the second end of the handle.

13. The retrieval device of claim 12, wherein the hook cable lock includes a locking mechanism configured to lock the cable in place.

14. The retrieval device of claim 12, wherein the handle has a retracted configuration with the first end a first distance from the second end, and an extended configuration with the first end a second distance from the second end, and the inner bore of the capsule assembly is configured to slidably receive the hook assembly along a central longitudinal axis, such that transitioning the handle between the retracted configuration and the expanded configuration slides the hook assembly relative to the capsule shaft along the central longitudinal axis.

15. The retrieval device of claim 14, wherein transitioning the handle between the retracted configuration and the expanded configuration draws the attachment feature into the capsule.

16. A method of extracting a medical device from within a patient, the method comprising:
- inserting an attachment assembly including an attachment cable having a first end attached to an attachment feature into a body of a patient;
- coupling the attachment feature to a medical device positioned within the body of the patient;
- advancing a capsule assembly into the body of the patient, where the capsule assembly has a capsule at a first end and a handle at a second end of the capsule assembly;
- locking a second end of the attachment cable to the handle;
- transitioning the handle from a first configuration to a second configuration such that the attachment feature is positioned within the capsule, wherein transitioning the handle from a first configuration to a second configuration comprises turning at least one of a first control knob and a second control knob, the first control knob and second control knob configured to translate rotational motion to longitudinal motion along a longitudinal axis of the handle; and
- removing the capsule assembly and attachment assembly coupled to the medical device from inside the body of the patient.

17. The method of claim 16, wherein transitioning the handle from a first configuration to a second configuration comprises extending a length of the handle along a longitudinal axis of the handle.

18. The method of claim 16, wherein extending a length of the handle at a first end advances the capsule over the attachment feature and extending the length of the handle at a second end draws the attachment feature into the capsule.

* * * * *